United States Patent [19]

Dininno et al.

[11] Patent Number: 5,208,329

[45] Date of Patent: * May 4, 1993

[54] 2-BIPHENYL CARBAPENEM INTERMEDIATES

[75] Inventors: Frank P. Dininno, Old Bridge; Thomas N. Salzmann, North Plainfield, both of N.J.

[73] Assignee: Merck & Co., Inc., Rahway, N.J.

[*] Notice: The portion of the term of this patent subsequent to Apr. 30, 2008 has been disclaimed.

[21] Appl. No.: 839,005

[22] Filed: Feb. 14, 1992

Related U.S. Application Data

[63] Continuation of Ser. No. 594,886, Oct. 9, 1990, abandoned.

[51] Int. Cl.$^5$ .................. C07D 487/04; C07F 7/18
[52] U.S. Cl. .................... 540/302; 514/210; 514/938; 424/452; 424/489
[58] Field of Search .......................... 540/302

[56] References Cited

U.S. PATENT DOCUMENTS

| Re. 33,495 | 12/1990 | Rudzuma et al. | 546/209 |
|---|---|---|---|
| 4,260,627 | 4/1981 | Christensen et al. | 514/210 |
| 4,465,632 | 8/1984 | Christensen et al. | 540/302 |
| 4,543,257 | 9/1985 | Cama et al. | 514/210 |
| 4,775,669 | 10/1988 | Cama et al. | 514/210 |
| 4,962,101 | 10/1990 | DiNinno et al. | 514/210 |
| 4,988,703 | 1/1991 | Norbeck et al. | 514/262 |
| 5,003,099 | 3/1991 | Mettler et al. | 558/445 |
| 5,011,832 | 4/1991 | Dininno et al. | 514/210 |
| 5,011,848 | 4/1991 | Semararo et al. | 514/356 |
| 5,015,260 | 5/1991 | Tamara et al. | 564/443 |
| 5,019,173 | 5/1991 | Gettings et al. | 134/4 |
| 5,023,250 | 6/1991 | Adams et al. | 514/179 |
| 5,026,869 | 6/1991 | Semeraro et al. | 514/356 |
| 5,029,979 | 7/1991 | Robello et al. | 385/141 |

FOREIGN PATENT DOCUMENTS 0277743 8/1988 European Pat. Off. .

OTHER PUBLICATIONS

L. D. Cama et al., Total Synthesis of Thienamycin Analogs-III, *Tetrahedron 39*, 2531 (1983).
R. N. Guthikonda, et al., Structure Activity Relationships in the 2-Arylcarbapenem Series, *J. Med. Chem.*, 30, 871 (1987).

*Primary Examiner*—Thurman K. Page
*Assistant Examiner*—Jyothsna Venkat
*Attorney, Agent, or Firm*—Richard C. Billups; Raymond M. Speer

[57] ABSTRACT

Carbapenems of the formula

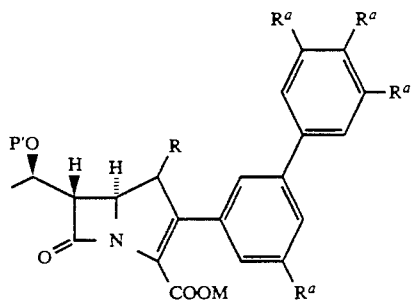

are useful intermediates to antibacterial agents.

4 Claims, No Drawings

2-BIPHENYL CARBAPENEM INTERMEDIATES

This is a continuation of application Ser. No. 594,886, filed Oct. 9, 1990, now abandoned.

BACKGROUND OF THE INVENTION

The present invention relates to antibacterial agents of the carbapenem class, in which the 2-position sidechain is characterized by a biphenyl moiety, substituted by various cationic and neutral substituents, as described in more detail further below.

Thienamycin was an early carbapenem antibacterial agent having a broad spectrum; it has the following formula:

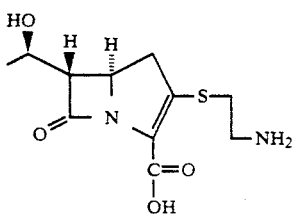

Later, N-formimidoyl thienamycin was discovered; it has the formula:

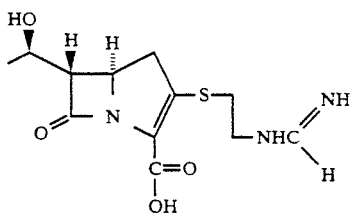

The 2-biphenyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

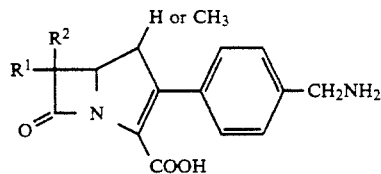

However, there is no description or suggestion of a biphenyl 2-substituent such as characterizes the compounds of the present invention, nor is there any suggestion of the suprisingly better anti-MRSA/MRCNS activity of the compounds of the present invention.

EP-A-0277 743 describes a particular class of compounds of the formula:

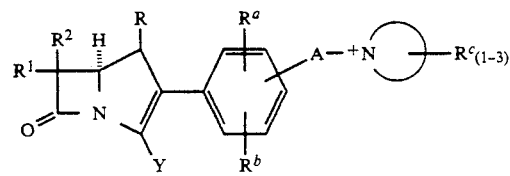

but this limited teaching in no way suggests the totally different compounds of the present invention, nor their surprisingly better anti-MRSA/MRCNS activity.

SUMMARY OF THE INVENTION

The present invention provides novel carbapenem compounds of the formula:

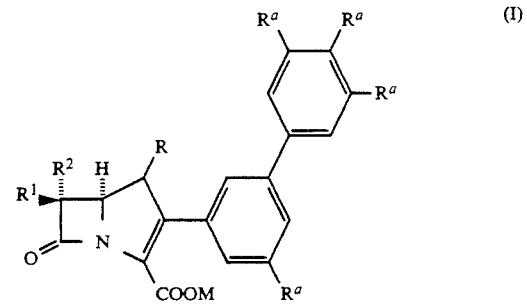

wherein

R is H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

$R^a$ are independently selected from the group consisting of hydrogen and the radicals set out below, provided that one but not more than one $R^a$ is selected from type I substituents:

I.

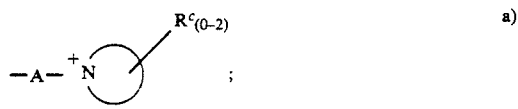

a)

where

A is $(CH_2)_m$—Q—$(CH_2)_n$, where m is 0 to 6 and n is 1 to 6 and Q is a covalent bond, O, S, SO, $SO_2$, NH, —SO$_2$NH—, —NHSO$_2$—, —CONH—, —NHCO—, —SO$_2$N(C$_1$-C$_4$alkyl)—, —N(C$_1$-C$_4$alkyl)SO$_2$—, —CON(C$_1$-C$_4$alkyl)—, —N(C$_1$-C$_4$alkyl)CO—, —CH=CH—, —CO—, —OC(O)—, —C(O)O— or N(C$_1$-C$_4$alkyl) and (CH$_2$)$_m$ is attached to the biphenyl moiety;

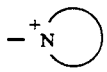

is a 5- or 6-membered monocyclic heterocycle or an 8-, 9- or 10-membered bicyclic heterocycle, the heterocycle containing a first nitrogen in an atomic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to form the optional second ring, with the the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

R$^c$ is R$^a$ as defined under II below, hydrogen, or —NR$^y$R$^z$ (where R$^y$ and R$^z$ are defined in II below), but independently selected from R$^a$ and from each other if more than one R$^c$ is present, and is attached to a carbon ring atom or a nitrogen heteroatom the valency of which is not satisfied by the ring bonds;

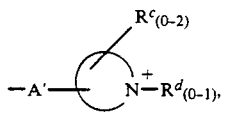   b)

where

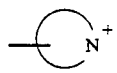

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent R$^d$ in addition to the ring bonds thereto, with said first nitrogen neutral in the absence of a substituent R$^d$, with attachment of the heterocycle to A' by way of a carbon atom of a ring, with the first ring containing 0 or 1 or either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 or 2 nitrogen atoms, and with the moiety being saturated or unsaturated and the second ring aromatic or non-aromatic;

R$^c$ is defined above;

R$^d$ is hydrogen, NH$_2$, O or C$_1$-C$_4$alkyl (where the alkyl group is optionally mono-substituted with R$^q$ as defined under IIc below);

A' is (CH$_2$)$_m$—Q—(CH$_2$)$_n$, where m is 0 to 6 and n is 0 to 6, Q is given above, and when m and n are 0 then Q is not a covalent bond;

   c)

R$^y$ and R$^z$ are as defined under II below,

R$^y$ and R$^z$ may further be together a C$_2$-C$_4$alkylidene radical to form a ring (optionally mono-substituted with R$^q$ as defined below) interrupted by N(O)R$^e$ or N$^+$(R$^e$)$_2$ (where R$^e$ is hydrogen, C$_1$-C$_4$alkyl or C$_1$-C$_4$alkyl monosubstituted with R$^q$ as defined below), R$^w$ is hydrogen, C$_{1-4}$ alkyl, O$^-$, NH$_2$ or absent in which case the N+ is neutral, R$^w$, R$^y$ and R$^z$ may further together form a C$_5$-C$_{10}$ tertiary alkylidene radical which with N+ forms a bicyclic ring, where the tertiary alkylidene radical is optionally mono-substituted with R$^q$ as defined below and where the tertiary carbon of the tertiary alkylidene radical is optionally replaced with nitrogen, N$^+$R$^e$ (where R$^e$ is defined above), or N$^+$—O$^-$, p is 0 or 1, and A is as defined above;

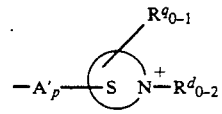   d)

where

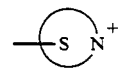

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents R$^d$ in addition to the ring bonds thereto, with the first nitrogen alternatively neutral by virtue of zero or one substituents R$^d$ in addition to the ring bonds thereto, with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), S(O)$_2$ and NR$^e$ where R$^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

R$^d$ is defined above and where more than one R$^d$ is present on a nitrogen, at least one R$^d$ is hydrogen or C$_1$-C$_4$alkyl;

A' is defined above; and p is defined above;

R$^q$ is defined below;

II.

a) a trifluoromethyl group: —$CF_3$;

b) a halogen atom: —Br, —Cl, —F, or —I;

c) $C_1$–$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —$C(O)NH_2$, —$OC(O)NH_2$, CHO, —$OC(O)N(CH_3)_2$, —$SO_2NH_2$, —$SO_2(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —O(C=O)$R^s$, where $R^s$ is $C_{1-4}$ alkyl or phenyl, each of which is optionally mono-substituted by $R^q$ as defined above;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —$S(O)_2$—, to form a ring (where the ring is optionally mono-substituted with $R_q$ as defined above);

g) a sulfur radical: —$S(O)_n$—$R^s$ where n=0–2, and $R^s$ is defined above;

h) a sulfamoyl group: —$SO_2N(R^y)R^z$ where $R^y$ and $R^z$ are as defined above;

i) azido: $N_3$ j) a formamido group: —N($R^t$)(C=O)H, where $R^t$ is H or $C_{1-4}$ alkyl, and the aryl thereof is optionally mono-substituted by $R^q$ as defined above;

k) a ($C_1$–$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above; l) a ($C_1$–$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N($R^t$)(C=O)N($R^y$)$R^z$ where $R^t$, $R^y$ and $R^z$ are as defined above;

n) a sulfonamido group: —N($R^t$)$SO_2R^s$, where $R^s$ and $R^t$ are as defined above;

o) a cyano group: —CN;

p) a formyl or acetalized formyl radical; —(C=O)H or —CH($OCH_3$)$_2$;

q) ($C_1$–$C_4$ alkyl) carbonyl radical wherein the carbonyl is acetalized: —C($OCH_3$)$_2C_{1-4}$ alkyl, where the alkyl is optionally mono-substituted by $R^q$ as defined above;

r) carbonyl radical: —(C=O)$R^s$, where $R^s$ is as defined above;

s) a hydroximinomethyl radical in which the oxygen or carbon atom is optionally substituted by a $C_1$–$C_4$ alkyl group: —(C=NO$R^z$)$R^y$ where $R^y$ and $R^z$ are as defined above, except they may not be joined together to form a ring;

t) a ($C_1$–$C_4$ alkoxy)carbonyl radical: —(C=O)O$C_{1-4}$ alkyl, where the alkyl is optionally mono-substituted by $R^q$ as defined above;

u) a carbamoyl radical: —(C=O)N($R^y$)$R^z$ where $R^y$ and $R^z$ are as defined above;

v) an N-hydroxycarbamoyl or N($C_1$–$C_4$ alkoxy)carbamoyl radical in which the nitrogen atom may be additionally substituted by a $C_1$–$C_4$ alkyl group: —(C=O)—N(O$R^y$)$R^z$ where $R^y$ and $R^z$ are as defined above, except they may not be joined together to form a ring;

w) a thiocarbamoyl group: —(C=S)N($R^y$)($R^z$) where $R^y$ and $R^z$ are as defined above;

x) carbonyl: —$COOM^b$, where $M^b$ is as defined above;

y) thiocyanate: —SCN;

z) trifluoromethylthio: —$SCF_3$;

aa) tetrazolyl, where the point of attachment is the carbon atom of the tetrazole ring and one of the nitrogen atoms is mono-substituted by hydrogen, an alkali metal or a $C_1$–$C_4$ alkyl optionally substituted by $R^q$ as defined above;

ab) an anionic function selected from the group consisting of: phosphono [P=O($OM^b$)$_2$]; alkylphosphono {P=O($OM^b$)—[O($C_1$–$C_4$ alkyl)]}; alkylphosphinyl [P=O($OM^b$)—($C_1$–$C_4$alkyl)]; phosphoramido [P=O($OM^b$)N($R^y$)$R^z$ and P=O($OM^b$)NH$R^x$]; sulfino ($SO_2M^b$); sulfo ($SO_3M^b$); acylsulfonamides selected from the structures CON$M^b$$SO_2R^x$, CON$M^b$$SO_2$N($R^y$)$R^z$, $SO_2$N$M^b$CON($R^y$)$R^z$; and $SO_2$N$M^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$–$C_7$ cycloalkyl group in which one of the carbon atoms in the ring is replaced by a heteroatom selected from O, S, NH or N($C_1$–$C_4$ alkyl) and in which one additional carbon atom may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$–$C_4$ alkenyl radical, optionally mono-substituted by one of the substituents a) to ac) above and phenyl which is optionally substituted by $R^q$ as defined above;

ae) $C_2$–$C_4$ alkynyl radical, optionally mono-substituted by one of the substituents a) to ac) above;

af) $C_1$–$C_4$ alkyl radical;

ag) $C_1$–$C_4$ alkyl mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from —S— and >N$R^t$ (where $R^t$ is as defined above) and one of the saturated carbon atoms of the oxazolidinone ring is optionally mono-substituted by one of the substituents a) to ag) above;

M is selected from:

i) hydrogen;

ii) a pharmaceutically acceptable esterifying group or removable carboxyl protecting group;

iii) an alkali metal or other pharmaceutically acceptable cation; or iv) a negative charge which is balanced by a positively charged group.

The present invention also provides novel carbapenem intermediates of the formula:

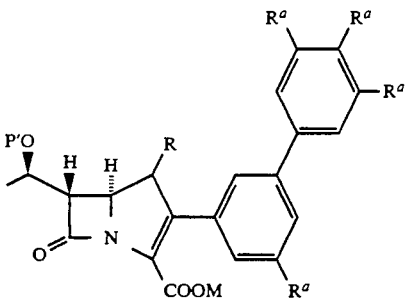

wherein:

R is H or CH$_3$;

R$^a$ is defined above, with the proviso that R$^q$ additionally includes OP' where P' is defined below, that M$^a$ and M$^b$ of R$^q$ both include M and that R$^a$ additionally may be protected hydroxyl, OP';

P' is a removable protecting group for hydroxy;

M is a removable protecting group for carboxy; and the Type I, R$^a$ substituent is balanced with the anionic form of Z where Z is methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

Preferred intermediates have the formula:

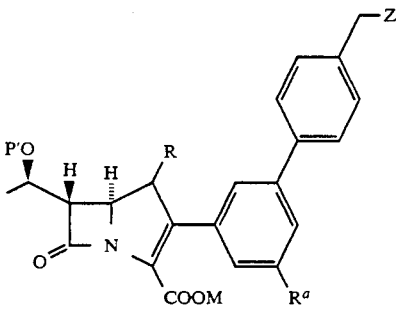

wherein

R is H or CH$_3$;

R$^a$ is selected from the group consisting of H, Cl, Br, I, SMe, CN, CHO, SOMe, SO$_2$Me and OP';

P' is a removable protecting group for hydroxy;

M is a removable protecting group for carboxy; and

Z is selected from the group consisting of alkyl and substituted alkylsulfonates, aryl and substituted arylsulfonates, and halides.

DETAILED DESCRIPTION OF THE INVENTION

The manufacture of compounds of Formula I may be carried out in a three-stage synthesis scheme followed by a final step which allows for the removal of any protecting groups. The objective of the first synthetic stage is to produce a base biphenyl compound which may be converted to the two-position substituent of the carbapenem of Formula I. The objective of the second synthetic stage is to attach the base biphenyl to the carbapenem. Finally, the objective of the third synthetic stage is to substitute the biphenyl with the desired R$^a$. This third synthesis stage may either be performed after the first synthetic stage or during or after the second synthetic stage according to the nature of the various R$^a$.

Flow Sheets AA through AF demonstrate suggested first stage syntheses. Flow Sheets B and C demonstrate two alternative second stage syntheses. The third synthesis varies according to the selected R$^q$.

The suggested first synthesis herein, Flow Sheets AA through AF, show preparation of various 3-bromo biphenyls each designated as B1 for use in either Flow Sheet B or C. In one instance an aryl stannane C3 is produced for use in Flow Sheet C. Following is a general description of the chemistry employed in each procedure.

AA: Synthesis of 3-bromo-5-substituted-biphenyls

A 3-bromo-5-substituted biphenyl intermediate is obtained by starting with a commercially available p-aminobiphenyl. The amino group serves to direct substitution to the two ortho positions (3 and 5), after which it can be removed reductively. However, in order to provide 5-substituted biphenyl compounds, the p-aminobiphenyl starting material AA1 as depicted in Flow Sheet AA is first protected by acetylation and then nitrated with nitrous acid before bromination is carried out.

Nitration is carried out with fuming nitric acid in the presence of acetic acid and acetic anhydride, after which deprotection is accomplished with sodium hydroxide using ethanol as a solvent and applying heat. These procedures are well known and are described in more detail, for example, in Dell'Erba et al., Tetrahedron, 27, 113 (1971).

Bromination is carried out in dioxane and water while the reaction mixture is maintained at near 0° C. with an ice-water bath. Aqueous 5N sodium hydroxide is added followed by bromine to produce compound AA2.

The original p-amino group is next removed by diazotization with sodium nitrite and concentrated sulfuric acid followed by reduction with powdered copper at ambient temperature to produce compound AA3.

The 5-nitro substituent is next converted to 5-amino group with stannous chloride dihydrate and this product then becomes the basis for obtaining a number of R$^a$ substituents on the meta-biphenyl moiety which characterize the compounds of the present invention. For example, the 5-fluoro compound can be obtained by thermal decomposition of the corresponding diazonium hexafluorophosphate salt, or the latter can be treated with potassium ethylxanthate to give the 5-ethylxanthylbiphenyl compound. This intermediate can then be the basis for obtaining the 5-methylthiobiphenyl compound of the present invention, or other unsubstituted and substituted alkyl mercaptans such as the 5-(2'-t-butyldimethylsilyloxyethylthio)biphenyl compound.

Returning to the diazotized 5-amino compound as a starting point for further synthesis, hydroxylation provides the 5-hydroxybiphenyl compound of the present invention, which can then be alkylated by treatment with sodium hydride followed by addition of an alkyl halide such as methyl iodide, to give the 5-alkoxy, e.g., 5-methoxybiphenyl compound of the present invention. The 5-hydroxy compound can also be protected by treatment with t-butyldimethysilyl chloride, creating an intermediate for synthesis of the desired hydroxybiphenyls of the present invention. The latter synthesis as the corresponding Grignard reagent or aryl stannane allow for a meta-biphenyl moiety when attached to the carbapenen nucleus.

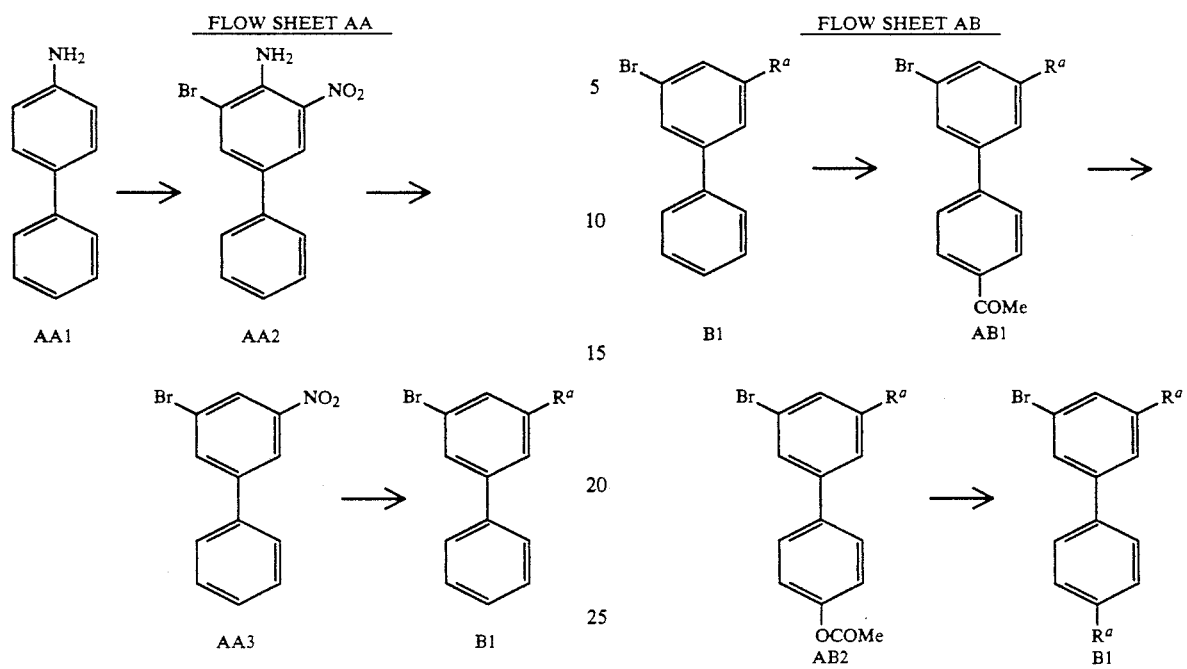

FLOW SHEET AA

AA1, AA2, AA3, B1

AB: Synthesis of 3-bromo-4',5-disubstituted-biphenyls

The 3-bromo-5-substituted biphenyls prepared in accordance with Flow Sheet AA above and also a simple 3-bromo biphenyl can be the starting point for introduction of a 4'-substituent in accordance with the following procedures. For example, the 4'-acetyl of the 3-bromo-5-fluoro compound can be made using the procedure of Berliner and Blommers, *JACS*, 73, 2479 (1951), after which treatment with m-chloroperoxybenzoic acid in refluxing 1,2-dichloroethane gives the 3-bromo-4'-acetoxy-5-fluoro compound. Both of these compounds are compounds of the present invention.

The 4'-acetoxy compound can be converted to the 4'-hydroxy compound by treatment with sodium methoxide, and then protected using t-butyldimethylsilyl chloride in accordance with procedures described above, said protected compound being useful in further synthesis.

The 4'-acetyl compound can also be the starting point for conversion to other 3-bromo-5-fluoro-4'-substituted biphenyl compounds of the present invention. For example, oxidation with sodium hypobromite, provides the 4'-carboxyl group, which can then be converted by borane reduction to the corresponding alcohol, both compounds of the present invention. The 4'-hydroxymethyl compound can then be protected with t-butyldimethylsilyl chloride as described above, for use as an intermediate in synthesis of other 3-bromo-5-fluoro-4'-substituted biphenyls.

The 4'-acetyl compound can also be converted to an amino group by a Beckmann rearrangement and hydrolysis which in turn can be diazotized to provide diazonium salts capable of producing other 4'-substituents in the same fashion as described above.

AC: Synthesis of 3-bromo-4',5',5-substituted-biphenyls

Starting with the 3-bromo-4'-amino intermediate prepared as described in connection with Flow Sheet AB above, it is possible to prepare compounds of the present invention in which the 5'-position is substituted. Once a 4'-N-acetamido group is in place, it can be used to direct substitution of a nitro group which can be converted to various substituents, forming compounds of the present invention, in the same manner as was described above under Flow Sheet AA.

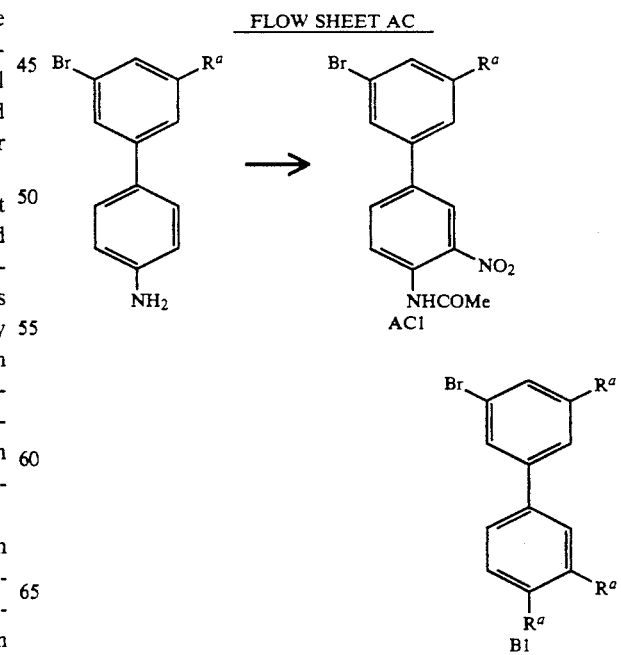

FLOW SHEET AC

AC1, B1

AD: Synthesis of 3-stannyl-3',4',5',5-substituted biphenyls

Starting with 3-bromo-4'-acetamido-5'-nitro intermediate, AC1, described above, it is possible to prepare biphenyl having 3', 4', 5' and 5 position substitution. Referring to Flow Sheet AD, intermediate AC1 is stannylated in a reaction with hexamethylditin in an aromatic hydrocarbon solvent, such as toluene or xylene, at elevated temperatures using tetrakistriphenylphosphinepalladium as a catalyst to produce intermediate AD1. Subsequently, the aryl stannane AD1 may be brominated in dioxane water at ambient temperatures or below to produce an aryl stannane AD2 with 3', 4', 5' and optional 5 position substitution. Each of these substituents, through subsequent art recognized procedures, may be replaced as desired to produce the aryl stannane C3, which may be employed in further synthesis of the carbapenems herein as according to Flow Sheet C below. Optionally, aryl stannane C3 may be converted to a Grignard Reagent analogous to B1.

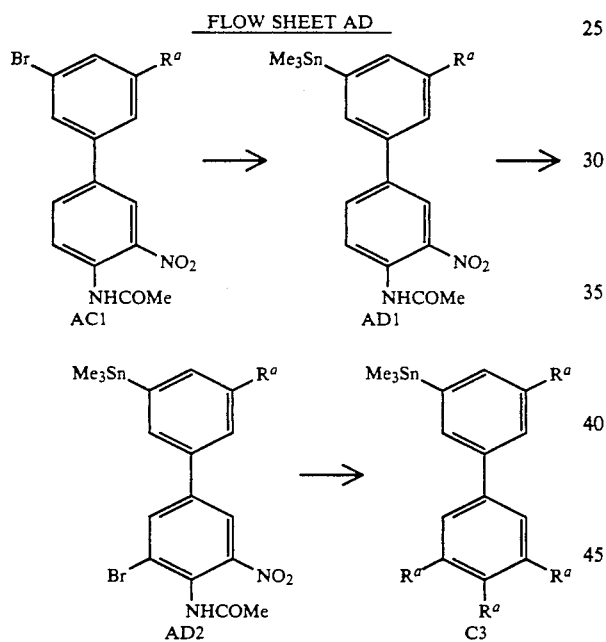

FLOW SHEET AD

AE: Synthesis of 3-bromo-3',4',5'-substituted-biphenyls

Starting with readily available starting materials, 1,3-dibromobenzene and the appropriately substituted iodobenzene, it is possible to prepare biphenyls having 3', 4' and 5' position substitution. Referring to Flow Sheet AE 1,3-dibromobenzene AE1 is converted to boronic acid AE2 by first reacting with butyl lithium in anhydrous THF or ether at about −78° C. followed by addition of triisopropyl borate. The resultant intermediate is worked up with sodium hydroxide and acidified. Boronic acid AE2 is subsequently reacted with the appropriate iodobenzene AE3 in toluene and aqueous sodium carbonate with tetrakistriphenylphosphinepalladium as a catalyst to produce the 3-bromo biphenyl B1. This reaction to B1 is well known in art with reference made herein to N. Miyaura, T. Yanagi and A. Suzuki, *Syn. Comm.*, 11, 513 (1981).

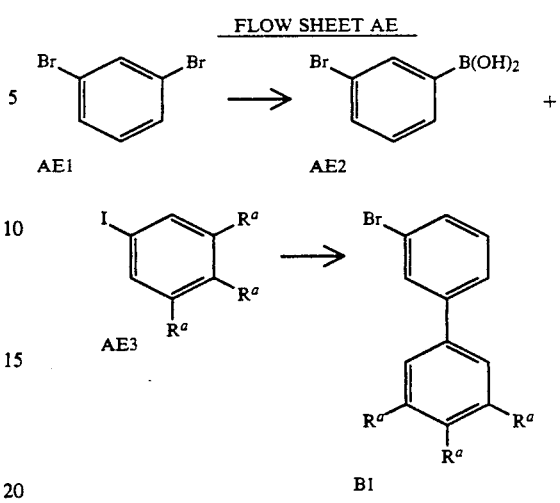

AE: Synthesis of 3-bromo-3',4',5'-substituted-biphenyls

Alternatively, starting with readily available starting materials, difluorosilylbenzenes and, as above, iodobenzenes, it is possible to prepare biphenyls having 3', 4' and 5' position substitution. Referring to Flow Sheet AF, meta-bromoethyldifluorosilylbenzene AF1 is reacted in DMF with iodobenzene derivative AF2 and a desilylating agent, KF, using diallylpalladium chloride catalyst at elevated temperatures to produce 3-bromo biphenyl B1. This reaction is known in the art with reference made herein to Y. Hatanaka, S. Fukushima and T. Hiyama, *Chem. Lett.*, 1711 (1989).

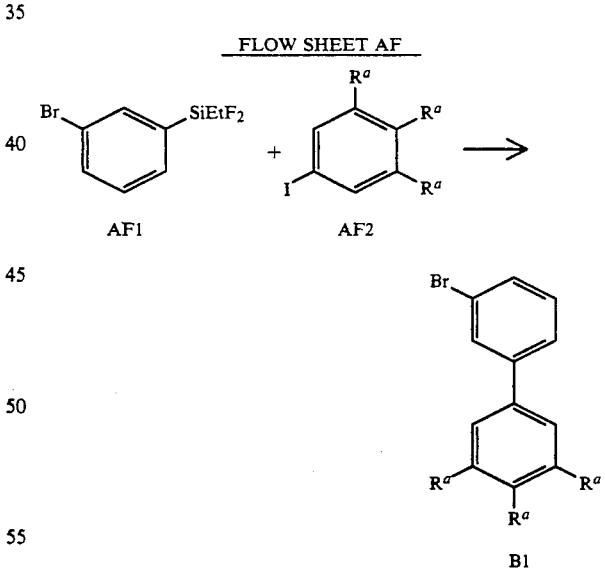

FLOW SHEET AF

All of the above synthetic schemes relate to preparation of biphenyl compounds substituted at various positions to be used in the formation of Grignard reagents or aryl stannanes, which, in turn, as shown below, are used to couple the already substituted biphenyl compounds to the carbapenem nucleus just prior to its formation (ring closure), or with a suitable activated intact carbapenem synthon. However, it is immediately clear to those skilled in the art that certain $R^a$ listed above, if substituted on B1 or C3 may not be compatible with the second stage synthesis. Thus, it is also possible, as an alternative synthetic scheme for preparation of the compounds of the present invention, to generate the desired substituents at the appropriate positions on the biphenyl nucleus after the biphenyl nucleus itself has already been attached to the carbapenem nucleus. More precisely, however, this is a process of modifying compatible precursor substituents already in place on the biphenyl nucleus so as to convert them to additional desired substituents.

The identity of the precursor substituent where employed on B1 or C3 is not crucial and the precursor substituent may itself be a protected or unprotected $R^a$. Preferably the precursor substituent is compatible to the synthesis to B1 or C3. An incompatible precursor substituent would obviously require additional synthesis to make. Critically it is required that the precursor substituent is compatible with the chemistry depicted in Flow Sheets B and C and may be converted to more desireable substitution. Preferred precursor substituents are methyl, hydroxymethyl and protected hydroxymethyl for Flow Sheet B.

Thus, as to the $R^a$ substituent on compound B1 or C1, it may be an $R^a$ with or without protecting groups, preferably it is stable to the conditions of producing compound B1 or C3 and it must be stable to the conditions of subsequently adding B1 or C3 to the carbapenem. Alternatively, it may be a precursor substituent which is optionally stable to the conditions of making B1 or C3, which is stable to the conditions of adding B1 or C3 to the carbapenem and which is convertible to a desired $R^a$ or to another precursor substituent.

As stated above, the second stage synthesis is to attach the base biphenyl to the 2-position of the carbapenem. With stable $R^a$ or suitable precursor substituents therefore, biphenyl B1 may be added to azetidin-2-one B2 in a Grignard reaction as shown in Flow Sheet B. The Grignard reaction requires that B1 be converted to a Grignard reagent by reaction with magnesium and 1,2-dibromoethane in THF from 20° C. to 60° C. and subsequently contacting B1 as a Grignard reagent with B2 in THF at from −70° C. to about 20° C. to produce azetidin-2-one B3. Alternatively, B1 may be reacted with t-butyllithium, n-butyllithium, or the like in THF at from −78° to −50° C. followed by the addition of magnesium bromide to produce the same Grignard reagent. $R^i$ of B3 is in practice pyrid-2-yl but may clearly be a variety of substituents including aromatic and heteroaromatic substituents. Further $R^i$ might be for example phenyl, pyrimidinyl or thiazolyl.

Azetidin-2-one B3 is an intermediate that may be ring closed to a carbapenem. It is on this intermediate that $R^a$ or precursor substituent for instance (t-butyldimethylsilyloxy)methyl may be modified where such modification is incompatible with the carbapenem nucleus. For example, a convenient reaction to remove a t-butyldimethylsilyl group of B3 is to expose it to a 2% dilute solution of sulfuric acid in methanol at 0° C. for from a few minutes to several hours. If the t-butyldimethylsilyl group was removed under the same conditions after cyclization of B3 to a carbapenem, a substantial portion of the carbapenem would be degraded and lost. Thus, modification of the precursor substituent in this instance and replacement with another precursor substituent or even $R^a$ is best performed before closing the carbapenem. Of course it is possible to remove a t-butyldimethylsilyl group in reduced yield after cyclization of B3 to a carbapenem by reaction with tetra-n-butylammonium fluoride and acetic acid in THF.

Compound B3 may be ring closed to carbapenem B4 by refluxing in xylene with a trace of p-hydroquinone for about 1 to 2 hours in an inert atmosphere. It is on this intermediate that final elaboration of $R^a$ from a precursor substituent, e.g. hydroxymethyl, may be accomplished. Removal of the carboxyl or hydroxyl protecting groups then provides the final compound Formula I. Such final elaboration and deprotection is described in further detail below.

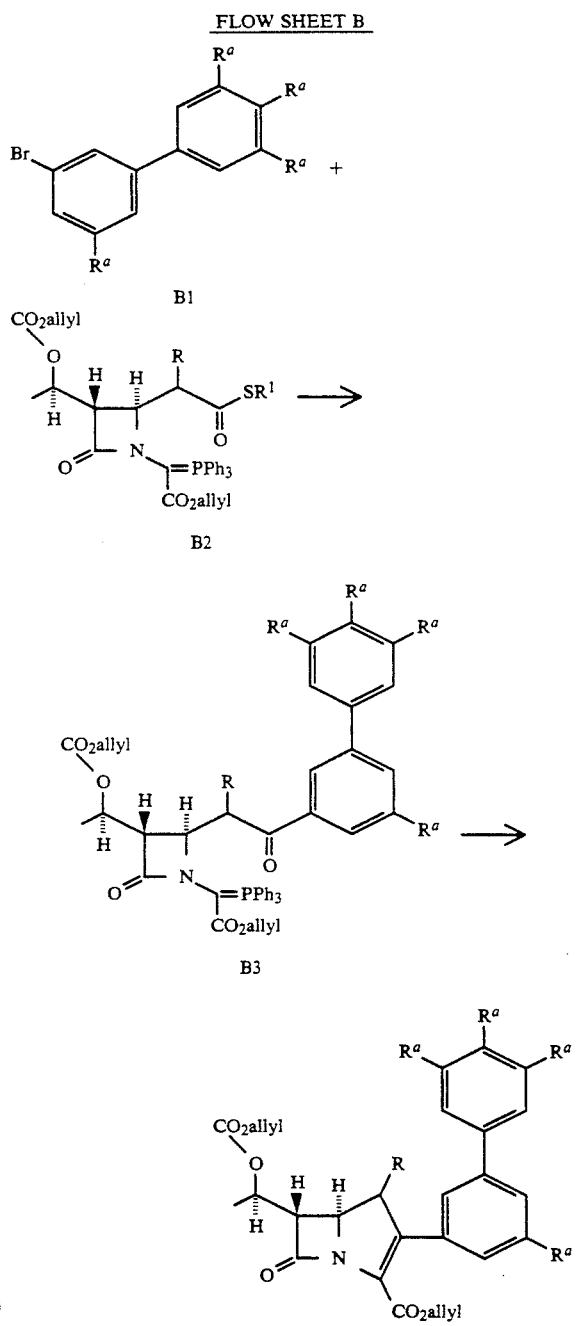

Flow Sheet C shows an alternative second stage synthesis, i.e. attachment of the base biphenyl such as B1 to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify bromobiphenyl B1 to the trimethylstannylbiphenyl C3. This is accomplished by reacting B1 with t-butyllithium in THF at from −78° to −50° C. followed by the addition of trimethyltin chloride. Alternatively, C3 may be prepared by simply heating B1 with hexamethylditin in the presence of tetrakistriphenylphosphinepalladium in toluene solution. At this intermediate it may be desireable to remove certain protecting groups if employed on a precursor substituent or $R^a$. For instance, a protecting group such as t-butyldimethylsilyl on a hydroxymethyl substituent may be removed by exposure to tetra-n-butylammonium fluoride in THF yielding a particular C3. If the t-butyldimethylsilyl group was removed from carbapenem C4 under the same conditions, a substantial portion of the carbapenem would be degraded and lost. Thus modification of the precursor substituent in this instance and replacement with another precursor substituent or even $R^a$ is best performed before attachment to the carbapenem. Referring again to Flow Sheet C, the 2-oxocarbapenem C1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran or methylene chloride. An organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate and the like, a suitably substituted phenylphosphine, such as tris(4-methoxyphenyl)phosphine, tris(2,4,6-trimethoxyphenyl)phosphine and the like, and the stannane C3. A metal halide, such as lithium chloride, zinc chloride and the like, is added and the reaction solution is allowed to warm and is stirred at a suitable temperature, such as 0° to 50° C., for a few minutes to 48 hours. The carbapenem C4 is obtained by conventional isolation/purification methodology known in the art.

Generally speaking, the milder conditions of the synthesis shown in Flow Sheet C allow for a wider range of functional groups $R^a$ to be present than the synthesis illustrated in Flow Sheet B. However, in certain cases it is advantageous for the $R^a$ substituent(s) of the stannane C3 to be introduced in a protected or precursory form. Final elaboration of $R^a$ from a precursor substituent, e.g. hydroxymethyl, may be accomplished on carbapenem intermediate C4. Removal of protecting groups then provides the final compound of Formula I. Such final elaboration and deprotection is described in further detail below.

FLOW SHEET C

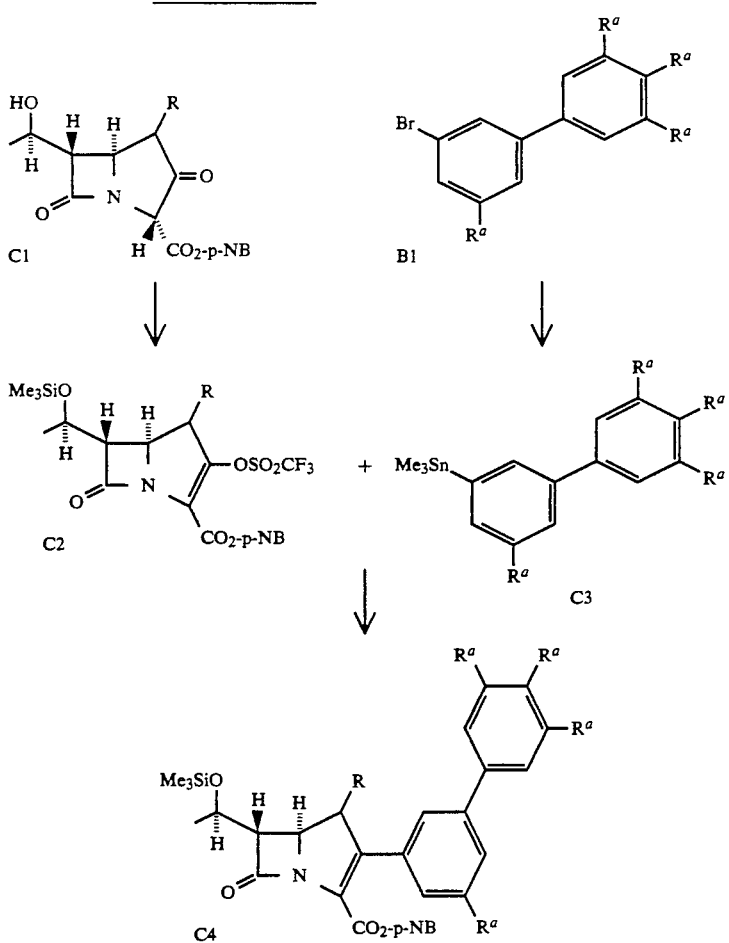

FLOW SHEET C

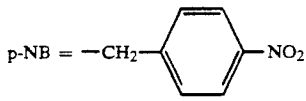

Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example, in U.S. Pat. Nos. 4,260,627 and 4,543,257; L. D. Cama et al. *Tetrahedron*, 39, 2531 (1983); R. N. Guthikonda et al. *J. Med. Chem.*, 30, 871 (1987) hereby incorporated by reference.

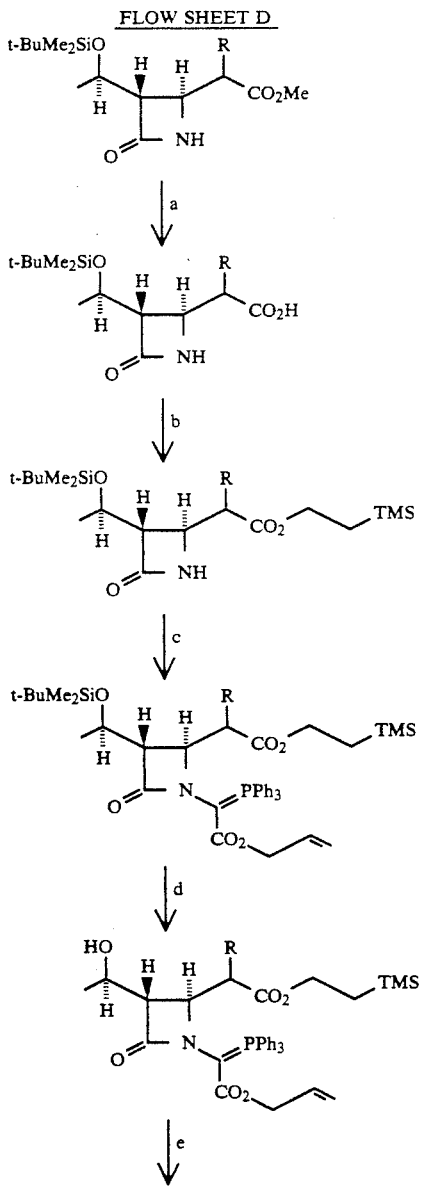

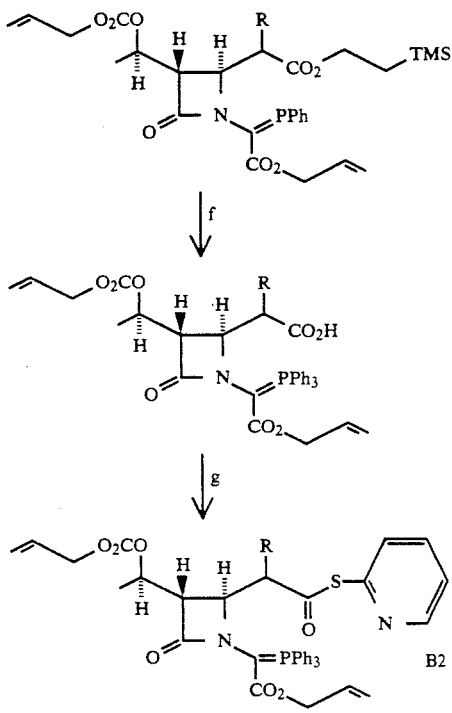

a. NaOH/MeOH
b. carbonyl diimidazole/
HO⟨⟩TMS c. i. OHCCO₂⟨⟩
   ii. SOCl₂
   iii. Ph₃P d. 6N HCl/MeOH e. ClCO₂⟨⟩/DMAP f. nBu₄NF
g. Pyr—SS—Pyr./Ph₃P The steps for preparing the 2-oxocarbapenam intermediate C1 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc. and hereby incorporated by reference.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanruku Ocean).

In the compounds of the present invention, one of the $R^a$ substituents must be of Type I. As a general matter, it is conjectured that anti-MSRA/MRCNS activity results from the configuration of the overall molecule uniquely conferred by the biphenyl nucleus. The Type I substituent provides still greater anti-MRSA/MRCNS activity to the molecule.

The Type II $R^a$ substituents are distinguishable from Type I substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I substituents with the optional Type II substituents, there can be obtained a combination of desired attributes in the final overall molecule not attainable with a single substituent, i.e., improved anti-MRSA/MRCNS activity together with enhanced water solubility.

Type I substituents employed in the compounds of the present invention may have quaternary nitrogen groups, and these include both cyclic and acyclic types, as is described under Type I. As already pointed out above, it is required that one, but no more than one, of the substituents $R^a$ must be a member selected from the group consisting of the definitions under Type I. It is optional that one, or at most three, of the remaining substituents may be a member selected from the group consisting of definitions under Type II. For example, $R^a$ at position 5- may be Type I and $R^a$ at position 4'- may be of Type II, while the remaining substituents are hydrogen.

In preferred compounds of Formula I, $R^1$ is hydrogen. More preferably, $R^1$ is hydrogen and $R^2$ is (R)—CH$_3$CH(OH)— or (R)—CH$_3$CH(F)—. In the most preferred case, $R^1$ is hydrogen and $R^2$ is (R)—CH$_3$CH(OH)— or (R)—CH$_3$CH(F)—. While R=H is usually preferred, there are instances in which R=CH$_3$ may provide improved chemical stability, water solubility, or pharmacokinetic behavior. The substituent R=CH$_3$ may be of either configuration, i.e., the $\alpha$ or $\beta$-stereoisomer. Additionally, in preferred compounds, $R^a$ in the 5-position of the biphenyl is other than hydrogen.

Preferred Type I. a) substituents include:

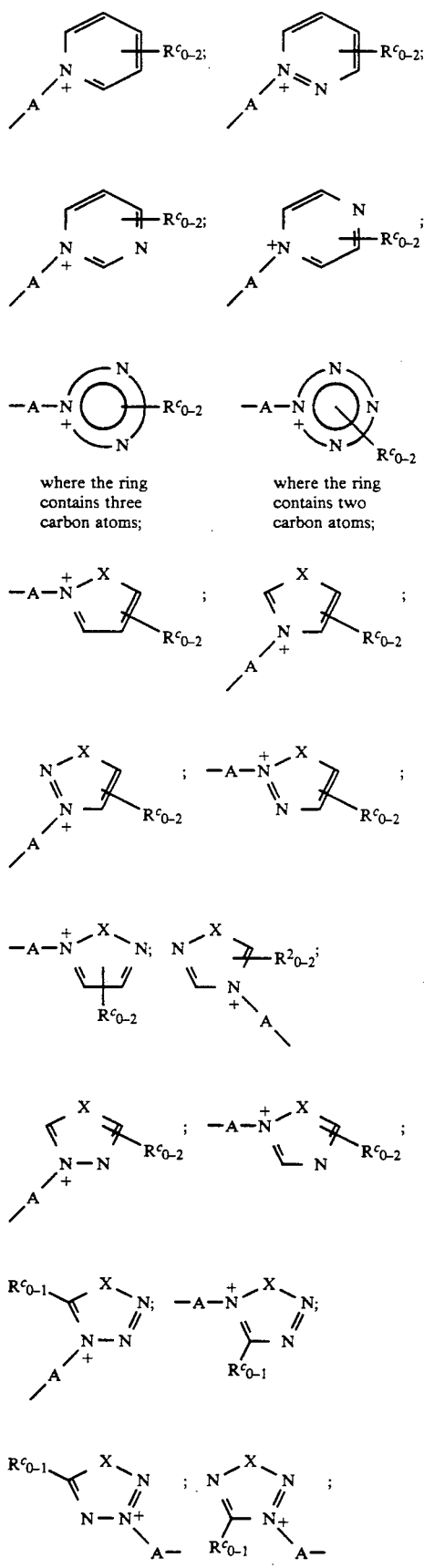

where the ring contains three carbon atoms;

where the ring contains two carbon atoms;

-continued
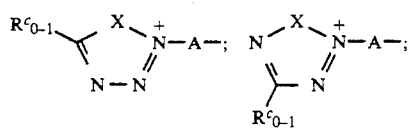
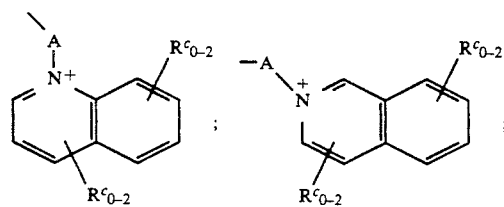
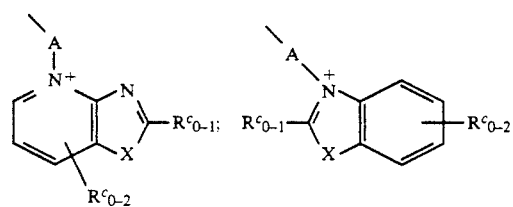
and
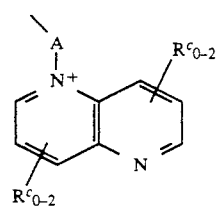
where X=O, S, or NR$^c$. For structures of Type I. a), where R$^c$ is shown to have an indefinite position, it maybe attached to any carbon of the ring.
Preferred type I.b) substituents include:
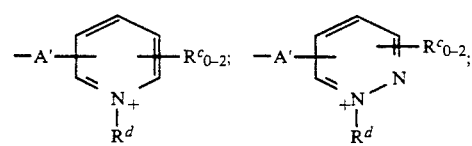
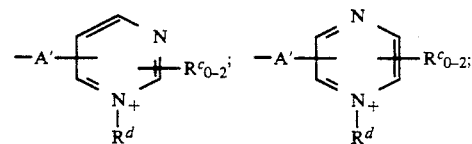
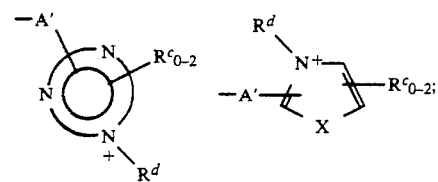
where the ring contains three carbon atoms;
-continued
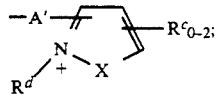
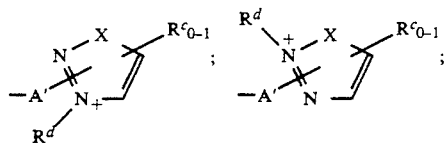
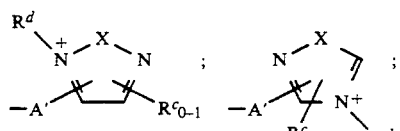
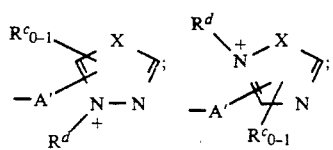
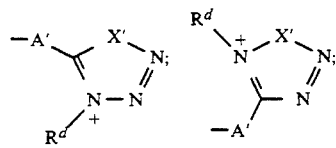
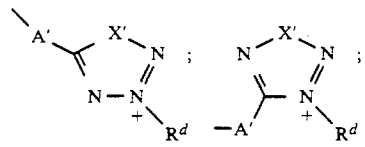
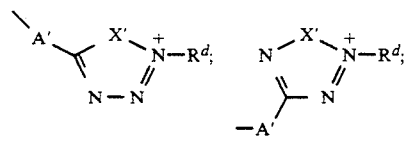
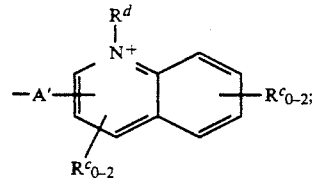
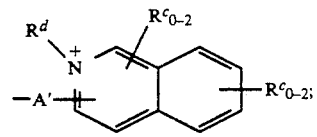
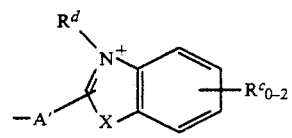
and -continued

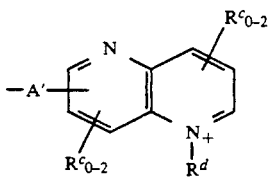

where X=O, S, or NR$^c$ and X'=O or S. For structures of Type I. b), where R$^c$ and/or A' are shown to have indefinite positions, they are independently attached to any carbon atom of the ring.

Preferred type I. c) substituents include:

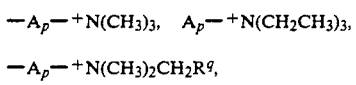

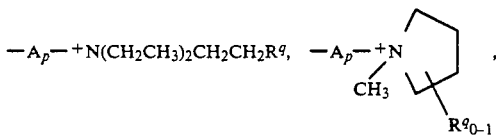

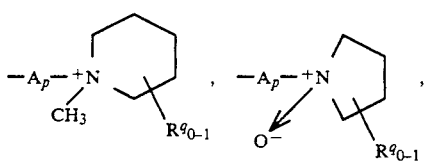

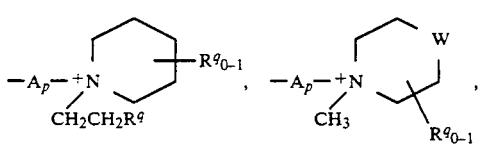

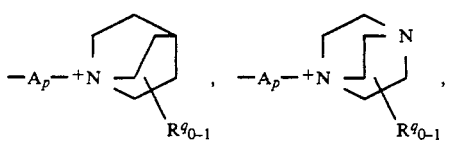

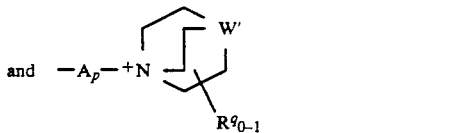

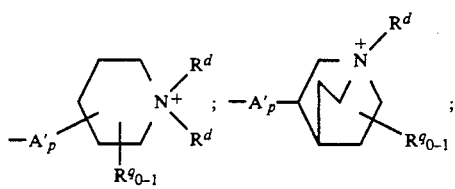

where W is O, S, NR$^e$, N(O)R$^e$, SO, SO$_2$ or N$^+$(R$^e$)$_2$ and W' is N$^+$R$^e$ or NO. For structures of type I.c), where R$^q$ is shown to have an indefinite position, it may be attached to any carbon atom of the ring.

Preferred type I. d) substituents include:

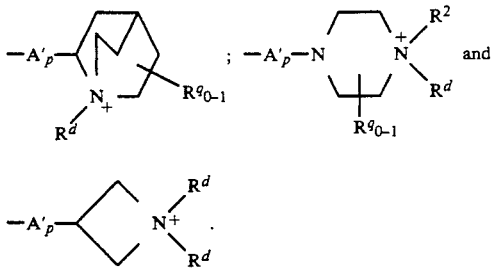

For structures of type I.d), where R$^q$ and/or A'$_p$ is shown to have an indefinite position, it may be attached to any carbon atom of the ring.

The R$^c$ substituents herein are intended to represent suitable further substituents on the type I. a) or b) substituents for the biphenyl ring. As seen above, these type I. a) or b) substituents are monocyclic or bicyclic aromatic groups containing heteroatoms. Given this class of primary substituent, further suitable substituents may be readily discovered in the penem and carbapenem art. For example, suitable substituents for type I. a) or b) substituents are generally taught in U.S. Pat. No. 4,729,993 assigned to Merck and Co. or in U.S. Pat. No. 4,746,736 assigned to Bristol-Myers Co. These patents are hereby incorporated by reference.

Broadly, R$^c$ may be the same or different and may be selected on an independent basis from the group as defined above. While a single such substitution is preferred, there is occasion to use up to two such substituents on an R$^a$, e.g., where it is desired to enhance the effect of a particular substituent group by employing multiple substituents. The particular choice of R$^c$ will depend upon the situation. For instance, a specific R$^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of R$^c$ herein includes two specific types of further substituent attached to the type I. a) or b) substituent. A first type of R$^c$ are those attached to a ring carbon and a second type of R$^c$ are those attached to a neutral ring nitrogen. Persons skilled in the art will readily recognize that a wide range of organic substituents are suitably used as R$^c$. Persons skilled in the art will also recognize that some substituents include the —NR$^y$R$^z$ substituents, useful for one purpose of R$^c$, i.e. carbon substitution, are not equally useful in the other, i.e. nitrogen substitution.

Preferred R$^c$ attached to ring carbon atoms are —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl) where M$^b$ is defined above. Preferred R$^c$ attached to neutral ring nitrogen atoms are —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, CH$_2$CH$_3$, CH$_2$CONH$_2$ and CN$_2$CON(C$_1$-C$_4$alkyl) where M$^b$ is defined above.

It is preferred that each type I. a) or b) substituent have no more than two R$^c$ substituents which are other than hydrogen. Thus, the formula shown above for type I. a) substituents has up to two $R^c$ substituents with the remainder of course being hydrogen. Further, the formula for the type I. b) substituent also allows up to two $R^c$. In accordance with these formulae, the previously listed more specific structures should be interrupted to have no more than two $R^c$ for each monocyclic or bicyclic group. Similarly for type I. c) or d) substituents it is preferred that any monocylic or bicyclic group have no more than a single $R^q$ substituent.

The scope of $R^d$ includes a single type of further substituent attached a type I. b) or d) substituent. The $R^d$ substituents are attached to a cationic nitrogen which may or may not be aromatic. Preferred $R^d$ attached to cationic nitrogen atoms are hydrogen, $-CH_3$, $CH_2CH_3$, $-CH_2CH_2CH_3$, $-CH_2COOM^b$, $-CH_2SO_3M^b$, $-NH_2$ and $O^{(-)}$, where $M^b$ is defined above.

The formulas depicting group Ib, Ic, or Id substituents show positively charged states for those substituents. It is understood that certain of those substituents, which are cationic by virtue of having a protonating hydrogen atom attached to the nitrogen, may also exist or be produced under certain conditions as a neutral substituent by virtue of the absence of such a hydrogen atom (i.e. in group Ib, when there is no $R^d$; in group Ic, when there is no $R^w$; and in group Id, when there is zero to one $R^d$, depending on type of heterocycle). Whether such a group Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no $R^d$ on a group Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral type Ib substituent may be in equilibrium with, and may also be represented by a formula showing, the corresponding compound containing the quaternized protonated substituent where $R^d$ is present and is a hydrogen atom. Furthermore the same compound may exist with the group Ib substituent in a completely protonated quaternized form, for instance in an aqueous solution in the presence of a stoichiometric amount of a strong mineral acid. It is intended herein that both the protonated (cationic) and the unprotonated (neutral) forms of group Ib, Ic and Id substituents of the type just described are within the scope of the present invention.

Suitable A spacer moieties include $-CH_2-$, $-CH_2CH_2-$, $-CH_2CH_2CH_2-$, $-CH_2CH_2CH_2-$, $-OCH_2CH_2-$, $-SOCH_2-$, $-SO_2CH_2-$, $-SCH_2CH_2-$, $-SOCH_2CH_2-$, $-SO_2CH_2CH_2-$, $-NHCH_2CH_2-$, $-N(CH_3)CH_2CH_2-$, $-CH_2N(CH_3)CH_2CH_2-$, $-CONHCH_2CH_2-$, $-SO_2NHCH_2CH_2-$, $-COCH_2-$, $-CH=CHCH_2-$ and $-CH_2OCH_2CH_2-$. Preferably, where Q is O, S, NH or $N(C_{1-4}alkyl)$, then n is 2-6.

Suitable A' are listed for A above. Further, A' may suitably be $-O-$, $-S-$, $-NH-$, $-SO_2-$, $-SO_2NH-$, $-CONH-$, $-CH=CH-$, $-CH_2S-$, $-CH_2NH-$, $-CONHCH_2-$ or $-SO_2NHCH_2-$.

The Type I. cationic substituents are generally added to the biphenyl following attachment of the biphenyl to the carbapenem. Conveniently, the biphenyl side-chain should be synthesized with a precursor substituent which may be elaborated into the desired cationic substituent. The identity of the precursor substituent will vary according to the particular $R^a$ desired. For example, one such precursor substituent is $-A-OH$, such as hydroxymethyl.

The hydroxymethyl precursor substituent may be elaborated into cationic substituents of Type I.a) by converting the hydroxyl into an active leaving group such as an iodine (giving $-A-I$) followed by reaction with a desired nitrogen containing aromatic compound. More particularly, two alternative procedures may be utilized to produce a leaving group on the moiety $-A-$ and subsequently to replace such a leaving group with cationic substituents of the type just described.

For a first procedure, the hydroxyl group of $-A-OH$ may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate which itself is a good leaving group may be converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desireable.

For a second procedure, the hydroxyl group of $-A-OH$ may be converted into the reactive trifluoromethanesulfonate (triflate) group. However, such an activating group may not be isolated by conventional techniques but can be formed and used in situ. Thus, treatment of the hydroxyl group with trifluoromethanesulfonic (triflic) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Introduction of the cationic group is then accomplished by reacting the above triflate in situ with the desired nitrogen containing compound at reduced temperature. In certain cases it is possible and desireable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

The above are representative of suitable leaving groups: alkyl and substituted alkylsulfonates, aryl and substituted arylsulfonates, and halide. The common sulfonate leaving groups are: methanesulfonyloxy, trifluoromethanesulfonyloxy, fluorosulfonyloxy, p-toluenesulfonyloxy, 2,4,6-tri-isopropylbenzenesulfonyloxy, p-bromobenzenesulfonyloxy and p-nitrobenzenesulfonyloxy. The preferred halo leaving groups are bromo and iodo. These alkyl and arylsulfonate leaving groups may be prepared using an analogous route to the one described above using the sulfonyl chloride or the sulfonic anhydride.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The type I.b) cationic substituents are prepared by quaternization of an aromatic ring nitrogen of a neutral precursor substituent on the biphenyl ring. Examples of neutral precursor substituents are —CONHCH$_2$—(2-pyridyl), —CONHCH$_2$—(4-pyridyl) or —SO$_2$CH$_2$—(4-pyridyl). Quaternization is accomplished by reacting the nitrogen compound in an inert organic solvent (e.g. CH$_2$Cl$_2$) at about 0° C. to room temperature with an alkylating agent $R^d$—Y where $R^d$ is given above and Y is a leaving group such as iodide, bromide, mesylate (methanesulfonate), tosylate (p-toluenesulfonate) or trifluoromethanesulfonate. Alternatively, the aromatic ring nitrogen may be quaternized by reaction with an oxidizing agent such as 3-chloroperbenzoic acid (giving the N-oxide) or an aminating agent such as o-(2,4,6-triisopropylbenzenesulfonyl)hydroxylamine (giving the N-amino derivative) in a suitable solvent (e.g. dichloromethane or CH$_3$CN) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem. The neutral precursor substituent may be already attached to the biphenyl ring at the time of its connection to the carbapenem, or it may be elaborated from a simpler precursor after connection to the carbapenem. An example of a precursor substituent for elaboration is —A'—OH such as hydroxymethyl. In one suggested synthesis, the hydroxyl may be converted to a reactive leaving group such as iodo as described above. The iodide is then reacted in a nucleophilic displacement reaction with an aromatic compound which has a nucleophilic side-chain substituent such as mercapto or amino. In this displacement reaction, it is the side-chain substituent that is the reacting nucleophile and not the aromatic ring nitrogen. Suitable substrates for this reaction include 2-(mercaptomethyl)pyridine, 2-aminopyridine, 2-(aminomethyl)pyridine or 4-(mercaptomethyl)-pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation of the aromatic ring nitrogen as described above then gives the type I.b) cationic substituent. A second suggested synthesis of a type I.b) cationic substituent starting from a precursor —A'—OH (e.g. hydroxymethyl) consists of oxidation of the alcohol functionallity to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from −70° C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane, and thiazolylmethylenetriphenylphosphorane. Quaternization or protonation as described above then completes the synthesis of the type I.b) cationic substituent. Depending on the particular $R^a$ of type I.b) that is desired, many other synthesis schemes may be employed, as would be apparent to an organic chemist skilled in the art.

The type I.c) cationic substituents may be prepared in an analogous manner to that described for I.a) substituents except that the nitrogen containing compound employed in the displacement reaction is an aliphatic amine (i.e. $NR^yR^zR^w$). However, in cases where the amino group is directly bonded to the biphenyl nucleus (i.e. —A$_p$N$^+$R$^y$R$^z$R$^w$ where p=0) the amine is most conveniently attached to the biphenyl prior to its incorporation into the carbapenem system. If such an amine is primary or secondary, it may require protection with a suitable amine protecting group during the steps employed to attach the biphenyl to the carbapenem. Tertiary amines require no protection and may be quaternized or protonated as described for the type I.b) cationic substituents.

The type I.d) cationic substituents are prepared by quaternization or protonation of a non-aromatic ring nitrogen of an appropriate neutral precursor substituent on the biphenyl ring. Quaternization or protonation is accomplished as described above for the type I.b) substituents. As with the type I.b) substituents, the neutral precursor may already be attached to the biphenyl ring at the time of its connection to the carbapenem, or the neutral precursor may be elaborated from a simpler precursor substituent on the biphenyl ring after its connection to the carbapenem. Examples of neutral precursor substituents are: —CONH(3-quinuclidinyl), —CONH[4-(N-methylpiperidinyl)], —SO$_2$CH$_2$CH$_2$[2-(N-methylpyrrolidinyl)], —SO$_2$NH[1-(4-methylpiperazinyl)] and —CH$_2$[1-(4-methylpiperazinyl)]. Elaboration of the neutral precursor substituent from a simpler substituent such as hydroxymethyl may be accomplished in an analogous manner to that described previously for the type I.b) substituents by employing appropriate reagents to introduce the type I.d) non-aromatic ring nitrogen moiety which is subsequently to be quaternized or protonated.

Among preferred $R^a$ of Type II are $C_{1-4}$ alkyl monosubstituted with hydroxy, such as, hydroxymethyl; formyl; carboxy, such as, —COOK; carbamoyl, such as, —CONH$_2$—; hydroxyiminomethyl, such as, —CH=NOH or cyano.

In regard to this preferred substitution, one or more hydroxymethyl groups may be obtained on the biphenyl ring as desired utilizing well known synthetic methods. For example, where the biphenyl is produced according to Flow Sheet AE, then a methyl group, as a precursor substituent, is substituted on starting materials AE1 and/or AE2 in the appropriate positions by well know means and the starting materials reacted to a corresponding B1. Subsequently, the methyl substituent of B1 may be oxidized e.g. to carboxylic acid group with chromium trioxide or to bromomethyl group with N-bromosuccinimide. This oxidation of the methyl, precursor substituent, can be advantageously performed prior to substituting the biphenyl on the azetidin-2-one as the oxidizing conditions maybe incompatible with either the azetidin-2-one or the subsequent carbapenem. The carboxylic acid group may be converted to hydroxymethyl group utilizing a reducing agent, such as, borane tetrahydrofuran complex and the bromomethyl group by conversion to acetoxymethyl group with potassium acetate followed by hydrolysis. As another example, where the biphenyl is produced according to Flow Sheets AA through AD, an amino substituent might be converted to a halogen which is then transformed to a carboxylic acid moiety and subsequently to hydroxymethyl group as described above and all by well known reactions.

The preferred formyl substitution on the biphenyl may be obtained from the hydroxymethyl substitution of B4 by a Swern oxidation. For example, isomeric B4 is oxidized in methylene chloride at from $-70°$ C. to room temperature employing triethylamine as the active agent and oxalyl chloride-dimethyl sulfoxide. Obviously, the position of the resultant formyl substitution will depend upon the position of the hydroxymethyl substitution in isomeric B4.

The preferred —CH=NOH substitution on the biphenyl may be conveniently obtained from the formyl substitution just described. This is accomplished simply by exposing the formyl substituted compound to hydroxylamine in an appropriate solvent at room temperature.

The preferred cyano substitution on the biphenyl may be obtained from the —CH=NOH substitution just described. The —CH=NOH substituted compound is dehydrated with triflic anhydride and triethylamine in a solvent at $-70°$ C.

The preferred —COOK substitution on the biphenyl may be obtained from the hydroxymethyl substituted B3 or isomeric B3 described above. For example, an isomeric B3 is oxidized with Jones reagent to convert the hydroxymethyl substituent to the carboxylic acid group. The oxidation with Jones reagent may be incompatible with the carbapenem and thus is optimally performed before ring closure. Prior to ring closure, the carboxylic acid group is protected as its allyl ester to permit cyclization of the carbapenem. Protection is carried out by alkylating with allyl bromide and triethylamine. Deprotection following cyclization is carried out in a palladium catalyzed reaction, in a solution containing potassium 2-ethylhexanoate as described in McCombie and Jeffrey, *J. Org. Chem.*, 47, 2505 (1983). Deprotection in such a solution yields the desired potassium salt.

The preferred carbamoyl, —CONH$_2$, may be obtained from B3 by oxidizing the hydroxymethyl group with Jones reagent to the corresponding carboxylic acid group as described above. This carboxylic acid substituent is converted to carboxamide group (—CONH$_2$) by sequentially contacting with 1-ethyl-3-(3-dimethyl-aminopropyl)carbodiimide hydrochloride, 1-hydroxybenzotriazole, and ammonia in an organic solvent at room temperature. Substituted amides may of course by obtained by replacing ammonia with the corresponding substituted amine. In contrast to the carboxyl substitution, this carbamoyl group requires no protection for the conditions of carbapenem cyclization.

Compounds substituted with the preferred $R^a$ of Type II just described may also be obtained by employing the synthesis shown in Flow Sheet C. In this case, the synthetic transformations just described may be carried-out on intermediate C3 prior to attachment to the biphenyl side-chain to the carbapenem or on C4 after such attachment.

In addition to or including the above, suitable $R^a$ of group II include:

| | |
|---|---|
| —OCH$_3$ | —OCH$_2$CO$_2$Na |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$H | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHOCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na | —SO$_2$CH$_2$CH$_2$OH and |
| | —CH$_2$I. |

In the preparation methods described above, the carboxyl group at the 3-position and the hydroxyl group at the 8-position of the carbapenem remain blocked by protecting groups until the penultimate product is prepared. Suitable hydroxyl protecting groups, P', are triorganosilyl groups such as trialkylsilyl, aryl(alkyl)silyl, and diarylalkylsilyl and carbonate groups such as alkyloxycarbonyl and substituted alkyloxycarbonyl, benzyloxycarbonyl and substituted benzyloxycarbonyl and allyloxycarbonyl and substituted allyloxycarbonyl. The preferred protecting groups are methoxy-t-butylphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to or including those shown in the schemes are described hereinbelow.

Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ and 10% Pd/C followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be $COO^-$. However, where M is, e.g., a pharmaceutically acceptable ester, a counterion (anion) $Z^-$ must be provided, or alternatively, an anionic substituent might be utilized. A counterion must also be provided or additional anionic substituent utilized where there is more than one quaternary nitrogen. Further, it is within the scope of this invention to utilize an anionic substituent where the quaternary nitrogen is already balanced by $COOM= COO^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tetra-alkylammonium group (e.g. tetramethylammonium, N-methylpyridinium), the cationic nitrogen atom in a protonated ammonium species (e.g. trimethylhydroammonium, N-hydropyridinium), the cationic nitrogen atom in an amine N-oxide (e.g. N-methylmorpholine-N-oxide, pyridine-N-oxide), and the cationic nitrogen atom in an N-amino-ammonium group (e.g. N-aminopyridinium).

The term "heteroatom" means N, S, or O, selected on an independent basis.

The term "heteroaryl" has been defined herein, in relation to the $R^x$ group, to have a specific and limited meaning, being only monocyclic. While the cationic groups I. a) and b) also clearly include heteroaryl groups, being both monocyclic and bicyclic, the term "heteroaryl" has not been used in association with the definitions of those cationic groups above. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1 N+1 O or 1 S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2 N's) and triazine (3 N's).

The heteroaryl groups of $R^x$ is always optionally mono-substituted by $R^q$, defined above, and substitution can be on one of the carbon atoms or one of the heteroatoms, although in the latter case certain substitutent choices may not be appropriate.

Listed in Table I are specific compounds of the instant invention:

TABLE I

| M | $R^a$ | $R^a$ Position |
|---|---|---|
| (−) | −CH₂N⁺—(pyridine)−NH₂ | 5 |
| (−) | −CH₂N⁺—(pyridine)−NH₂ | 5' |
| (−) | −CH₂N⁺—(pyridine)−NH₂ | 4' |
| (−) | −CH₂N⁺—(pyridine with NH₂) | 5 |
| (−) | −CH₂N⁺—(pyridine with NH₂) | 5' |
| (−) | −CH₂N⁺—(pyridine with NH₂) | 4' |
| (−) | −CH₂N⁺—(N—CH₃ ring) | 5 |
| (−) | −CH₂N⁺—(N—CH₃ ring) | 5' |
| (−) | −CH₂N⁺—(N—CH₃ ring) | 4' |

TABLE I-continued

[Structure: bicyclic β-lactam with hydroxyethyl group, N-C(COOM) and biphenyl substituent bearing R^a at 3', 4', 5' positions]

| | R^a | position |
|---|---|---|
| K | −CH₂N⁺(pyridinium)NCH₂SO₃⁻ | 4' |
| K | −CH₂N⁺(pyridinium)NCH₂CO₂⁻ | 4' |
| K | −CH₂N⁺(pyridine-4-CH₂CH₂SO₃⁻) | 4' |
| K | −CH₂N⁺(pyridine-3-CO₂⁻) | 4' |
| (−) | −CH₂N⁺(pyridinium)NCH₂CH₂OH | 4' |
| (−) | −CH₂N⁺(3-aminopyridinium) | 4' |
| (−) | −CH₂N⁺(pyridinium with CH₂S(O)CH₃ and NH₂ substituents) | 4' |
| (−) | −CH₂N⁺(4-CH₂OH-pyridinium) | 4' |
| (−) | −CH₂N⁺(3-CH₂OH, 5-NH₂ pyridinium) | 4' |
| (−) | −CH₂N⁺H(CH₃)₂ | 4' |
| (−) | −CO₂CH₂CH₂N⁺H(CH₃)₂ | 4' |
| (−) | −NHSO₂CH₂CH₂N⁺(imidazolium)N−CH₃ | 4' |
| (−) | −OCH₂CH₂N⁺(2-aminopyridinium) | 4' |
| (−) | −SCH₂CH₂N⁺(2-aminopyridinium) | 4' |
| (−) | −SO₂CH₂CH₂N⁺(2-aminopyridinium) | 4' |
| (−) | −CH₂OCH₂CH₂N⁺(2-aminopyridinium) | 4' |
| (−) | −CH₂SCH₂CH₂N⁺(2-aminopyridinium) | 4' |
| (−) | −CH₂S(O₂)N⁺(2-aminopyridinium) | 4' |
| (−) | −CH₂CH₂N⁺(2-aminopyridinium) | 5 |
| (−) | −C(O)CH₂N⁺(2-aminopyridinium) | 5 |

TABLE I-continued

Structure (columns 35 & 36): carbapenem core with 3-biphenyl substituent bearing $R^a$ groups at 3', 4', 5', and 5 positions; COOM at C-2.

| Stereo | $R^a$ group | Position |
|---|---|---|
| (−) | −S(O)(O)N(H)CH$_2$CH$_2$N$^+$(pyridine-2-NH$_2$) | 5 |
| (−) | −S(O)−CH$_2$CH$_2$−N$^+$(imidazole-N−CH$_3$) | 4' |
| (−) | −CCH$_2$−N$^+$(imidazole-N−CH$_3$), C=O | 4' |
| (−) | −S(O)(O)CH$_2$CH$_2$N$^+$(imidazole-NMe) | 4' |
| (−) | −CH$_2$S−(pyridinium-N$^+$-NH$_2$) | 5 |
| (−) | −CH=CH−(pyridinium-N$^+$-CH$_3$) | 5 |
| H | −NH−(pyridin-2-yl) | 5 |
| (−) | −C(=O)NH−CH$_2$−(pyridinium-N$^+$-CH$_3$) | 4' |
| (−) | −C(=O)NH−CH$_2$CH$_2$−(4-pyridinium-N$^+$-CH$_3$) | 4' |
| (−) | −S(O)(O)N(CH$_2$CH$_2$)$_2$N$^+$(CH$_3$)$_2$ | 4' |
| (−) | −S(O)(O)CH$_2$CH$_2$−(pyridinium-N$^+$-CH$_3$) | 4' |
| (−) | −CH$_2$−(pyridinium-N$^+$-CH$_3$, 2-NH$_2$) | 4' |
| (−) | −CH$_2$−(4-pyridinium-N$^+$-CH$_2$C(=O)NH$_2$) | 5 |
| K | −C(=O)NH−CH$_2$CH$_2$−(pyridinium-N$^+$-O$^-$) | 4' |
| K | −S(O)(O)CH$_2$−(4-pyridinium-N$^+$-O$^-$) | 4' |
| (−) | −C(=O)NH−(1-methyl-quinuclidinium) | 4' |
| (−) | −(N,N-dimethylpyrrolidinium) | 5 |
| (−) | −CH$_2$−N$^+$(CH$_3$)(morpholine) | 5 |
| (−) | −CH$_2$−N$^+$(CH$_3$)$_3$ | 5 |
| (−) | −CH$_2$−N$^+$(quinuclidine) | 5 |

TABLE I-continued

[Structure: carbapenem core with 3-biphenyl substituent bearing $R^a$ at 3', 4', 5' positions, H or CH₃ at C-5 position, and COOM group]

| M | $R^a$ | $R^a$ Position |
|---|---|---|
| K | —CH₂—N⁺(piperidine with CO₂⁻) | 5 |
| K | —CH₂—N⁺(morpholine N-oxide) | 5' |
| (−) | —CH₂—N⁺(bicyclic amine N-oxide) | 5 |
| (−) | —C(O)NH—CH₂—(piperidine N⁺(CH₃)₂) | 4' |

| M | $R^a$ | $R^a$ Position | $R^{a'}$ | $R^{a'}$ Position |
|---|---|---|---|---|
| (−) | CN | 5 | —CH₂N⁺=CH—NCH₃ (imidazolium) | 4' |
| (−) | SOCH₃ | 5 | —CH₂N⁺=CH—NCH₃ (imidazolium) | 4' |
| (−) | CO₂K | 4' | —CH₂N⁺=CH—NCH₃ (imidazolium) | 5 |
| (−) | CO₂K | 4' | —CH₂N⁺(pyridine-NH₂) | 5 |
| (−) | tetrazole-NK | 4' | —CH₂N⁺(pyridine-NH₂) | 5' |
| (−) | tetrazole-NK | 4' | —CH₂N⁺(pyridine-NH₂) | 5 |
| (−) | SO₃K | 4' | —CH₂N⁺(aniline-NH₂) | 5 |
| (−) | CO₂K | 4' | N⁺(pyrrolidine)CH₃ | 5 |
| (−) | SO₃K | 4' | —CH₂N⁺(pyrrolidine)CH₃ | 5' |
| (−) | SO₃K | 4' | —CH₂N⁺(pyrrolidine)CH₃ | 5 |
| (−) | CHO | 5 | —CH₂N⁺(pyridine-NH₂) | 4' |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethylsilyl or t-butyldiphenylsilyl, phenacyl, p-methoxybenzyl, acetonyl, o-nitrobenzyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility in medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 timer per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

Unless otherwise indicated, all of the temperatures in the working examples which follow are in degrees Celsius (°C.).

EXAMPLE 1

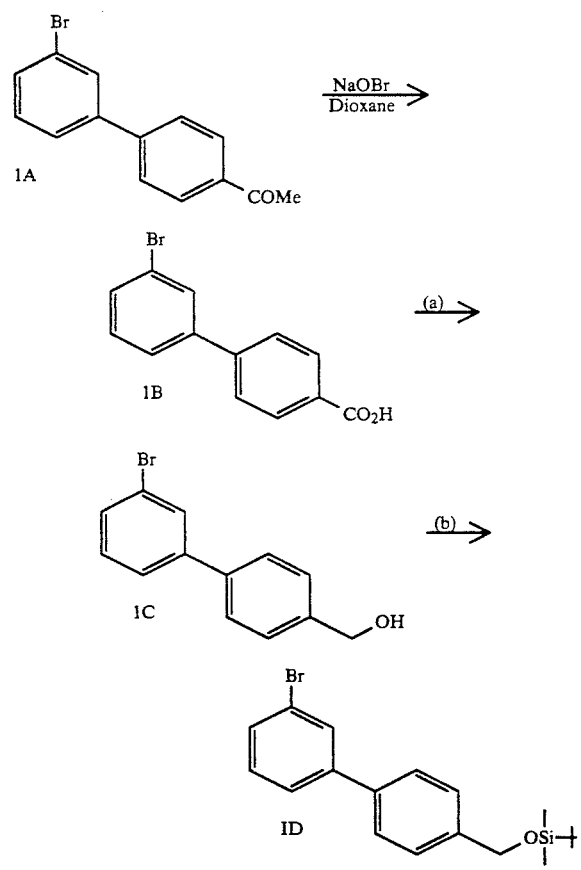

step (a)

To a stirred partial solution of 2.13 g (7.68 mmole) of carboxylic acid derivative 1B, prepared according to D. J. Byron, et al, *J. Chem. Soc.* (C), 840 (1966), in 40 cc of freshly distilled, dry THF at ambient temperature was added slowly and cautiously a solution of 1M borane-tetrahydrofuran complex in THF (15.4 mL, 15.4 mmole). The resulting mixture was stirred overnight at ambient temperature under an inert atmosphere of nitrogen and then carefully quenched with methanol. The solution was evaporated under reduced pressure and the residue dried in vacuo to give ca. 2 g (100%) of crude alcohol 1C which may be used without further purification.

Purification of 1C can be formed on silica gel utilizing $CH_2Cl_2$—$Et_2O$ (20:1) as the eluant; NMR ($CDCl_3$) δ: 4.74 (s, —$C\underline{H}_2O$—), 7.42–7.72 (m, 8Ar—$\underline{H}$).

step (b)

To a stirred solution of 2.3 g (8.9 mmole) of carbinol 1C from step (a) in 25 mL of sieve dried DMF at ambient temperature was added 1.35 g (13.4 mmole) of triethylamine and 2.02 g (13.4 mmole) of t-butyldimethylsilyl chloride. The resulting mixture was stirred at room temperature under an inert atmosphere of nitrogen for 1.5 hours. After this time, the mixture was partitioned between $Et_2O$/ice-$H_2O$/2N HCl and the organic phase was separated. It was washed twice with ice-$H_2O$ and then with a saturated solution of sodium chloride; dried with anhydrous sodium sulfate, filtered, and evaporated.

Purification by column chromatography on silica gel eluting with petroleum-ether (30°–60° C.) —$CH_2Cl_2$ (10:1) provided 3.16 g (94%) of product 3; NMR ($CDCl_3$) δ: 0.12 s, $Si(CH_3)_2$), 0.96 (s, $SiC(C\underline{H}_3)_3$, 4.78 (s, $OC\underline{H}_2$), 7.32–7.74 (m, $\overline{Ar}$—$\underline{H}$).

EXAMPLE 2

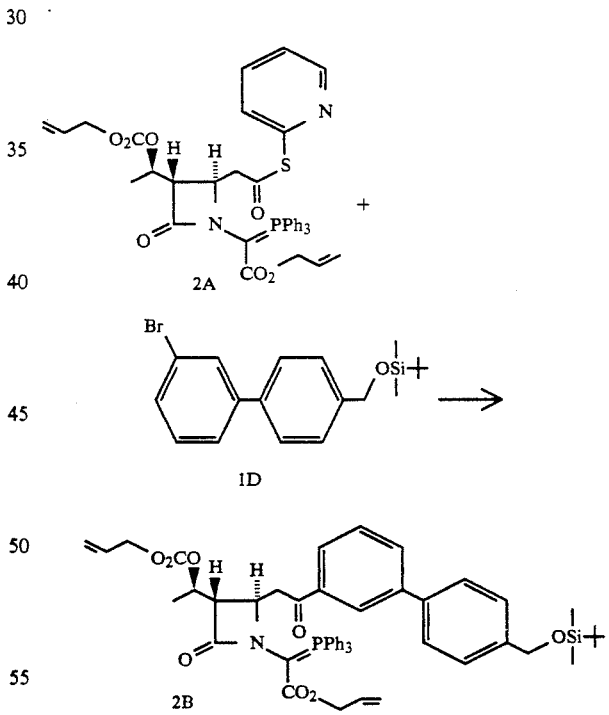

A stirred solution of 1D (562 mg, 1.49 mmole) in 5 mL freshly distilled, dry THF was treated with 54.5 mg (2.23 mmole) of magnesium turnings and 5 μl dibromoethane at ambient temperature in an inert atmosphere of nitrogen for 5.5 hours. This solution of the Grignard reagent was then added to a solution of pyridylthio ester derivative 2A (527.8 mg, 0.75 mmole) in 5 mL dry THF at 0° C. under a nitrogen atmosphere. The resulting mixture was stirred at 0° C. for 15 minutes and then partitioned between EtOAc/ice/1M $NH_4Cl$(aq.) and the organic phase separated. It was washed with ice- H₂O/5N NaOH and then saturated sodium chloride solution, dried with anhydrous sodium sulfate, filtered, and evaporated under reduced pressure.

Purification by plate layer chromatography (PLC) eluting with Et₂O gave 501.2 mg (75%) of 2B; IR(CH₂Cl₂) 1745, 1685, 1610 cm⁻¹.

EXAMPLE 3

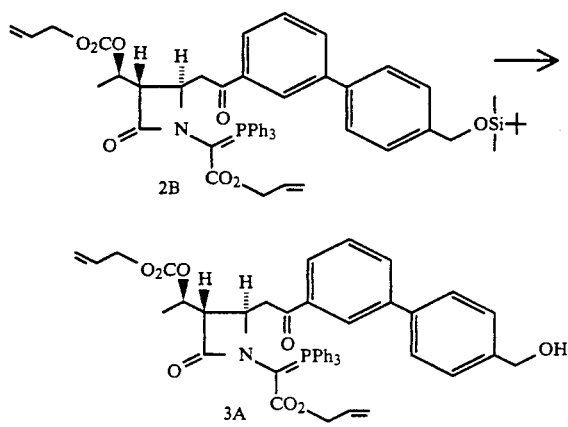

A mixture of 501.2 mg (0.56 mmole) of phosphorane 2B, prepared in Example 2, and 160 μL concentrated sulfuric acid in 8 mL of methanol was stirred magnetically at 0° C. in an inert atmosphere of nitrogen for 1.0 hour. After this time, the mixture was partitioned between EtOAc/ice-H₂O/satd. NaHCO₃ (aq.) solution and the organic phase was separated, washed with saturated sodium chloride solution, dried over sodium sulfate, filtered, evaporated, and dried in vacuo to give 443 mg (>100%) of crude product 3A, which could be used without further purification; IR(CH₂Cl₂) 1745, 1675, 1610 cm⁻¹.

EXAMPLE 4

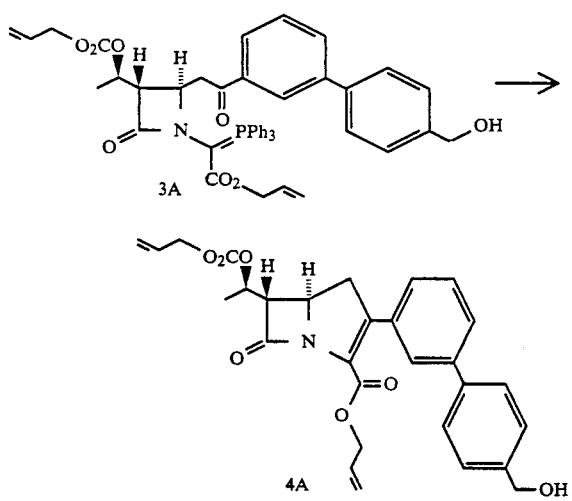

A stirred solution of crude phosphorane 3A (437.4 mg, 0.56 mmole), prepared in Example 3, in 30 mL of dry xylenes containing a crystal of hydroquinone was heated at 140° C. under an atmosphere of nitrogen for 84 minutes. After this time the mixture was let cool and then it was evaporated under reduced pressure.

Purification of the residue by PLC [one development CH₂Cl₂/EtOAc (5:1)] gave 190.5 mg (68%) of 4A as an oil; IR(CH₂Cl₂) 1770, 1750, 1725 cm⁻¹; NMR(CDCl₃) δ: 1.51 (d, CH₃), 3.25 (dd, 1-H-1), 3.47 (dd, 1-H-1), 3.45 (dd, 1-H-6), 4.31 (dt, 1-H-5), 4.76 (bs, 2H,—CH₂OH), 7.3–7.58 (m, 8—ArH); UV: $\lambda_{max}^{dioxane}$ 307 nm.

EXAMPLE 5

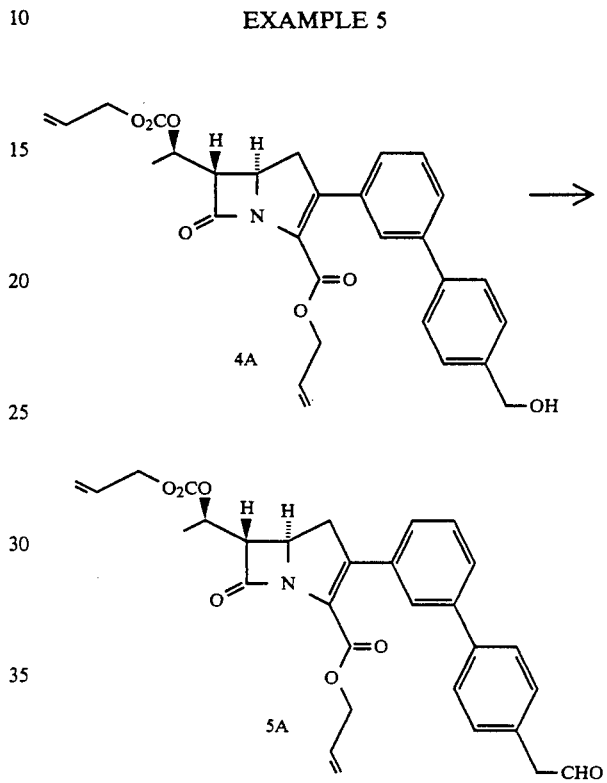

To a stirred solution of 19 μL (0.22 mmole) of oxalyl chloride in 1.5 ml anhydrous CH₂Cl₂ at −78° C. under a N₂ atmosphere was added 19.7 μL (0.27 mmole) of anhydrous DMSO. The resulting solution was stirred at −78° C. for 4 minutes and then a solution of 100 mg (0.20 mmole) of alcohol 4A in 1.0 mL anhydrous CH₂Cl₂ was added. The resulting yellow solution was stirred at −78° C. for 15 minutes and then 76 μL (0.55 mmole) of triethylamine was added. The resulting solution was stirred at −78° C. for 25 minutes and then partitioned between EtOAc and ice/2.0N aqueous HCl solution. The organic phase was separated, washed with brine, dried with anhydrous Na₂SO₄, filtered and concentrated under vacuum to provide 94.4 mg of aldehyde 8 as a yellow film; IR(CH₂Cl₂): 1780, 1745, 1720, 1700 cm⁻¹; 300 MHz ¹H-NMR(CDCl₃) δ: 1.50 (d, J=8.2 Hz, CH₃), 3.31 (m, 2-H-1), 3.45 (dd, J=2.8, 8.4 Hz, 1-H-6) 4.31 (td, 1-H-5), 4.67 (m, 1-H-8 and CH₂CH=CH₂), 5.29 (m, CH₂CH=CH₂), 5.90 (m, CH₂CH=CH₂), 7.37–7.98 (m, phenyl-H), 10.08 (s, —CHO).

EXAMPLE 6

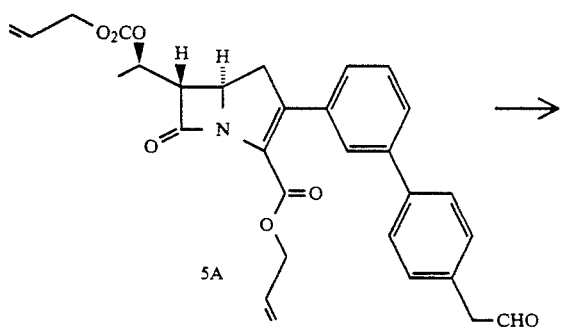

5A

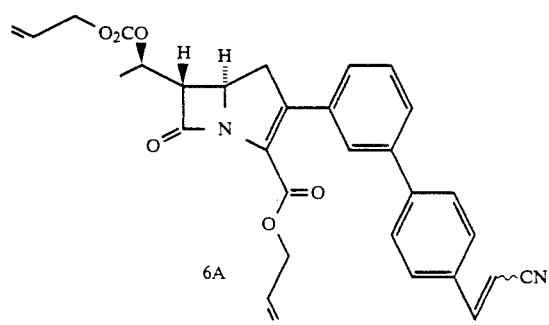

6A

To a stirred solution of 94.4 mg (0.19 mmole) of aldehyde 5A in 4 mL anhydrous acetonitrile at 0° C. under a N₂ atmosphere was added 102 mg (0.34 mmole) of cyanomethylene triphenylphosphorane. The resulting solution was stirred at room temperature for 3 hours and then concentrated under vacuum to provide a yellow film which was purified by PLC (2×1000μ 20×20 cm silica gel GF; 1:1, hexanes: EtOAc) to provide two products: trans 6A, 44.6 mg of a clear film; IR(CH₂Cl₂): 2210, 1780, 1745, 1720 cm$^{-1}$; 300 MHz NMR (CDCl₃) δ: 1.50 (d, J=6.2 Hz, CH₃), 3.30 (m, 2H-1), 3.44 (dd, J=2.9, 8.4 Hz, CHCHC=O), 4.32 (td, CHCHCH₂), 4.65 (m, 1H-8 and CH₂CH=CH₂), 5.30 (m, CH₂CH=CH₂), 5.87 (m, CH₂CH=CH₂), 5.92 (d, J=16.5 Hz, CH=CHCN), 7.27–7.63 (m, phenyl-H and CH=CHCN). UV: $\lambda_{max}^{dioxane}$ 309 nm; and cis 6A: 22.3 mg of a clear film; 300 MHz NMR (CDCl₃): δ: 5.48 (d, J=12.1 Hz, CH=CHCN), 7.68 (d, J=12.1 Hz, CH=CHCN).

EXAMPLE 7

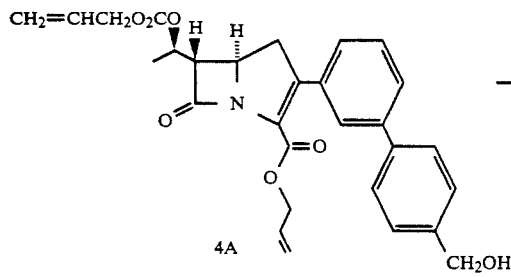

4A

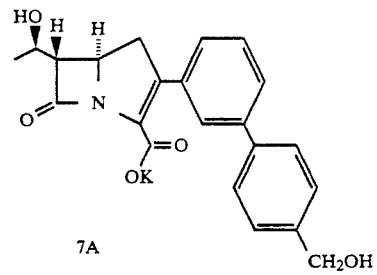

7A

To a stirred solution of 100.6 mg (0.2 mmole) of 4A in 6 mL of CH₂Cl₂-EtOAc (1:1) at ambient temperature was added 31.5 mg (0.12 mmole) of triphenylphosphine, 46.2 mg (0.04 mmole) of tetrakistriphenylphosphine palladium, 31.7 mg (0.22 mmole) 2-ethylhexanoic acid, and 440 μL of 0.5M potassium 2-ethylhexanoate in EtOAc (0.22 mmole). The resulting mixture was stirred at ambient temperature under a nitrogen atmosphere for 2.5 hours. The separated product was triturated with 8 mL of Et₂OAc (1:1) and collected by centrifugation and decantation of the supernatant. The solid was washed similarly with 10 mL Et₂O and dried to give 109.4 mg of crude product.

Purified by reverse phase-plate layer chromotography on two-1000μ plates [one development H₂O-MeCN (5:1)] to give after extraction with MeCN-H₂O (4:1) and lyophilization 37.6 mg (45%) of 7A; IR (Nujol) 1750 and 1595 cm$^{-1}$; NMR (D₂O) δ: 1.32 (d, Me), 3.12 (dd, 1-H-1), 3.48 (app dd, 1-H-1), 3.54 (app dd, 1-H-6), 4.34 (m, H-5 and H-8), 4.72 (s, 2H), 7.6 (m, 8-Ar-H); UV: $\lambda_{max}^{H_2O}$ 297 nm, 257 nm.

EXAMPLE 8

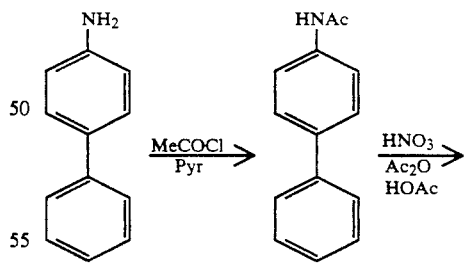

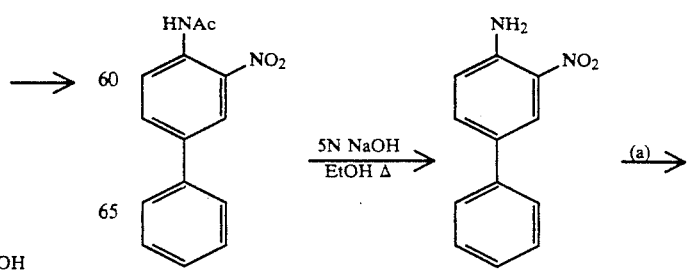

-continued

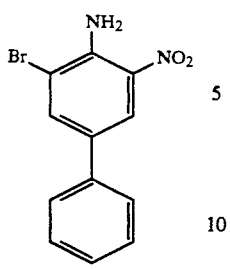

step (a)
To a stirred solution of 3-nitro-4-amino-biphenyl (13.85 g, 64.7 mmole) [prepared according to a the procedures described in C. Dell'Erba, G. Garbarino, and G. Guanti, Tetrahedron, 27, 113 (1971).] in 230 mL dioxane and 77 mL H$_2$O cooled in an ice-H$_2$O bath was added sequentially 12.9 mL 5N NaOH (aq.) (64.7 mmole) and then dropwise 12.41 g (77.7 mmole) bromine. When the addition was complete, the ice-H$_2$O bath was removed, and the mixture stirred further for 2 hours. After this time, the mixture was concentrated under high vacuum, H$_2$O added, and the insoluble material collected by suction filtration and washed with H$_2$O. The solid was dried in vacuo to give 19.6 g of crude product.

Recrystallization from MeOH—CH$_2$Cl$_2$—pet.ether gave only 8.78 g (46.5%) of 3-bromo-4-amino-5-nitro-biphenyl; NMR (CDCl$_3$) δ: 6.65 (bs, 2 NH), 7.44 (m, 5 AR-H), 7.98 (d, 1-Ar-H), and 8.38 (d, 1-Ar-H).

Chromatography on silica gel of the mother liquors using CH$_2$Cl$_2$—pet.ether (1:1) as eluant gave an additional 7.6 g of product for a combined yield of 86.7%.

EXAMPLE 9

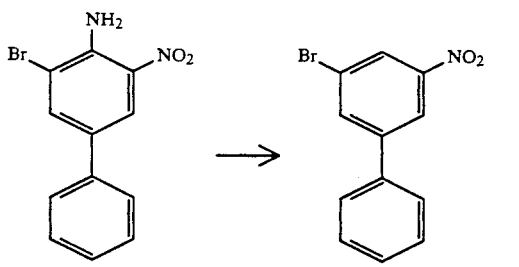

To a stirred solution of 759 mg (11 mmole) of sodium nitrate in 15 mL concentrated sulfuric acid chilled in an ice-H$_2$O bath was added a solution of 2.92 g (10 mmole) of biphenylamine derivative from Example 9 in 30 mL hot glacial HOAc. The resulting mixture was stirred at ice-H$_2$O bath temperature for 20 minutes.

The ice-H$_2$O bath was removed, 1.27 g (20 mmole) copper powder added, and the mixture stirred further for 2 hours. The insolubles were removed by suction filtration through a preformed pad of celite and washed with Et$_2$O. The filtrate was partitioned between Et$_2$O/ice-H$_2$O/5N NaOH and the organic phase was separated, washed with saturated NaCl solution, dried Na$_2$SO$_4$, filtered, and evaporated.

The residue was purified by chromatography on 50 grams of EM-60 silica gel eluted with petroleum ether-CH$_2$Cl$_2$ (2:1) to give 2.2 g (80%) of 3-bromo-5-nitro-biphenyl; NMR (CDCl$_3$) δ: 7.54 (m, 5 Ar-H), 8.05 (d, 1 Ar-H). 8.34 (d, 1 Ar-H), and 8.38 (d, 1 Ar-H).

EXAMPLE 10

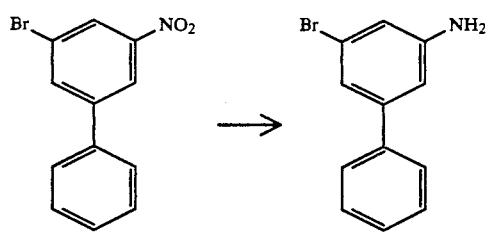

A stirred mixture of 7.62 g (27.5 mmole) of 3-bromo-5-nitrobiphenyl and 18.62 g (82.5 mmol) of stannous chloride dihydrate in 150 mL of absolute ethanol was refluxed under a nitrogen atmosphere for 1.5 hours. After this time, the mixture was concentrated and partitioned between Et$_2$O/ice/5N NaOH. The organic phase was separated, washed with saturated NaCl solution, dried over Na$_2$SO$_4$, filtered, and evaporated.

The product was purified by chromatography on silica gel with CH$_2$Cl$_2$-petroleum ether (1:1) to give 5.9 g (87%) of 3-bromo-5 aminobiphenyl; NMR (CDCl$_3$) δ: 3.89 (bs 2NH), 6.82 (m, 1Ar-H), 7.15 (t, 1Ar-H), 7.48 (m, 6Ar-H).

EXAMPLE 11

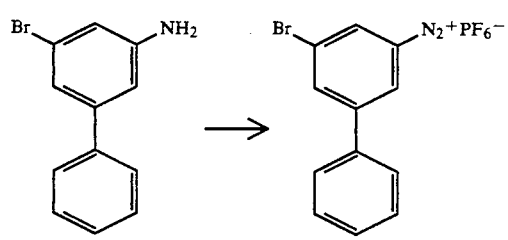

To a stirred solution of 1.08 g (15.6 mmole) of NaNO$_2$ in 10 mL conc. H$_2$SO$_4$ cooled in an ice-H$_2$O bath was added dropwise a solution of 3.67 g (14.9 mmole) of 3-bromo-4-aminophenyl in 40 mL HOAc. When the addition was complete, the mixture was stirred further for 10 minutes at 0° C., and then 4.0 g (21.7 mmole) of KPF$_6$ in 43 mL H$_2$O was added. The resulting mixture was stirred cold for 10 minutes and the separated product collected by suction filtration; washed well with cold H$_2$O and then with 80 mL Et$_2$O-MeOH (4:1); dried in vacuo overnight to give 5.87 g (97%) of diazonium hexafluorophosphate derivative; mp 157° C. (dec); IR (Nujol) 2295 cm$^{-1}$; NMR (d$_6$-DMSO) δ: 7.66 (m, 3Ar-H), 7.88 (m, 2Ar-H), 8.88 (m, 1Ar-H), 9.0 (m, 1Ar-H), and 9.16 (m, 1Ar-H).

EXAMPLE 12

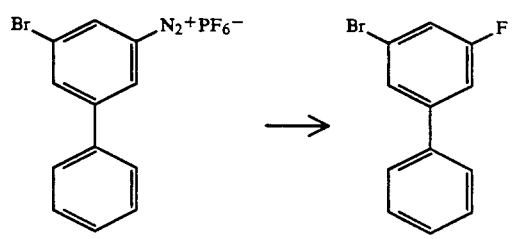

A stirred suspension of 4.04 g (10 mmole) of diazonium salt in 40 mL decane under a nitrogen atmosphere was immersed in a 170° C. oil bath for 10 minutes. The mixture was allowed to cool and then filtered through celite and washed with Et₂O. The filtrate was partitioned between Et₂O/ice-H₂O/saturated NaHCO₃(aq.) solution and the organic phase separated, washed with saturated NaCl solution, dried over Na₂SO₄, filtered, and evaporated.

The residue was purified by chromatography on silica gel with petroleum ether solvent to give 2.51 g (100%) of 3-bromo-5-fluorobiphenyl; NMR (CDCl₃) δ: 7.2 (m, 2Ar-H) and 7.48 (m, 6Ar-$\underline{H}$); MS: m/e 252, 250 (M+).

EXAMPLE 13

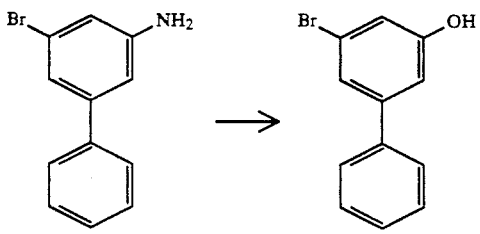

As previously described in Example 12, 1.24 g (5 mmole) of 3-bromo-5-aminobiphenyl was diazotized with 380 mg (5.5 mmole) of NaNO₂ in 4 mL conc. H₂SO₄ and 10 mL HOAc. The the stirred mixture was added 10 mL H₂O and it was heated to 70° C. under a nitrogen atmosphere for 1.25 hours.

The cooled mixture was partitioned between Et₂O-H₂O, and the organic phase separated, washed with H₂O (2×), then ice/saturated, NaHCO₃(aq.) solution and saturated NaCl solution; dried over Na₂SO₄, filtered and evaporated.

The residue was purified by column chromatography on silica gel with CH₂Cl₂-petroleum ether (1:1) and CH₂Cl₂-petroleum ether (3:1) to provide 995 mg (80%) of 3-bromo-5-hydroxy-biphenyl; NMR (CDCl₃) δ: 5.32 (bs, O$\underline{H}$), 7.02 (m, Ar-H) and 7.4 (m, Ar-H).

EXAMPLE 14

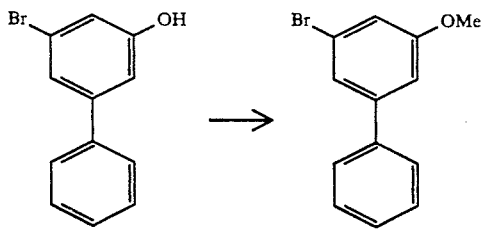

To a stirred solution of 995 mg (4 mmole) of 3-bromo-4-hydroxybiphenyl in 10 mL sieve dried DMF at ambient temperature was added 173.3 mg (4.4 mmole) of 61.1% mineral oil dispersion of NaH. The resulting mixture was stirred at room temperature under a nitrogen atmosphere for 10 minutes and 1.71 g (12 mmole) of neat MeI was added. The mixture was stirred further at ambient temperature for 0.5 hour.

The mixture was poured onto ice-H₂O and extracted with Et₂O. The extract was washed with ice-H₂O (2×), and then saturated NaCl solution; dried over Na₂SO₄, filtered, and evaporated.

The residue was purified by silica gel chromatography with petroleum ether solvent to give 842 mg (80%) of 3-bromo-5-methoxybiphenyl; NMR (CDCl₃) δ: 3.87 (s, OC$\underline{H}$₃), 7.07 (m, 2Ar-H), 7.48 (m, 6Ar-H).

EXAMPLE 15

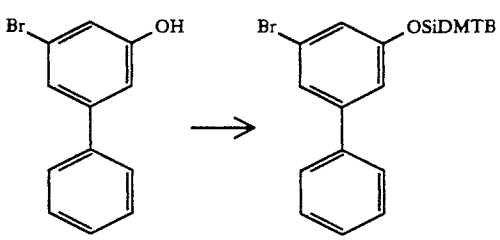

To a stirred solution of 372 mg (1.5 mmole) of 3-bromo-5-hydroxybiphenyl and 339.1 mg (2.25 mmole) of t-butyldimethylsilyl chloride in 4 mL sieve dried DMF at ambient temperature under a nitrogen atmosphere was added 227.7 mg (2.25 mmole) of triethylamine. The resulting mixture was stirred further for 1.75 hours.

The mixture was partitioned between Et₂O/ice-H₂O/2N HCl (aq.) and the organic phase separated, washed with ice-H₂O (3×), and saturated NaCl solution, dried over NaSO₄, filtered, and evaporated.

The residue was purified by PLC [1 development petroleum ether] to give 500 mg (92%) of 3-bromo-5-t-butyldimethylsilyloxybiphenyl; NMR (CDCl₃) δ: 0.14 (s, Si(CH₃)₂), 1.0 (s, SiC(C$\underline{H}$₃)₃), 6.98 (m, Ar-$\underline{H}$), and 7.44 (m, Ar-$\underline{H}$).

EXAMPLE 16

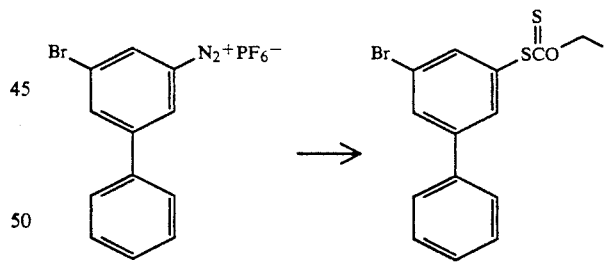

To a stirred solution of 11.1 g (69,4 mmole) of potassium ethylxanthate in 120 mL acetone at 0° C. under a nitrogen atmosphere was added all at once 20 g (49.4 mmoles) of biphenyldiazonium salt from Example 11. The mixture was stirred 1.3 hours at 0° C. and 0.75 hours at ambient temperature. The mixture was partitioned between Et₂O/ice-H₂O and the organic phase was separated, washed with brine, and dried over Na-SO₄/MgSO₄, filtered, and evaporated to a brown oil. The residue was purified by silica gel chromatography to give 3.5 g of pure 3-bromo-5-ethylxanthylbiphenyl; NMR (CDCl₃) δ: 1.36 (t, C$\underline{H}$₃), 4.62 (q, OC$\underline{H}$₂), 7.3–7.7 (m, Ar-H).

EXAMPLE 17

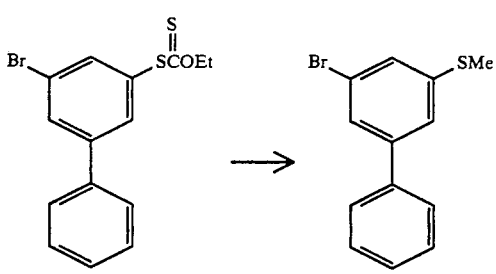

To a stirred solution of 10.79 g (30.7 mmole) of xanthate derivative from Example 16 in 140 mL of anhydrous THF at 0° C. under a nitrogen atmosphere was added 6.1 mL (92 mmole) of ethylene diamine and the mixture stirred further for 10 minutes. After this time, 5.4 mL (86 mmole) of methyl iodide was added, the ice-H$_2$O bath removed, and the mixture stirred 1 hour longer.

The mixture was partitioned between Et$_2$O/ice-H$_2$O and the organic phase separated, washed with brine, dried over Na$_2$SO$_4$/MgSO$_4$, filtered, and evaporated.

The residue was purified by distillation to give 5.82 (68%) of 3-bromo-5-methylthiobiphenyl; NMR (CDCl$_3$) δ: 2.55 (s, SCH$_3$), 7.36–7.56 (m, Ar-H); MS: m/e 280, 278 (M+).

EXAMPLE 18

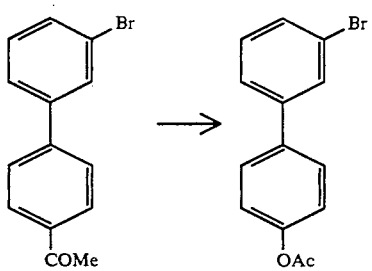

A stirred mixture of 1.19 g (5.84 mmole) of 85% m-chloroperoxybenzoic acid and 1.24 g (4.49 mmole) of 3-bromo-4'-acetylbiphenyl [prepared according to E. Berliner and E. A. Blommers, *JACS*, 73, 2479 (1951)] in 15 mL 1,2-dichloroethane was refluxed under a nitrogen atmosphere for 17 hours.

The cooled mixture was partitioned between Et$_2$O/ice-H$_2$O/5% Na$_2$S$_2$O$_3$ (aq.) solution and the organic phase separated, washed with ice-H$_2$O/saturated NaHCO$_3$ (aq.) solution and then saturated NaCl solution, dried over Na$_2$SO$_4$, filtered, and evaporated.

The residue was purified by PLC [one development CH$_2$Cl$_2$-petroleum ether] to give 1.09 g (83%) of 3-bromo-4-acetoxy-biphenyl; NMR (CDCl$_3$) δ: 2.33 (s, OAc), 7.14–7.7 (m, Ar-H).

EXAMPLE 19

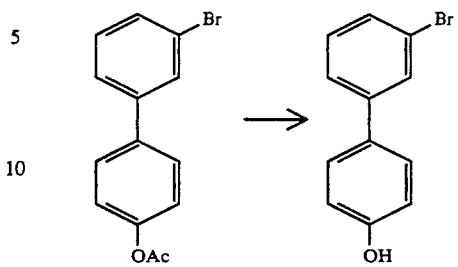

To a stirred solution of 1.07 g (3.67 mmole) of 3-bromo-4-acetoxybiphenyl in 10 mL methanol at ambient temperature under a nitrogen atmosphere was added 0.92 mL of 4.4M sodium methoxide in methanol solution (4 mmole). The mixture was stirred for 20 minutes and partitioned between Et$_2$O/ice-H$_2$O/2N HCl (aq.) and the organic phase separated, washed with saturated NaCl solution, and then ice-H$_2$O/saturated NaHCO$_3$ (aq) solution, dried over Na$_2$SO$_4$, filtered, and evaporated. The product was dried in vacuo to give 1.05 g of crude 3-bromo-4'-hydroxybiphenyl which was used without further purification.

EXAMPLE 20

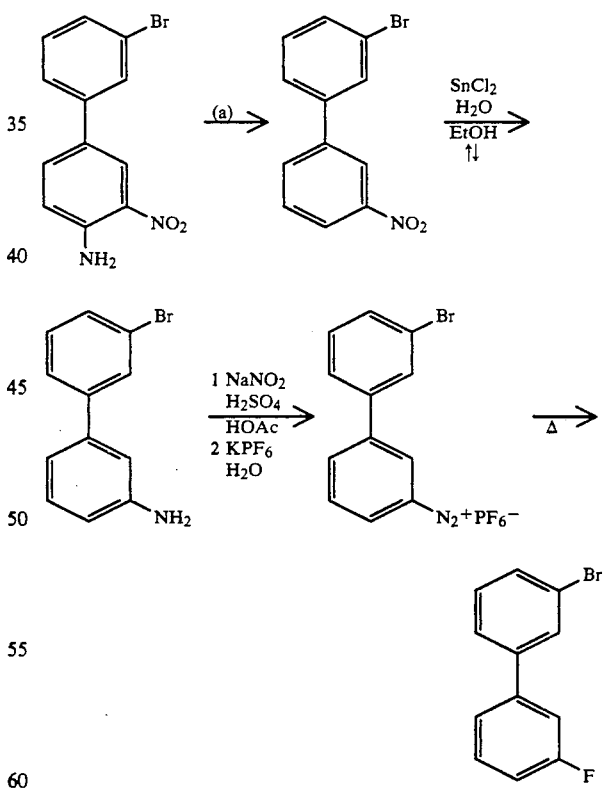

step (a)

To a stirred solution of 816 μL (6.2 mmole) of 90% t-butylnitrile in 15 ml of DMF at 65° C. under nitrogen atmosphere was added dropwise, a solution of 905 mg (3.1 mmole) 3-bromo-3'-nitro-4'-aminobiphenyl [C. Dell'Erba, G. Garbarino, and G. Guanti, *Tetrahedron*, 27. 113 (1971)] in 10 mL DMF over a period of 6 minutes. The mixture was stirred further as above for 8 minutes.

The cooled mixture was partitioned between Et₂O-/ice-H₂O and the organic phase separated, washed twice with ice-H₂O, then with saturated NaCl solution, dried over Na₂SO₄, filtered, and evaporated.

The residue was purified by florisil chromatography with CH₂Cl₂-petroleum ether solvent to give a quantitative yield of 3-bromo-3'-nitrobiphenyl; NMR (CDCl₃) δ: 7.32–8.46 (m, Ar-H).

Using the analogous procedure outlined in Exs. 10, 11 and 12, 3-bromo-3'-fluorobiphenyl was obtained.

EXAMPLE 21

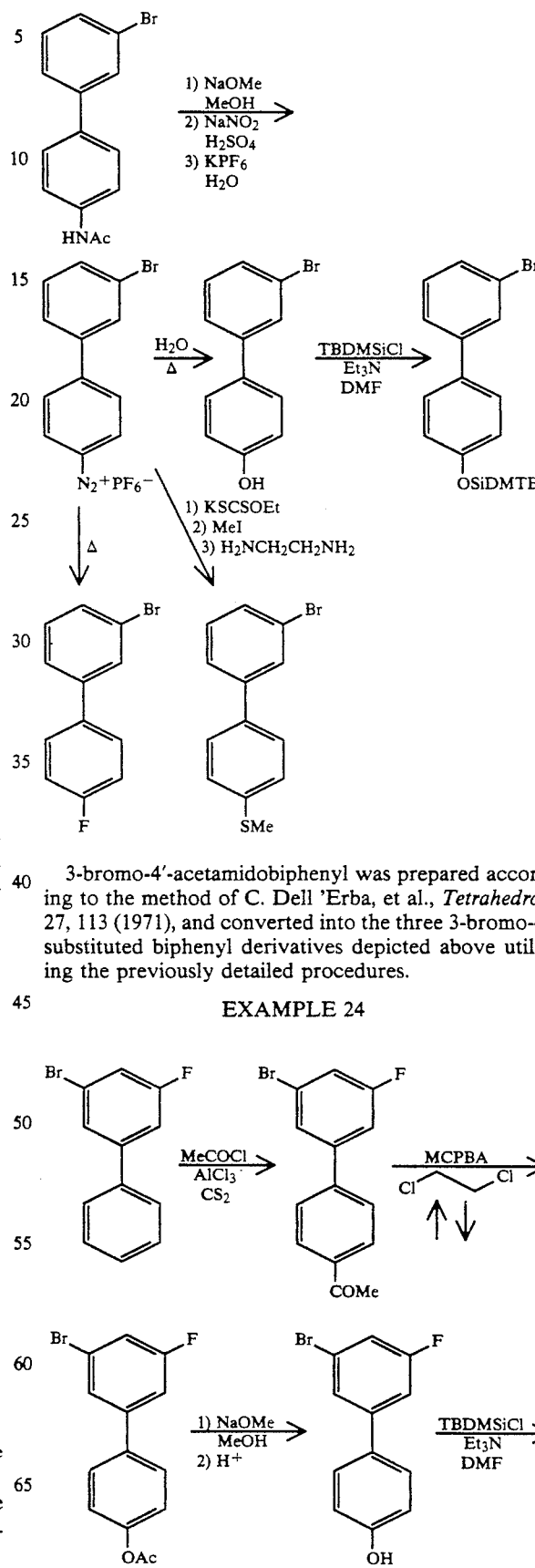

In a fashion analogous to the procedures outlined in Examples 13–15, the 3-bromo-3'-aminobiphenyl from Example 20 was converted into 3-bromo-3'-t-butyldimethylsiloxybiphenyl.

EXAMPLE 22

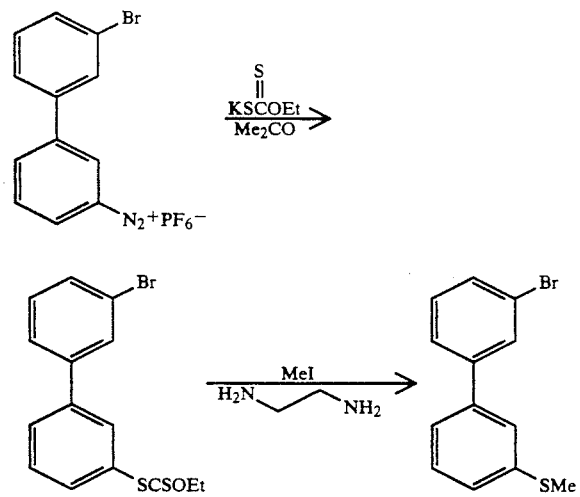

Utilizing the procedures previously outlined, the diazonium salt of Example 20 was converted to 3-bromo-3'-methylthiobiphenyl.

EXAMPLE 23

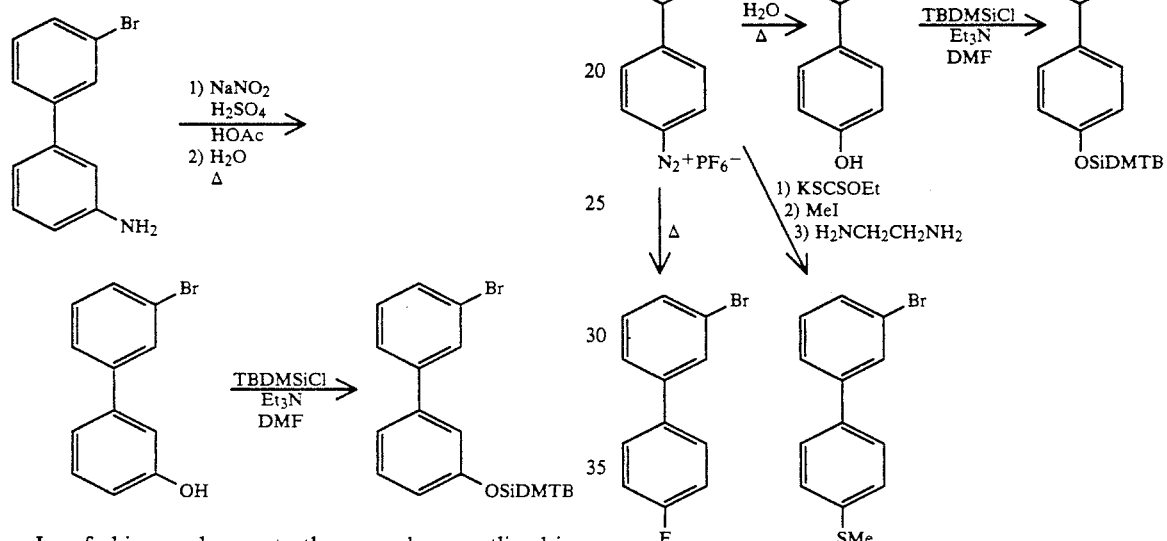

3-bromo-4'-acetamidobiphenyl was prepared according to the method of C. Dell 'Erba, et al., *Tetrahedron*, 27, 113 (1971), and converted into the three 3-bromo-4'-substituted biphenyl derivatives depicted above utilizing the previously detailed procedures.

EXAMPLE 24

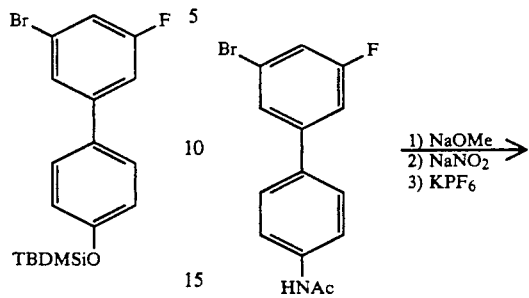

3-bromo-5-fluoro-4'-t-butyldimethylsilyloxybiphenyl was prepared in four steps utilizing the procedures previously detailed.

EXAMPLE 25

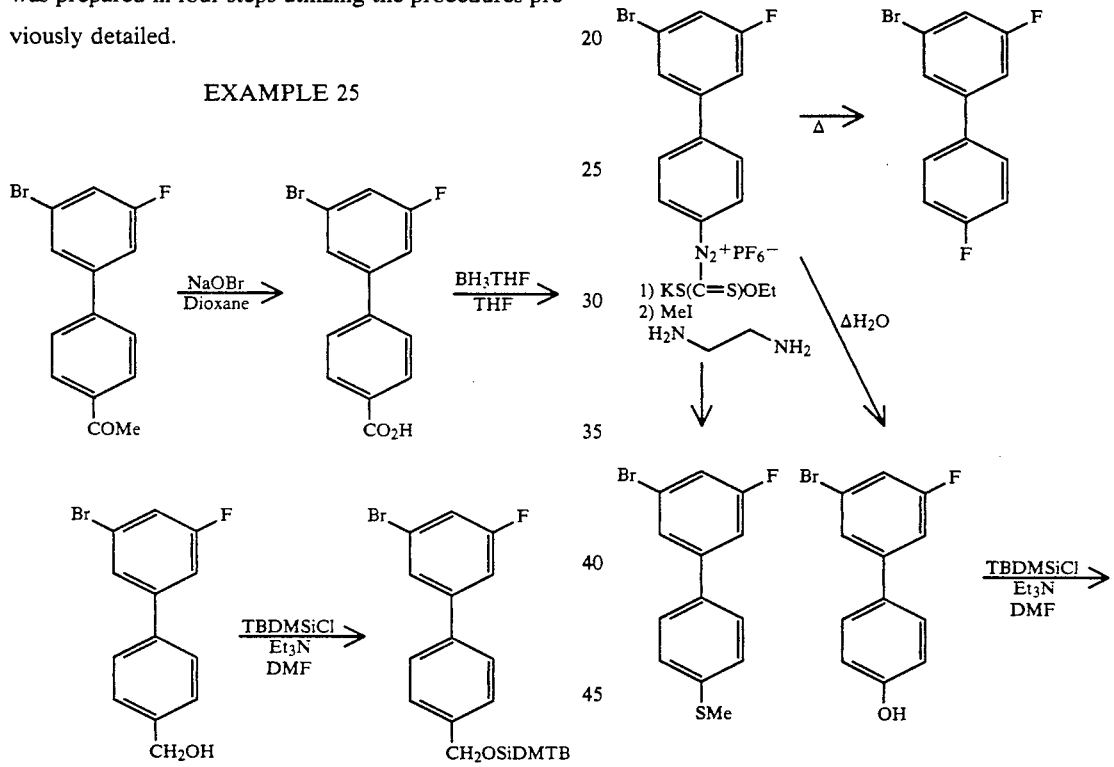

3-bromo-5-fluoro-4'-t-butyldimethylsilyloxymethylbiphenyl was synthesized as outlined above employing the previously described procedures.

EXAMPLE 26

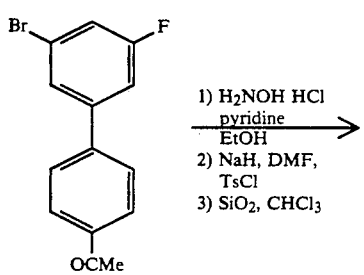

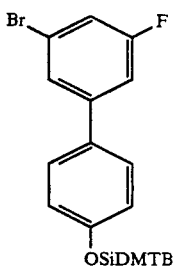

Three 3-bromo-5fluoro-4'-substituted biphenyl derivatives depicted above were prepared by the standard procedures previously disclosed.

EXAMPLE 27

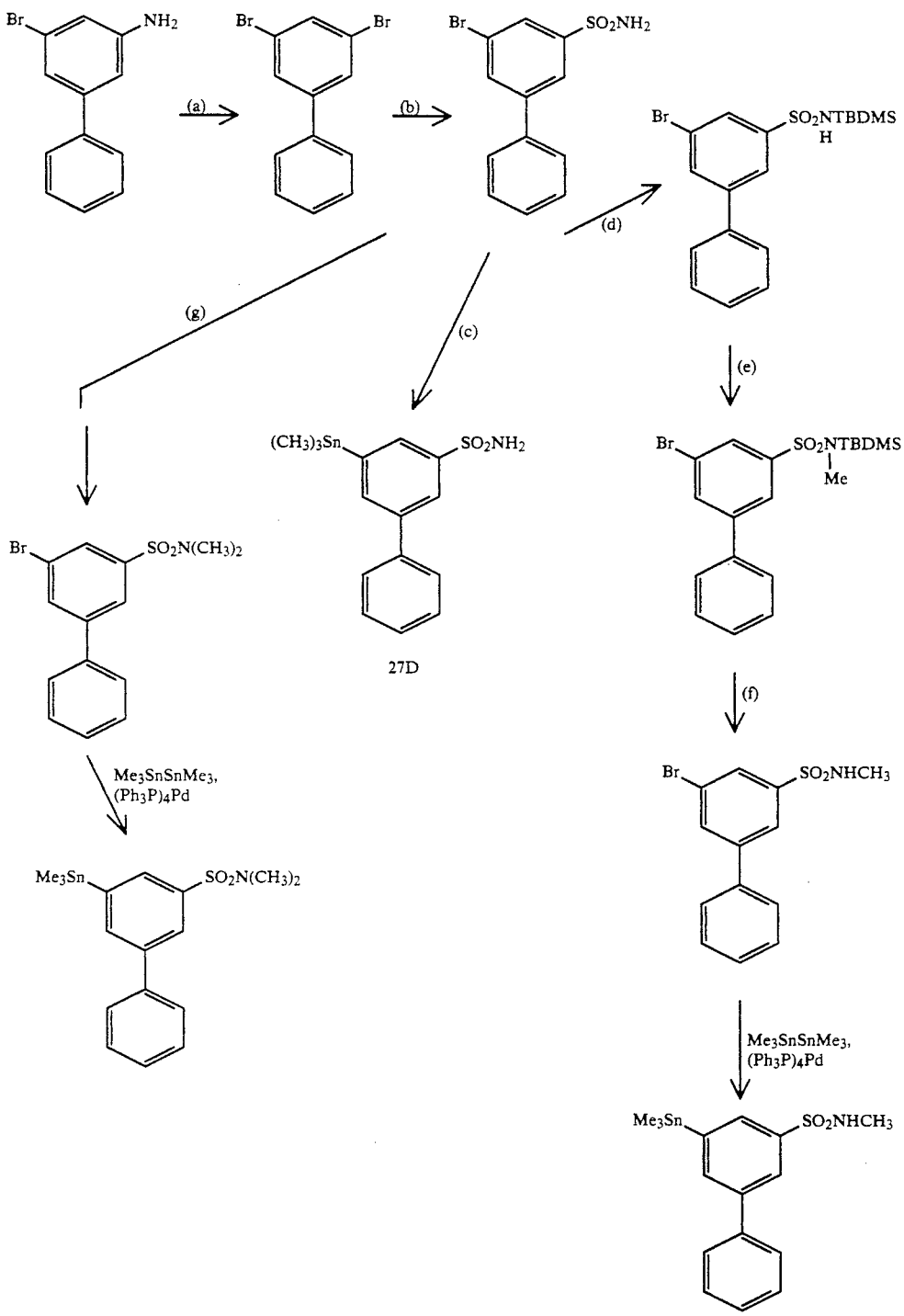

step(a)

To a stirred solution of sodium nitrite (4.4 g; 63.9 mmol) in 44.3 ml of sulfuric acid in an ice-water bath was added a solution of 3-amino-5-bromobiphenyl (15.0 g, 60.1 mmol) in 176.7 ml glacial acetic acid over 30 minutes. The solution was stirred an additional 10 minutes. To a stirred solution of copper(I)bromide (9.5 g, 66.3 mmol) in 78.6 ml of 48% HBr at R.T. was added the above diazonium salt solution and the reaction mixture was stirred for 45 minutes under an inert atmosphere of nitrogen. The reaction appeared complete by TLC (petroleum ether). The reaction was quenched by the addition of a 1.5L 5N NaOH-ice solution and the aqueous portion (pH 6.5) was extracted with 2.0L ether. The ether extract was washed three times with brine and the solvent was removed in vacuo to provide 18.6 g of a brown oil. The crude material was purified by flash chromatography on silica gel eluting with hexanes. The higher $R_f$ product gave 15.6 g (83.1%) of 3,5-dibromobiphenyl and the lower $R_f$ by product gave 0.7 g of 3-bromobiphenyl. $^1$H NMR (300 MHz, CDCl$_3$, ppm): δ 7.36-7.54 (m,5H); 7.6-7.68 (m,3H).

step(b)

To a stirred solution of 3,5-dibromo-biphenyl (0.5 g, 1.60 mmol), in 5 ml dry THF under $N_2$ atmosphere at $-78°$ C., was added 0.67 ml of 2.5M n-butyllithium (1.68 mmol). A clear yellow solution resulted. After stirring 5 minutes, a solution of $SO_2(g)$ (0.12 g) in 1.0 ml THF was added via syringe; TLC indicated nearly complete reaction. To the stirred reaction mixture was added 2,4,6-triisopropylbenzenesulfonylhydroxylamine (0.57 g, 2.0 mmol) and it was stirred for 15 minutes. The reaction appeared incomplete by TLC, and additional aminating agent (45.3 mg, 0.1 mmol) was added and the reaction stirred 15 minutes. This process was repeated and then the reaction mixture was partitioned between ethyl acetate/ice/water; the organic layer was separated and washed three times with 10 ml $H_2O$, and three times with 10 ml brine. The organic layer dried over $MgSO_4$, filtered and the solvent removed in vacuo, to give 1.0 g crude of product. The residue was purified by plate-layer chromatography eluted with dichloromethane-ethyl acetate (30:1) to give 300 mg (60%).

$^1$H NMR (200 MHz, DMSO, ppm): δ 7.47–7.59 (m, 3H), 7.71–7.78 (m, 2H), 7.95 (m, 1H), 8.08–8.13 (m, 2H).

IR: (nujol) 3370,3275 cm$^{-1}$.
MS: (m/e) 313,311 ($M^+$).

step(c)

A mixture of 3-bromo-5-sulfonylbiphenyl (0.11 g, 0.36 mmole), $Pd(PPh_3)_4$ (8.4 mg, 7.3 μmol) and triphenylphosphine (1.0 mg, 3.8 μmol) in 1.33 mL toluene was stirred and degassed with a nitrogen purge. A solution of hexamethylditin (130.8 mg, 0.40 mmol) in 0.30 μL toluene was added via syringe and the solution was refluxed under $N_2$ for 2 h. The cooled reaction mixture was partitioned between ethyl acetate/ice/water/aq. $NaHCO_3$. The organic layer was separated and washed three times with 10 ml of cold (0° C.) 10% aq. $NaHCO_3$ solution and twice with 10 ml brine; dried over $MgSO_4$, filtered and concentrated in vacuo. The crude product, a yellow-orange oil was purified by chromatography on silica gel plates (2000μ) eluted with 30:1 $CH_2Cl_2$:EtOAc to give 95 mg (66.1%), as a white foam.

$^1$H NMR (300 MHz, $CDCl_3$, ppm): δ 0.38 (s, 9H), 4.96 (bs, 2H), 7.35–7.48 (m, 3H), 7.55–7.59 (m, 2H), 7.85 (m, 1H), 8.0 (m, 1H), 8.06 (m, 1H).

IR: ($CH_2Cl_2$) 3430, 3335 cm$^{-1}$.

step(d)

A stirred mixture of the sulfonamide (25 mg, 0.08 mmol), t-butyldimethylsilyl chloride (0.60 mg, 4.0 μmol), and N-tert-butyldimethylsilyl)-N-trifluoromethylacetamide (20.7 μL, 88 μmol) in 0.5 ml MeCN was refluxed for 2 hours under $N_2$ atmosphere. The cooled reaction mixture was partitioned between EtAOc/ice/water/aq. $NaHCO_3$. The organic layer was separated and washed three times with 10 mL dilute aq. $NaHCO_3$ solution and three times with 10 mL brine; dried over $MgSO_4$; filtered and concentrated in vacuo to give 127 mg of crude product. It was chromatographed on a silica gel plate (1000μ) eluted with 9:1 $CH_2Cl_2$: hexane to give 24 mg(70.3%) of product.

$^1$H NMR (200 MHz, $CDCl_3$, ppm): δ 0.28 (s, 6H), 0.94 (s, 9H); 4.46 (bs, 1H), 7.43–7.60 (m, 5H), 7.89 (m, 1H), 7.99 (m, 1H), 8.03 (m, 1H).

step(e)

To a stirred solution of the silylated sulfonamide (42.7 mg, 0.1 mmol) in 0.43 ml DMF was added 4.3 mg (0.11 mmol) of a 61.1% mineral oil dispersion of NaH. The mixture was stirred under $N_2$ at ambient temperature for 1 hr. To the stirred mixture was added neat methyliodide (29.8 mg, 0.21 mmol) and stirred further for 3 hours; followed the reaction by TLC (1:1 hexane:dichloromethane). The reaction mixture was partitioned between ethyl acetate/ice and water, and the organic layer separated, washed three times with 20 mL deionized water and three times with 20 mL brine; then dried over $MgSO_4$, filtered and concentrated in vacuo. The crude product (44.0 mg) was chromatographed on a silica gel plate (1000μ) eluted with 1:1 hexane:dichloromethane to give 32.0 mg (78.1%) purified product.

$^1$H NMR (200 MHz, $CDCl_3$, ppm): δ 0.38 (s, 6H), 1.07 (s, 9H), 2.80 (s, 3H), 7.44–7.62 (m, 5H), 7.92 (m, 2H), 7.97 (m, 1H).

step(f)

To a stirred solution of 3-bromo-5-N-t-butyldimethylsilyl-N-methylsulfonamidobiphenyl (32.0 mg, 73.0 μmol) in 0.32 ml anhydrous THF at 0° C. under $N_2$ was added sequentially 12.5 μl (0.22 mmol) glacial acetic acid and then a 1M solution of tetrabutylammonium fluoride (80.3 μl, 80.3 μmol) in the THF. The mixture was stirred at 0° C. for 0.5 hr. The reaction mixture was partitioned between EtOAc/ice-water, the organic layer was separated and washed three times with saturated sodium bicarbonate solution, three times with 10 mL water and three times with 10 mL brine, then dried over $Na_2SO_4$, filtered and the solvent removed in vacuo to give 28 mg of crude product. The mixture was chromatographed on a 1000μ silica gel plate eluting with 9:1 dichloromethane:hexane to give 24 mg (84%) the desired N-methyl sulfonamide.

$^1$H NMR (200 MHz, $CDCl_3$, ppm): δ 2.75 (d, 3H), 4.4 (bm, 1H), 7.45–7.61 (m, 5H), 7.96 (m, 1H), 7.98 (m, 1H), 8.0 (m, 1H).

Using the procedures disclosed in step(c), this material was converted into the analogous trimethylstannyl derivative.

step(g)

To a stirred solution of the sulfonamide (0.2 g, 641 μmol) in 2 ml DMF was added 52.6 mg (1.34 mmol) 61.1% of a mineral oil dispersion of NaH and the reaction stirred 1 hour at room temperature until gas evolution is complete. To the stirred mixture at 0° C. was added neat methyliodide (0.17 mL), and the solution stirred 30 minutes; TLC (1:1 $CH_2Cl_2$:hexane) indicated complete reaction. The reaction mixture was partitioned between ethyl acetate and ice-water, and the organic extract separated, washed three times with 50 mL brine, dried over $Na_2SO_4$, filtered and concentrated in vacuo to give 250 mg of crude product. It was chromatographed on two 2000μ silica gel plates eluted with 1:1 hexane:dichloromethane to give 201 mg(92.2%) the desired product.

$^1$H NMR (200 MHz, $CDCl_3$, ppm): δ 2.8 (s, 6H), 7.46–7.62 (m, 5H), 7.91 (m, 2H), 7.96 (m, 1H).

Using the procedure described in step(c), this biphenyl derivative was converted to the analogous trimethylstannyl derivative.

EXAMPLE 28

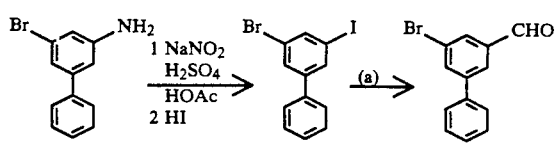

-continued

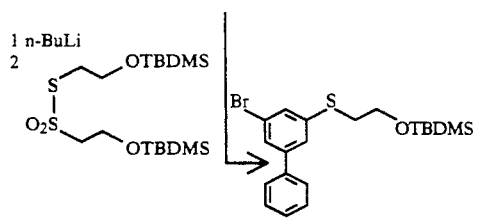

step (a)

To a stirred solution of 3-bromo-5-iodobiphenyl (5.5 g, 15.4 mmol) in 70 mL dry THF at −78° C. under $N_2$ atmosphere was added dropwise a 2.5M solution of n-butyllithium in hexanes (6.4 mL, 16.1 mmol) over 5 minutes. The mixture was stirred 10 minutes and anhydrous DMF (2.4 mL, 30.7 mmol) was quickly added. After 15 minutes the reaction was quenched by the addition of saturated ammonium chloride solution and warmed to room temperature. The reaction mixture was partitioned between diethyl ether and water, the organic extract washed with brine, dried over $MgSO_4$, filtered and concentrated in vacuo. The crude product (4.37 g), as a yellow oil, was chromatographed on silica gel eluted with a gradient of 0–3% ethyl acetate in hexane to provide. 3.61 g. (90%) of purified product, as an opaque oil.

$^1H$ NMR (200 MHz, $CDCl_3$, ppm): δ 7.4–8.04 (m, 8H), 10.04 (s, 1H);
IR: ($CH_2Cl_2$): 1700 cm$^{-1}$;
MS: (m/e) 262,260 ($M^+$).

EXAMPLE 29

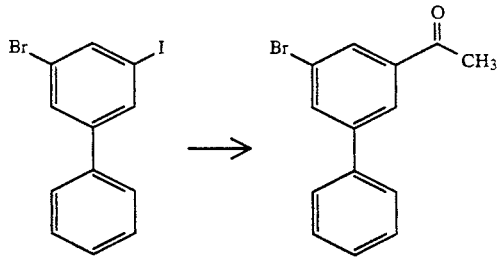

To a stirred solution of 3-bromo-5-iodobiphenyl (0.5 g, 1.4 mmol) in 5 mL dry THF at −70° C. under $N_2$ atmosphere was added a 2.5M solution of n-butyllithium in hexanes (0.58 mL, 1.47 mmol). The mixture was stirred 10 minutes, and a 0.2M solution of magnesium bromide (14 mL, 2.8 mmol) in THF was added. The reaction was warmed to −23° C. in a dry ice-$CCl_4$ bath. After 15 minutes at −23° C., neat 2-acetylthiopyridine (178 μl, 1.40 mmol) was added and the reaction was monitored by TLC. The 2-acetylthiopyridine was completely consumed after 10 minutes however, starting material remained, and an additional 50 μl of 2-acetylthiopyridine was added. The reaction mixture was warmed to room temperature and quenched with 2 mL of 1M aqueous $NH_4Cl$ and then partitioned between ethylacetate and cold water. The organic layer was separated and washed with cold 2N NaOH and brine, then dried over $MgSO_4$, filtered and concentrated in vacuo to give 486 mg of crude material. It was chromatographed on two 2000μ silica gel plates eluted with 9:1 hexane:ethylacetate to give 202 mg (52%), as a crystalline solid.

$^1H$ NMR (200 MHz, $CDCl_3$, ppm): δ 2.64 (s, 3H), 7.4–8.1 (m, 8H).
IR ($CH_2Cl_2$): 1690 cm$^{-1}$.

EXAMPLE 30

27D

+

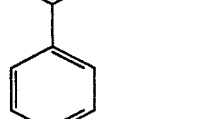

30A

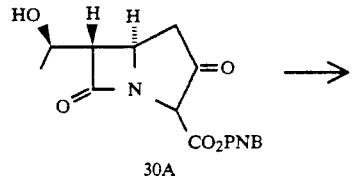

30B

To a dry flask charged with the bicyclic ketoester carbapenem derivative (58.4 mg, 0.168 mmol) and purged with $N_2$ was added 1.0 mL dry THF. The solution was chilled to −78° C. and diisopropylamine (25.8 μL, 0.184 mmol) was added. The reaction was stirred 10 minutes and became a clear yellow solution, then trifluoromethanesulfonic anhydride (30.6 μL, 0.184 mmol) was added and stirring continued at −78° C. for 15 minutes. To the reaction mixture was added neat triethylamine (25.4 μL, 184 μmol) and trimethylsilyl trifluoromethanesulfonate (35.6 mL, 184 μmol) and continued stirring for 20 minutes.

The arylstannane sulfonamide (73.0 mg, 0.18 mmol), $Pd_2$ (dba)$_3$.$CHCl_3$ (3.47 mg, 3.4 μmol) and tris (2,4,6-trimethoxyphenyl)phosphine (7.11 mg, 13.5 μmol) were added all at once after the addition of 0.83 mL N-methylpyrolidinone. Finally, a solution of 1.5M zinc chloride in diethyl ether (276 μl, 0.184 mmol) was added, and the reaction mixture was allowed to warm with the aid of a warm water bath for an additional 20 minutes during which time a wine red color developed. The reaction mixture was partitioned between ethyl acetate/ice and aqueous. $NaHCO_3$ mixture and the organic layer was separated and washed three times with 10 mL cold dilute $NaHCO_3$ and three times with 10 ml brine; dried over $MgSO_4$, filtered, and concentrated in vacuo. Chromatographed crude product on one 1000μ silica gel plate eluted with 2:3 hexane:ethyl acetate to give 70.2 mg (61.0%) of product.

$^1H$ NMR (300 MHz, $CDCl_3$, ppm): δ 0.12 (s, 9H), 1.25 (d, 3H), 3.19–3.41 (m 3H), 4.21–4.32 (m, 2H) 5.15 (d, 1H), 5.25 (d, 1H), 7.24–8.11 (m, 12H).

EXAMPLE 31

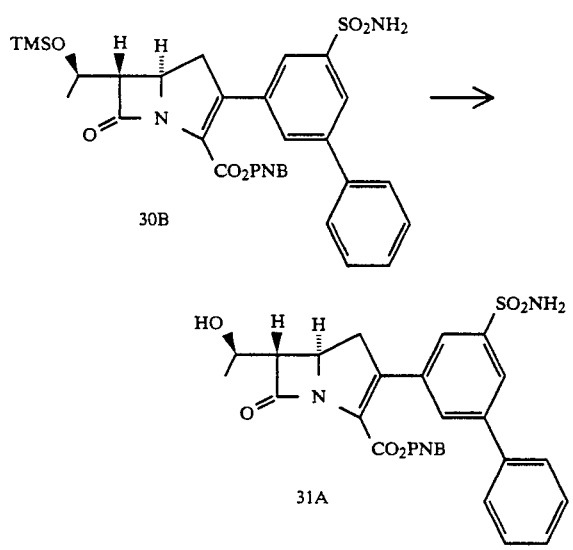

To a stirred solution of the silyl ether (67.0 mg, 0.107 mmol) in 1 mL dry THF at 0° C. was added glacial acetic acid (18.3 μl 0.321 mmol) and a solution of 1M tetrabutylammoniumfluoride in THF (107 μl, 0.107 mmol). The reaction mixture was stirred 10 minutes and then partitioned between EtOAc/ice/water/dilute aq. NaHCO$_3$. The organic layer was separated and washed three times with 10 mL saturated NaHCO$_3$ solution and three times with 10 mL brine, then dried over MgSO$_4$, filtered and concentrated in vacuo. The crude product (55.0 mg), a yellow foam, was chromatographed on a 1000μ silica gel plate eluting with 7:3 hexane:ethyl acetate to give the purified product 35.0 mg (59.2%).

$^1$H NMR (300 MHz, d$_6$-Me$_2$CO, ppm)δ: 1.32 (d, 3H), 3.38 (dd, 1H), 3.52 (dd, 1H), 3.7 (dd, 1H), 4.2 (m, 1H), 4.45 (m, 1H), 5.35 (ABq, 2H), 6.75 (bs, 2H), 7.4–7.7 (m, 5H), 7.94 (m, 1H), 8.15 (m, 2H).

IR (CH$_2$Cl$_2$): 1775, 1725 cm$^{-1}$.
UV (dioxane, λmax): 310 nm (sh), 259 nm.

EXAMPLE 32

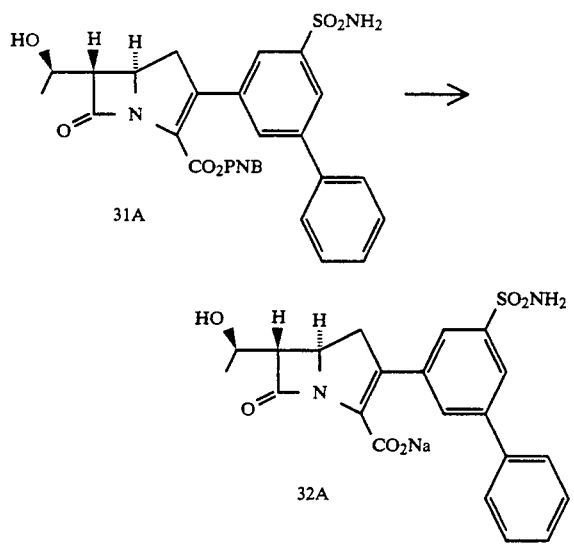

A mixture of 0.5 mL dry THF of p-nitrobenzyl ester (35.0 mg, 63.5 μmol), 3.5 mg 10% Pd/C, and NaHCO$_3$ (6.0 mg) was hydrogenated at 50 psi and ambient temperature for 15 minutes. After this time an additional 3.5 mg 10% Pd/C was added and the hydrogenation continued for 30 minutes at 50 psi. The reaction mixture was filtered through a celite pad to give a clear filtrate, which was concentrated in vacuo. The solid residue was dissolved in deionized H$_2$O and chromatographed on a 1000μ reverse phase silica gel plate eluted with 5:1 water:acetonitrile in a chilled developing chamber. The product 14.5 mg (50.5%) was isolated as a white fluffy solid, after lyophilization.

$^1$H NMR (300 MHz, D$_2$O, ppm) δ: 1.24 (d, 3H), 3.18 (m, 1H), 3.56 (m, 1H), 3.64 (m, 1H), 4.38 (m, 2H), 7.5–7.82 (m, 5H), 7.87 (m, 2H), 8.08 (bs, 1H).

IR (nujol): 1750, 1595 cm$^{-1}$.
UV (H$_2$O, λmax): 303, 254 nm.

EXAMPLE 33

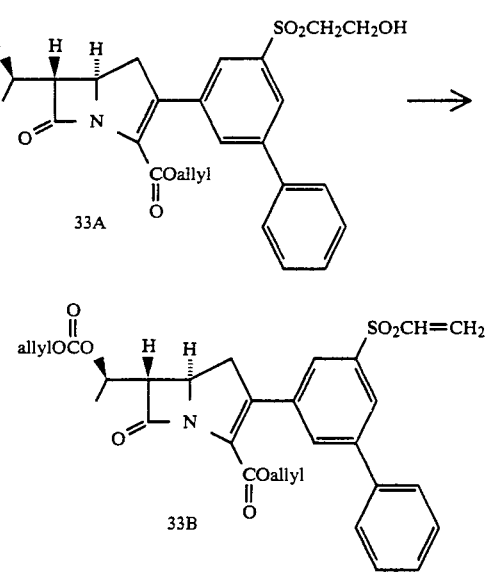

To a stirred solution of the carbapenem derivative (60 mg, 0.103 mmol) in 0.6 mL dry acetonitrile at 0° C. under N$_2$ atmosphere was added neat N-methylimidazole (17.2 μl, 0.216 mmol) and trifluoromethanesulfonic anhydride (18.2 μl, 0.108 mmol). The progress of the reaction was followed by TLC. After 15 minutes, the TLC indicated the complete disappearance of starting material. The reaction mixture was concentrated in vacuo. The 200 MHz NMR indicated a mixture of vinyl sulfone and the imidazolium adduct. The crude product was dissolved in dichloromethane, transferred into a 15 ml centrifuge tube, concentrated to a 1.0 mL volume and the imidazolium adduct precipitated by the addition of diethyl ether. After centrifuging the ether was decanted off, and evaporated to yield 32 mg (55%) of the vinyl sulfone product as a white foam.

$^1$H NMR (200 MHz, CDCl$_3$, ppm) δ: 1.52 (d, 3H), 3.31–3.39 (m, 2H), 3.46–3.51 (dd, 1H), 4.31–4.41 (dt, 1H), 4.65–4.74 (m, 4H), 5.16–5.44 (m, 5H), 5.79–6.04 (m, 2H), 6.1 (d, 1H), 6.5 (d, 1H), 6.66 (dd, 1H), 7.4–7.63 (m, 5H), 7.83–7.87 (m, 2H), 8.06 (m, 1H).

EXAMPLE 34

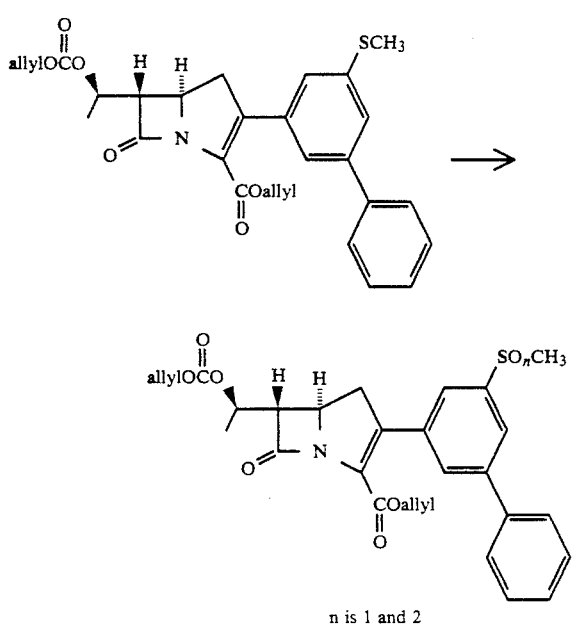

n is 1 and 2

To a stirred solution of 2-(5'-methylthio-3'-biphenyl)-carbapenem (41.1 mg, 79.2 μmol) in 1 mL dichloromethane at 0° C. under a N₂ atmosphere was added 0.5M aqueous NaHCO₃ (0.5 mL) and MCPBA (19.1 mg, 0.11 mmol). The reaction was stirred 25 minutes at 0° C.; at 10 minutes the TLC indicated the complete consumption of the methyl sulfide and the presence of two new spots. The reaction was quenched with 0.5M aqueous Na₂S₂O₃ solution and partitioned between EtOAc/ice/water. The organic phase was separated and washed with brine, dried over Na₂SO₄, filtered and concentrated in vacuo to give 46.2 mg of crude product mixture, a clear film. It was chromatographed on a 1000μ silica gel plate eluting with 15% EtOAc in dichloromethane to give 9.3 (21.3%) of sulfone, as the more mobile component; and 25.8 mg (60.9%) of sulfoxide, as the less mobile component.

Sulfoxide:

$^1$H NMR: (300 MHz, CDCl₃, ppm) δ: 1.48 (d, 3H), 2.77 (s, 3H), 3.25-3.36 (m, 2H), 3.44 (dd, 1H), 4.33 (td, 1H), 4.59-4.72 (m, 4H), 5.13-5.39 (m, 5H), 5.78-5.97 (m, 2H), 7.24-7.79 (m, 8H).

IR: (CH₂Cl₂) 1772, 1745, 1720 cm$^{-1}$.

UV: (dioxane) λmax 314,258 nm.

Sulfone:

$^1$H NMR: (300 MHz, CDCl₃, ppm) δ; 1.48 (d, 3H), 3.09 (s, 3H), 3.26-3.36 (m, 2H), 3.45 (dd, 1H), 4.33 (td, 1H), 4.61-4.71 (m, 4H), 5.14-5.39 (m, 5H), 5.79-5.92 (m, 2H), 7.24-8.09 (m, 8H).

IR: (CH₂Cl₂) 1775, 1745, 1722 cm$^{-1}$.

UV: (dioxane) λmax 312,257 nm.

EXAMPLE 35

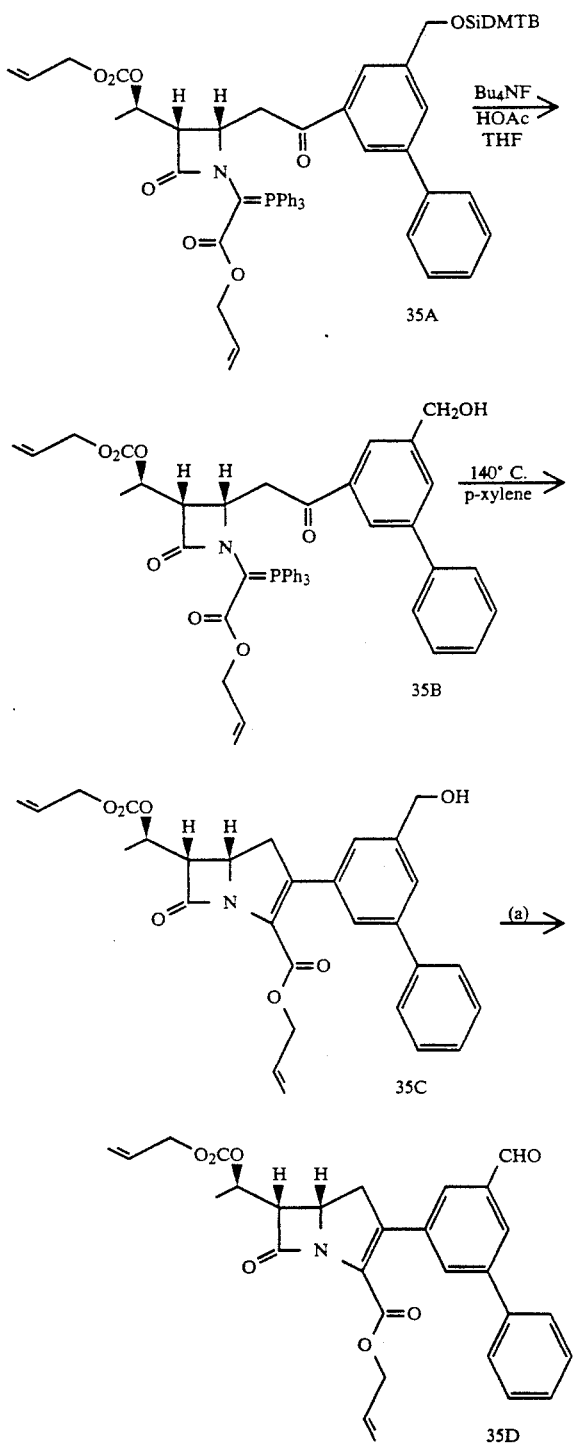

step (a)

To a stirred solution of 65.3 mg (0.13 mmole) of carbapenem biphenyl carbinol derivative in 1.6 mL sieve dried CH₂Cl₂ at ambient temperature was added sequentially 17 mg of powdered 3 Å sieves and 27 mg (0.23 mmol) of N-methylmorpholine-N-oxide. The yellow solution was stirred for 5 minutes and then 9.1 mg (0.26 mmole) of tetrapropylammonium perruthenate was added. The resulting mixture was stirred 5 minutes and then quickly filtered through a layer on silica gel with CH$_2$Cl$_2$-EtOAc (1:1) solvent. The filtrate was rotoevaporated and dried in vacuo to give 51.9 mg (80%) of oxidized product; NMR (CDCl$_3$) δ: 1.5 (d, CH$_3$), 3.34 (m, 2H-1), 3.46 (dd, 1H-6), 4.34 (td, 1H-5), 4.34 (m, 2-OCH$_2$CH=CH$_2$), 5.24 (m, 1H-8 and 2—CH=CH$_2$), 5.88 (m, 2—CH=CH$_2$), 7.46 (m, 3Ar-H), 7.6 (d, 2Ar-H), 7.82 (s, 1Ar-H), 7.84 (s, 1Ar-H), 8.05 (s, 1Ar-H), and 10.1 (s, CHO).

EXAMPLE 36

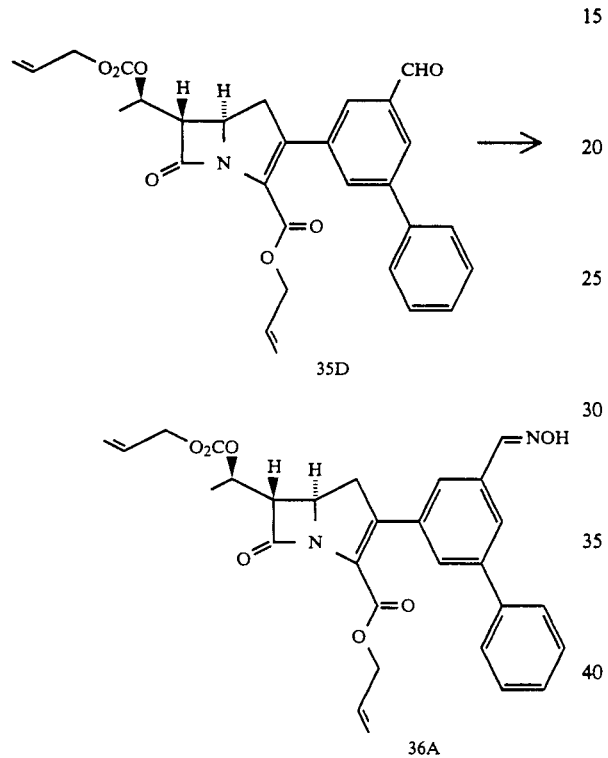

To a stirred solution of 51.9 mg (0.1 mmole) of carbapenem biphenyl carboxaldehyde derivative from Example 35 in 0.7 mL absolute ethanol and 0.7 mL pyridine at 0° C. under a nitrogen atmosphere was added 7.2 mg (0.1 mmole) of neat hydroxylamine hydrochloride. The mixture was stirred at 0° C. for 5 minutes and then partitioned between EtOAc/ice/saturated NH$_4$Cl (aq.) solution and the organic phase separated. It was washed successively with ice/saturated NaHCO$_3$ (aq.) solution, H$_2$O, and brine, then dried over Na$_2$SO$_4$, filtered, and evaporated.

The crude oxime was immediately employed in the next transformation but maybe purified by PLC to give pure material; IR (CH$_2$Cl$_2$): 3560, 1780, 1745, and 1720 cm$^{-1}$; NMR (CDCl$_3$) δ: 1.52 (d, CH$_3$), 1.6 (bs, OH), 3.32 (m, 2H-1), 3.46 (dd, 1H-6), 4.34 (dt, 1H-5), 4.68 (m, 2-OCH$_2$CH=CH$_2$), 5.24 (m, 1H-8 and 2-CH=CH$_2$), 5.84 (m, 2-CH=CH$_2$), 7.36-7.78 (m, Ar-H), and 8.2 (s, CH=NO).

EXAMPLE 37

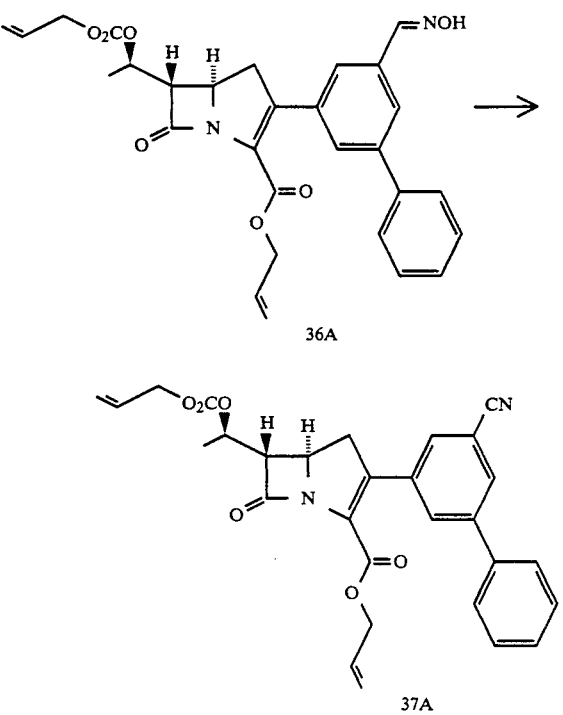

To a stirred solution of 53.1 mg (0.1 mmole) of crude oxime from Example 36 in 1.6 mL of sieve dried CH$_2$Cl$_2$ at −78° C. under a nitrogen atmosphere was added sequentially 21.9 mg (0.22 mmole) of neat triethylamine and 29.1 mg (0.1 mmole) of neat triflic anhydride. After stirring 15 minutes at −78° C., an additional 13.4 mg (0.05 mmole) of triflic anhydride was added and the mixture stirred further for 15 minutes.

The mixture was partitioned between EtOAc/ice/saturated NH$_4$Cl (aq.) solution and the organic phase was separated, washed with saturated NaHCO$_3$ (aq.) solution/ice and then brine, dried over Na$_2$SO$_4$, filtered, and evaporated.

The residue was purified by PLC [one development 5% EtOAc in CH$_2$Cl$_2$] to give 24.3 mg (47%) of biphenylnitrile carbapenem derivative; IR (CH$_2$Cl$_2$) 2235, 1780, 1745, and 1720 cm$^{-1}$; NMR (CDCl$_3$) δ: 1.5 (d, CH$_3$), 3.29 (m, 2H-1), 3.46 (dd, 1H-6), 4.34 (td, 1H-5), 4.66 (m, 2-OCH$_2$CH=CH$_2$), 5.26 (m, 1H-8 and 2-CH=CH$_2$), 5.88 (m, 2CH=CH$_2$), 7.38–7.83 (m, Ar-H).

EXAMPLE 38

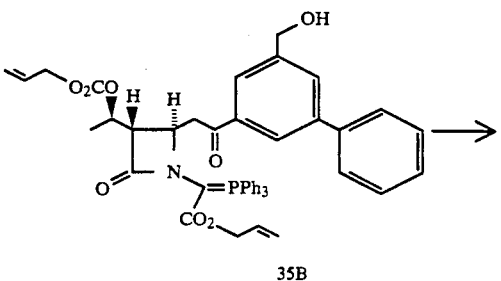

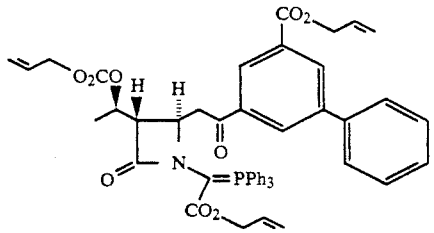

38B

To a stirred solution of 500 mg (0.65 mmole) of biphenylcarbinolazetidnonylphosphorane derivative in 10 mL acetone at 0° C. was added slowly 0.75 mL (2.0 mmole) of 2.67M Jones reagent. The mixture was stirred 15 minutes at ice-H₂O bath temperatures and 3 mL of saturated NaHSO₃ (aq.) solution added. The reaction mixture was decanted and partitioned between EtOAc/ice/0.1M pH 7 phosphate buffer. The organic phase was separated, dried over Na₂SO₄, filtered, evaporated, and dried in vacuo to give 287 mg (57%) of crude acid derivative; IR (CH₂Cl₂) 1743, 1690, and 1605 cm⁻¹.

To a stirred solution of 254 mg (0.32 mmole) of crude acid in 4 mL of DMF at ambient temperature was added 62 mg (0.48 mmole) of diisopropylethylamine and 58 mg (0.48 mmole) of allyl bromide. The resulting solution was stirred overnight at room temperature.

The reaction mixture was concentrated in vacuo and the concentrate partitioned between EtOAc and cold 1N HCl, and the organic phase separated, dried over Na₂SO₄, filtered, and evaporated.

The residue was purified by PLC [one development CH₂Cl₂-EtOAc (9:1)] to give (64%) of foamy ester product; IR (CH₂Cl₂) 1743, 1725 (sh), 1690, and 1610 cm⁻¹.

EXAMPLE 39

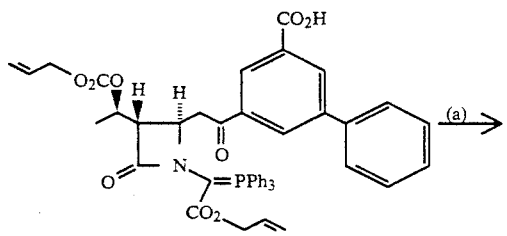

38A

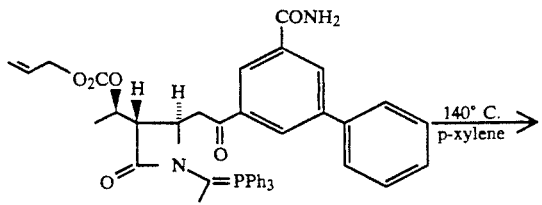

39A

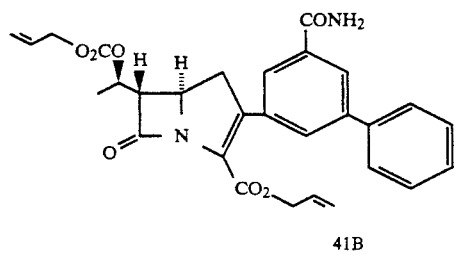

41B step (a)

To a stirred solution of 140 mg (0.18 mmole) of carboxylic acid derivative, prepared according to Example 38, in 4 mL THF at room temperature was added 45 mg (0.34 mmole) of neat 1-hydroxybenzotriazole and 44 mg (0.23 mmole) of 1-(3-dimethylaminopropyl)-3-ethylcarbodiimide hydrochloride were added, and the mixture stirred 0.75 hours. After this time 2 mL of cold, saturated NH₃ in THF solution was added and the mixture stirred for 1.0 hour. The reaction mixture was concentrated and purified by column chromatography on silica gel to give the amide product;

IR (CH₂Cl₂) 1743, 1680, and 1610 cm⁻¹.

EXAMPLE 40

Utilizing the procedure outlined in Example 39 and substituting MeOH for NH₃/THF, the corresponding methyl ester was prepared.

EXAMPLE 41

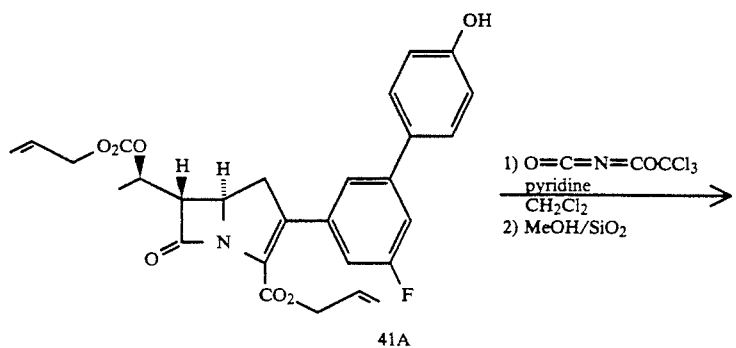

41A

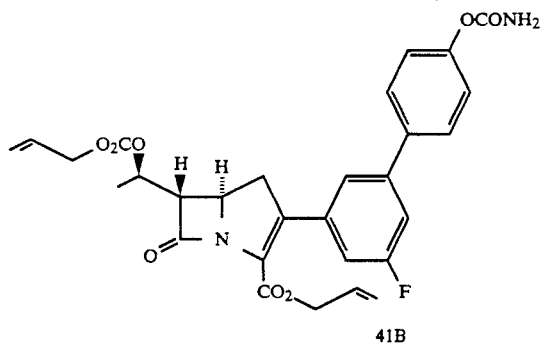

41B

To a stirred solution of 209.7 mg (0.4 mmol) of carbapenem derivative 41A in 3 mL of sieve dried methylene chloride at 0° C. under a nitrogen atmosphere was added sequentially 13.1 mg (0.165 mmol) of pyridine and then 117 mg (0.62 mmol) of trichloroacetylisocyanate. The resulting mixture was stirred at 0° C. for 40 minutes.

The reaction mixture was partitioned between ethylacetate, ice-H₂O, and 2N hydrochloric acid. The organic phase was separated, washed with saturated aqueous sodium chloride solution, dried over anhydrous sodium sulfate, filtered, evaporated, and dried in vacuo to give 313 mg of crude intermediate.

The intermediate was dissolved in 5 mL methanol cooled to 0° C. in an ice-H₂O bath, slurried with sufficient EM-60 silica gel and stirred further for 1 hour, and then aged overnight under refrigeration. The reaction mixture was filtered, washed with ether and the filtrate evaporated.

Purification by plate layer chromatography on two 1000 silica gel plates developed with methylene chloride-ether (6:1) provided 157.4 mg (69%) of 41B:

IR (CH$_2$Cl$_2$): 3535, 3430, 1780, 1750, 1720, cm$^{-1}$.

$^1$H NMR (200 MHz, CD14, ppm): δ 1.53 (d, 3H), 3.16–3.40 (m, 2H), 3.44 (dd, 1H), 4.32 (dt, 1H), 4.66 (m, 4H), 5.06 (bs, 2H), 5.1–5.44 (m, 5H), 5.74–6.04 (m, 2H), 6.98–7.58, (m, 7H).

UV (dioxane, λmax: 310, 277 nm.

EXAMPLE 42

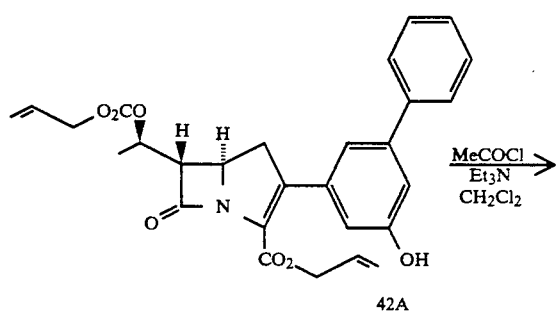

42A

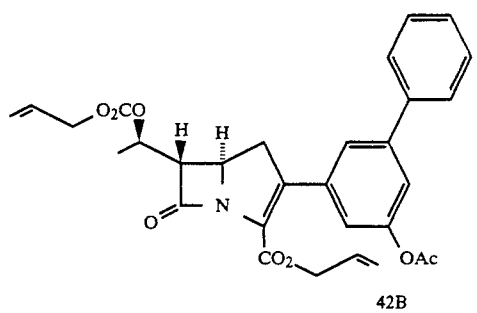

42B

To a stirred solution of 45.9 mg (0.08 mmol) of carbapenem derivative 42A in 2 mL sieve dried acetonitrile at 0° C. under a nitrogen atmosphere was added 17.7 μL (0.16 mmol) of triethylamine and then 8.4 μL (0.12 mmol) of acetyl chloride. The reaction mixture was stirred 25 min. at 0° C. and then partitioned between EtoAc/ice-H₂O. The organic phase was separated, washed with cold, saturated NaHCO₃ (aq) solution, then with saturated sodium chloride solution, dried over anhydrous Na₂SO₄, filtered, evaporated, and dried in vacuo to give a quantitative yield of acetoxyl derivative 42B;

IR (CH$_2$Cl$_2$): 1780, 1745, 1722 cm$^{-1}$.

$^1$H NMR (300 MHz, CDCl3, ppm): δ 1.48 (d, 3H), 2.3 (s, 3H), 3.18–3.36 (m, 2H3, 3.41 (dd, 1H), 4.28 (td, 1H), 4.58–4.76 (m, 4H), 5.1–5.4 (m, 5H), 5.74–5.95 (m, 2H), 7.06–7.54 (m, 8H).

UV (dioxane λ$_{max}$: 320, 252 nm.

EXAMPLE 43

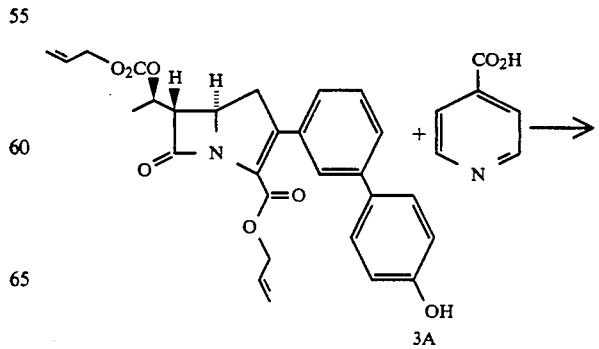

3A

-continued

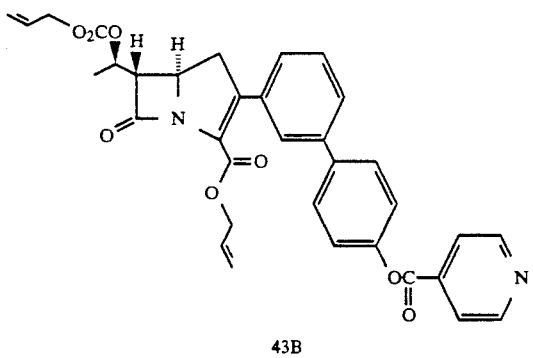

43B

A mixture of 12.6 mg (0.1 mmole) isonicotinic acid and 20.1 mg (0.12 mmole) of carbonyl diimidazole in 3 mL sieve dried acetonitrile was stirred ar 0° C. under a nitrogen atmosphere for 10 minutes and then at ambient temperature for 0.75 hours. After this time, 60 mg (0.1 mmole) of neat hydroxybiphenyl carbapenem derivative was added and the resulting mixture stirred further for 17 hours.

The mixture was partitioned between EtOAc and ice-H2O and the organic phase separated, washed with saturated NaCl solution, dried over Na2SO4, filtered, and evaporated.

The residue was purified by PLC [two developments CH2Cl2-EtOAc (4:1)] to give 17.1 mg (24%) of product; NMR (CDCl3) δ: 1.5 (d, CH3), 3.25 (m, 2H-1), 3.44 (dd, 1H-6), 4.32 (td, 1H-5), 4.68 (m, 2OCH2CH=CH2), 5.28 (m, 2CH=CH2 and 1H-8), 5.9 (m, 2CH=CH2), 7.28–7.68 (m, 8ArH), 8.04 (d, 2PyH), and 8.88 (d, 2PyH); IR (CH2Cl2): 1780, 1745, and 1725 cm⁻¹; UV: $\lambda_{max}^{dioxane}$ 255 nm, 300 nm (sh).

EXAMPLE 44

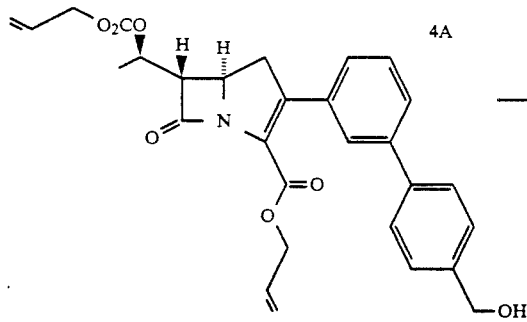

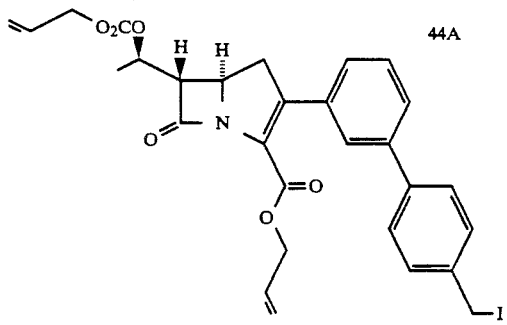

To a stirred solution of 47.3 mg (0.09 mmole) of alcohol 4A, prepared in Example 4, in 1 mL sieve dried CH2Cl2 at 0° C. under a nitrogen atmosphere was added sequentially 14.3 mg (0.14 mmole) of triethylamine and then 14 mg (0.12 mmole) of mesyl chloride. The mixture was stirred at 0° C. for 20 minutes and was then partitioned between EtOAc/ice-H2O/2N HCl and the organic phase was separated, washed with saturated sodium chloride solution, dried over sodium sulfate, filtered, and evaporated to give 56.6 mg of crude mesylate intermediate.

The crude mesylate was dissolved in 1 mL acetone and stirred with 28.2 mg (0.19 mmole) of sodium iodide in the cold for a few minutes and then further, with the ice-H2O bath removed, for 1.0 hour. After this time the mixture was partitioned between EtOAc/ice-H2O/5% aqueous sodium thiosulfate solution, and the organic phase was separated, washed with brine, dried over anhydrous sodium sulfate, filtered, and evaporated to give 53.7 mg of crude product.

Purification by PLC, [1 development hexane-EtOAc (2:1)] gave 28.3 mg (49%) of oily iodide 44A; IR(CH2Cl2): 1785, 1750, 1725 cm⁻¹; NMR(CDCl3) δ: 1.54 (d, J=6.4 Hz, CH3), 3.26 (dd, 1-H), 3.36 (dd, 1-H-1), 3.46 (dd, 1-H-6), 4.32 (dt, 1-H-5), 4.55 (s, CH2I), 7.3–7.62 (m, Ar-H); UV: $\lambda_{max}^{dioxane}$ 284 nm.

EXAMPLE 45

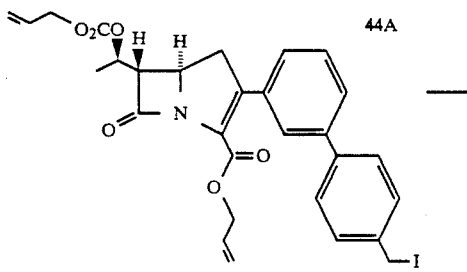

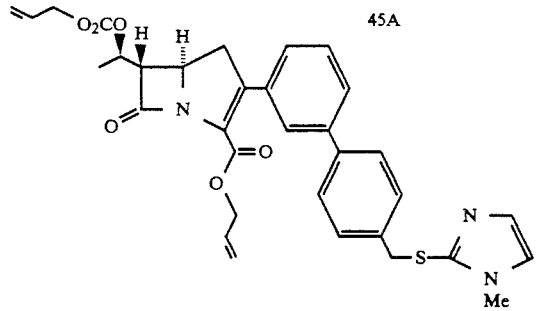

To a stirred solution of 40.6 mg (0.07 mmole) iodomethylbiphenylcarbapenem derivative from Example 44 in 1.5 mL acetonitrile at −20° C. under a nitrogen atmosphere was added 140 μL (0.07 mmole) of a freshly prepared stock solution of sodium 2-N-methylimidazolemercaptide in DMF which was prepared by the interaction of 250 mg (2.19 mmole) of N-methyl-2-mercaptoimidazole and sodium hydride in 5.5 mL of sieve dried DMF at 0° C. for 2 hours. The resulting mixture was stirred further at −20° C. for 15 minutes.

The mixture was partitioned between EtOAc/ice-H2O and the organic phase separated, washed with brine, dried over Na2SO4, filtered, evaporated, and dried in vacuo to give 34.9 mg (88%) of product: IR (CH2Cl2) 1780, 1745, and 1720 cm⁻¹; 1.5 (d, CH3), 3.3 (m, 2H-1), 3.32 (s, N-CH3), 4.22 (s, —SCH2), 4.31 (td, 1H-5), 4.68 (m, 2—OCH₂CH=CH₂), 5.26 (m, 1H-8 and 2—CH=CH₂), 5.88 (m, 2CH=CH₂), 6.88 (bs, 1-Im-H), and 7.1–7.6 (m, ArH and 1Im -H); UV: $\lambda_{max}^{dioxane}$ 278 nm, 315 nm (sh).

EXAMPLE 46

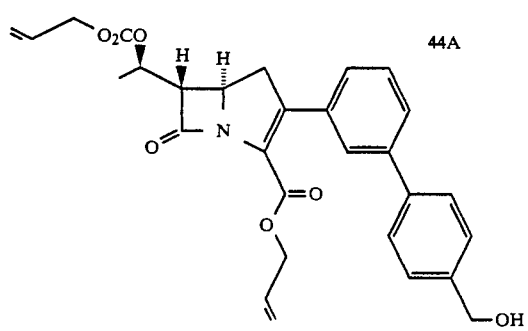

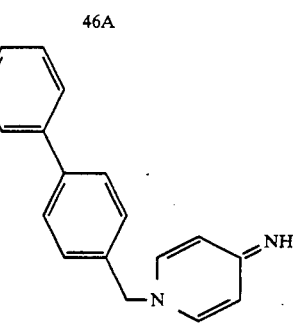

A mixture of 28.3 mg (0.05 mmole) of iodide 44A, prepared in Example 44, and 9.1 mg (0.97 mmole) of 4-aminopyridine was stirred in 0.5 mL sieve dried acetonitrile at ambient temperature under an atmosphere of nitrogen for 20 minutes. After this time, the mixture was partitioned between CH₂Cl₂/H₂O and the organic phase was separated, dried over sodium sulfate, filtered, and evaporated to give 30.6 mg (94%) of crude pyridinium salt intermediate.

The intermediate was combined with 6.8 mg (0.026 mmole) triphenylphosphine, 10 mg (0.0087 mmole) tetrakistriphenylphosphine palladium catalyst, 6.9 mg (0.048 mmole) 2-ethylhexanoic acid, and 95.2 μL (0.048 mmol) of a 0.5M solution of potassium-2-ethylhexanoate in EtOAc in 1.5 mL CH₂Cl₂ and stirred at ambient temperature for 2.0 hours. Product precipitation was immediate and after the above time it was triturated with EtOAc and collected by centrifugation and decantation of the superanatant. It was then washed similarly with Et₂O and dried in vacuo to give 23 mg crude material.

Purification of an MeCN-H₂O extract of the above material by reverse phase plate layer chromatography eluted with H₂O-MeCN (3:1) in the cold afforded after extraction of the product band with MeCN-H₂O (4:1), concentration of the extraction filtrate, and lyophilization 6.8 mg (35%) of product 46A: NMR (D₂O) δ: 1.31 (d, CH₃), 5.26 (s CH₂N), 5.76 (d, 2-pyridine-H's), 7.28–7.66 (m, Ar-H's), 7.96 (d,2-pyridine-H's) UV: $\lambda_{max}^{H_2O}$ 300 (sh), 273 nm.

EXAMPLE 47

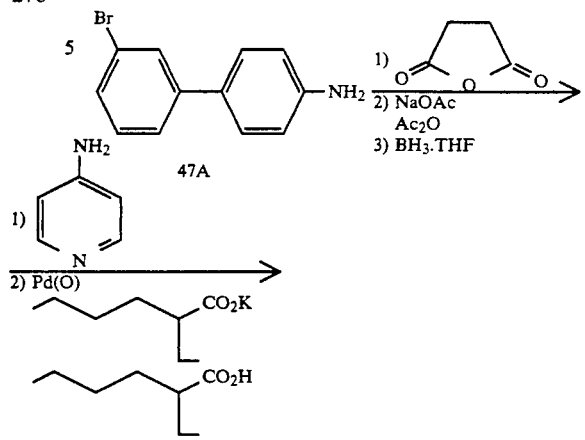

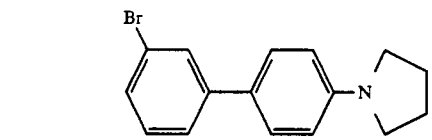

A mixture of 647 mg (2.57 mmol3) of 4'-amino-3-bromobiphenyl and 513.7 mg (5.13 mmole) of succinic anhydride was stirred magnetically in 15 mL sieve dried benzene at ambient temperature under an atmosphere of nitrogen for 2.0 hours. The insoluble product was collected by suction filtration, washed well with benezene, and dried in vacuo to give a quantitative yield of N-acylted acid product which was used without further purification.

A mixture of 911 mg (2.6 mmole) of the foregoing material and 644 mg (7.85 mmole) of sodium acetate in 15 mL of acetic anhydride was stirred under reflux for 50 minutes. The mixture was let cool and 30 mL of H₂O was added. The biphasic mixture was stirred until homogenity was achieved and the crystalline, insoluble product was collected by suction filtration. It was washed well with H₂O and dried in vacuo to give 787.8 mg (91%) of succinimide product: IR (CH₂Cl₂) 1720 cm⁻¹; NMR (CDCl₃) δ: 2.95 (s,4H), 7.37–7.74 (m, 8H).

To a stirred partial solution of 553.7 mg (1.68 mmole) of the above succinimide derivative in 10 mL of anhydrous THF under an inert atmosphere of nitrogen was added dropwise a 1M solution of borane-THF complex in THF (7.4 mL, 7.38 mmole). The resulting mixture was stirred at ambient temperature for 23 hours after which time the homogeneous reaction mixture was carefully quenched with sufficient MeOH. The mixture was partitioned between $Et_2O$/ice-$H_2O$/5N NaOH(aq.) solution and the organic phase was separated, washed with saturated sodium chloride solution, dried over anhydrous sodium sulfate, filtered, and evaporated to give 498 mg (93%) of crude product; recrystallized from $CH_2Cl_2$-MeOH to provide pure 4'-N-pyrrolidinyl-3-bromobiphenyl; NMR ($CDCl_3$) δ: 2.0 (m, 4H), 3.31 (m, 4H), 6.6 (d, 2H), 7.16–7.5 (m, 3H), 7.44 (d, 2H), 7.68 (m, 1-H).

EXAMPLE 48

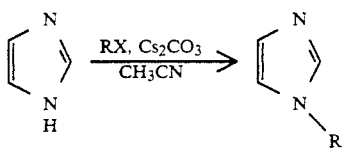

RX = $BrCH_2CO_2$⁀
 $BrCH_2CO_2Me$
 $BrCH_2CN$
 $BrCH_2COMe$

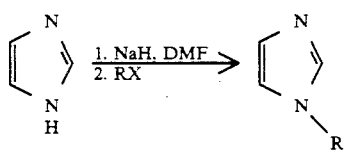

RX = $BrCH_2CH_2OTBDMS$
 $ICH_2CONH_2$

EXAMPLE 49

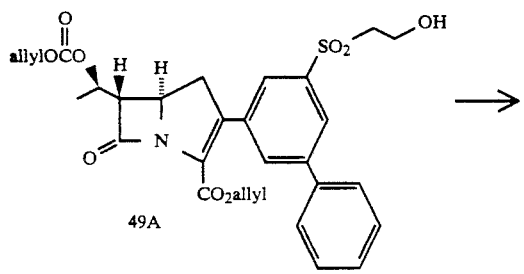

49A

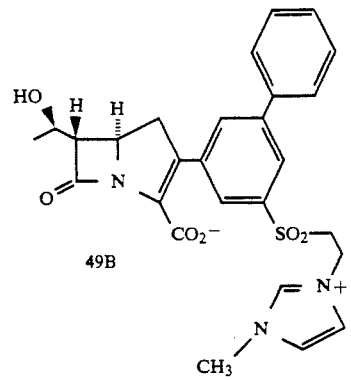

49B

To a stirred solution of the carbapenem (60 mg, 0.103 mmol) in 0.6 mL dry acetonitrile cooled in an ice bath, under $N_2$ atmosphere, was added 2.1 eq. N-methylimidazole (17.2 μl, 0.216 mmol) and 1.05 eq. trifluoromethanesulfonic anhydride (18.2 μl, 0.108 mmol). The reaction was followed by TLC. After 15 minutes, the TLC indicated the complete disappearance of starting material. The reaction mixture was concentrated in vacuo. The 200 MHz NMR of the residue indicated the presence of a mixture of vinylsulfone and the desired imidazolium adduct. The crude product was dissolved in dichloromethane, transferred into a 15 ml centrifuge tube, concentrated to a 1.0 ml volume and the imidazolium adduct precipitated by the addition of diethyl ether. The mixture was centrifuged, the ether decanted off and the precipitate washed analogously twice with either to give a yellow oil, which became a foam when dried in vacuo.

To the imidazolium adduct (23 mg, 0.0314 mmol) in 1.3 mL dry dichloromethane stirred at 0° C. under a $N_2$ atmosphere was added triphenylphosphine (4.9 mg, 18.7 mmol), 69 μl (0.346 mmol) of a 0.5M solution of potassium-2-ethylhexanoate in ethyl acetate, 2-ethyl hexanoic acid (5.0 μL, 34.6 mmol) and tetrakistriphenylphosphinepalladium (0) (7.3 mg, 0.0063 mmol). The reaction was stirred at room temperature for 5 minutes, and then at 0° C. for 2.5 hours. The reaction appeared complete by reverse phase TLC (30% THF/$H_2O$). The reaction mixture was triturated with diethyl ether and the crude separated product isolated by centrifugation and decantation fo the supernatant. The crude product was analogously washed twice with either. The white solid product was dried in vacuo, and then chromatographed on a 1000μ reverse phase silica gel plate eluted with 30% THF in $H_2O$ in the cold. After extraction of the product band with acetonitrile-water (4:1), the solution was filtered through a 0.45μ ACRODISC-CR filter and the filrate concentrated in vacuo and lyophilized to give a granular solid, 7.2 mg (44.5%).

1H NMR (200 MHz, $D_2O$, ppm) δ: 1.32 (d, 3H); 3.14–3.48 (m, 2H), 2.5 (s, 3H), 3.84 (m, 1H), 4.1 (m, 2H), 4.3 (m, 2H), 4.66 (m, 2H), 7.1–7.8 (m, 11H).

IR nujol): 1755, 1600 $cm^{-1}$.

UV ($H_2O$): λmax 306, 258.5 nm.

EXAMPLE 50

In a fashion analogous to that described in Examples 30 and 49, the following was completed.

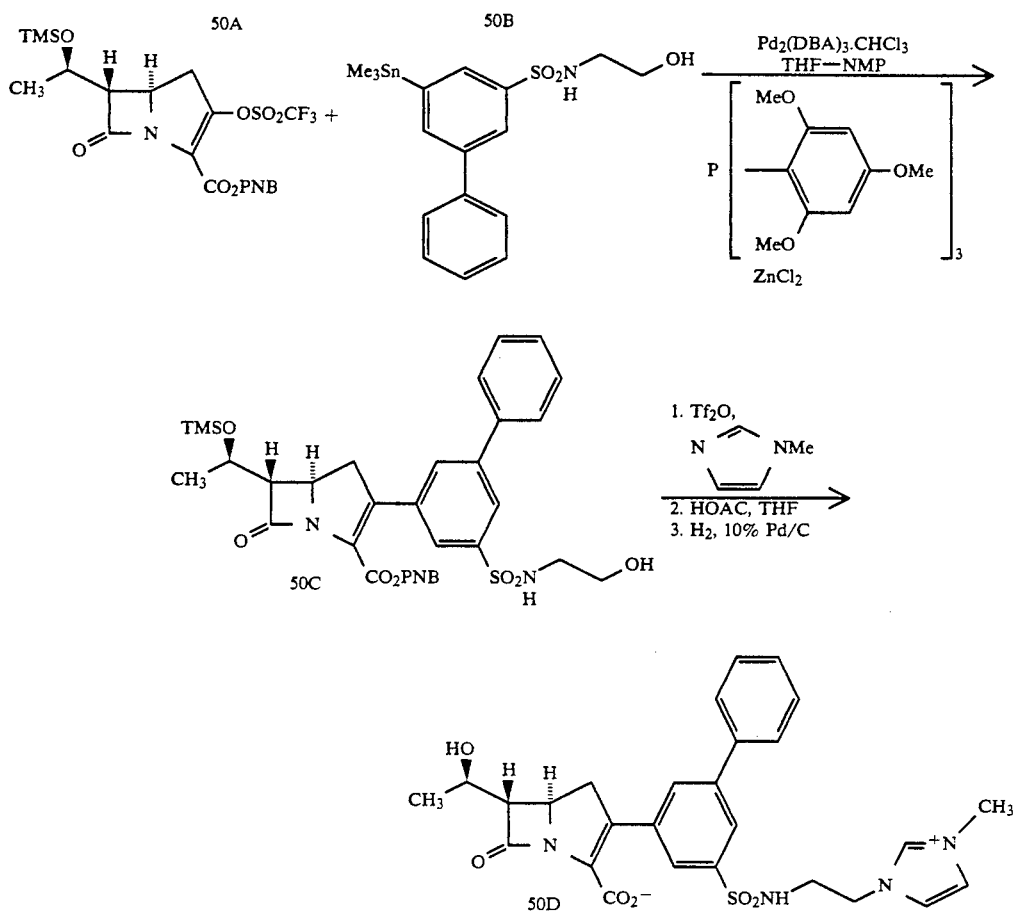
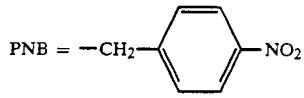
DBA = dibenzylideneacetone
NMP = N-methylpyrrolidinone
Tf$_2$O = (CF$_3$SO$_2$)$_2$O
EXAMPLES 51-94
Employing the procedures described above, additional compounds of the present invention were prepared. These are described in the table below, which additionally includes characterizing data for each compound. In this table, Me=methyl (—CH$_3$).

TABLE I

[Structure: carbapenem core with hydroxyethyl group, R substituent, and biphenyl system bearing $R^a$ groups at positions 3', 4', 5', 6', 2'; carboxylate $CO_2M$ at position; biphenyl attached at position 3 of pyrroline, numbered 2, 4, 6 on proximal ring and 2', 6', 4' (with $R^a$), 5' ($R^a$), 3' on distal ring]

| Ex # | R | 5 | 5' | 4' | 3' | M | H$_2$O $\lambda_{max}$ (nm) |
|---|---|---|---|---|---|---|---|
| 51 | H | H | H | –CH$_2$N(pyridinyl-2-ylidene =NH) | H | H | 300, 260 |
|  | H | H | H | –CH$_2$N$^+$(pyridyl with 3-NH$_2$) | H | H | 303, 257 |
|  | H | H | H | –CH$_2$N$^+$(pyridyl with 3-CH$_2$SMe) | H | (—) | 300, 258 |
|  | H | H | H | –CH$_2$N$^+$(pyridyl with 3-CH$_2$S(O)Me) | H | (—) | 300, 261 |
| 55 | H | H | H | –CH$_2$N$^+$(pyridyl) | H | (—) | 300, 258 |
|  | H | H | H | –CH$_2$N$^+$(N-Me-imidazolyl) | H | (—) | 300, 258 |
|  | H | H | H | –CH$_2$N(pyridin-2-ylidene =NMe) | H | H | 305, 258 |
|  | H | H | H | –N(pyrrolidinyl) | H | H | 298 |
|  | H | H | H | –N$^+$(Me)(pyrrolidinyl) | H | (—) | 297 |
| 60 | H | H | H | –CH$_2$N$^+$(Me)(pyrrolidinyl) | H | (—) | 300, 260 |

TABLE I-continued

[Structure: carbapenem with biphenyl substituent at position 3, showing 5, 5', 4', 3' positions on the biphenyl with R^a substituents, CO_2M group, and hydroxyethyl side chain]

| Ex # | R | 5 | 5' | 4' | 3' | M | H_2O λ_max (nm) |
|---|---|---|---|---|---|---|---|
| | H | H | H | −CH_2N^+(Me)(morpholine) | H | (−) | 300, 261 |
| | H | H | H | −CH_2N=(3-OMe, 2-NH pyridine) | H | H | 301, 250 |
| | H | H | H | −CH_2N=(2-NH pyridine) | H | H | 300, 254 |
| | H | H | H | −CH_2N^+=(thiazine) | H | (−) | 300, 256 |
| 65 | H | H | −N(pyrrolidine) | H | H | H | 302 |
| | H | H | −N^+(Me)(pyrrolidine) | H | H | (−) | 300, 250 |
| | H | F | H | −CH_2N^+=(N-Me imidazole) | H | (−) | 300, 256 |
| | H | H | H | −CH_2N^+=(5-Me thiazine) | H | (−) | 300, 256 |
| | H | H | H | −CH_2N^+=(4-Me thiazine) | H | (−) | 300, 257 |

TABLE I-continued

Structure: bicyclic β-lactam (carbapenem) with 1-hydroxyethyl group, R substituent, and biphenyl at position 3 bearing R^a substituents at 2,4,5,6,2',3',4',5',6' positions; CO₂M on the pyrroline.

| Ex # | R | R^a 5 | R^a 5' | R^a 4' | R^a 3' | M | H₂O λ_max (nm) |
|---|---|---|---|---|---|---|---|
| 70 | H | H | H | —CH₂N⁺=CH—S—C(Me)=C—CH₂CH₂OH (thiazolium with Me and CH₂CH₂OH) | H | (—) | 300, 261 |
|  | H | H | H | —CH₂N⁺(pyridinium fused to thiophene, thieno[3,2-b]pyridinium) | H | (—) | 298, 260 (sh), 242 |
|  | H | H | H | —CH₂N⁺(isoquinolinium) | H | (—) | 308, 259, 238 |
|  | H | H | H | —CH₂N⁺(isoquinolinium-1-yl with C(=NH)NH₂ / amidino substituted) | H | H | 343, 330, 243 |
|  | H | H | H | —CH₂N⁺(pyridinium, 3-CH₂SMe, 4-NH₂) | H | (—) | 304, 260 |
| 75 | H | H | H | —CH₂N⁺(pyridinium, 3-CH₂-pyrrol-1-yl) | H | (—) | 300, 260 |
|  | H | H | H | —CH₂N⁺(pyridinium, 3-CH₂S(=O)Me, 4-NH₂) | H | (—) | 300, 254 |

TABLE I-continued

| Ex # | R | 5 | 5' | 4' | 3' | M | $H_2O$ $\lambda_{max}$ (nm) |
|---|---|---|---|---|---|---|---|
| | H | H | H | −CH$_2$N$^+$⟨pyridinium⟩-SMe | H | (−) | 300, 269 |
| | H | H | H | −CH$_2$N$^+$⟨pyridinium⟩-S(O)Me | H | (−) | 300, 257 |
| | β-Me | H | H | −CH$_2$N⟨dihydropyridine⟩=NH | H | H | 300, 258 |
| 80 | β-Me | H | H | −CH$_2$N$^+$⟨pyridinium⟩-NMe | H | (−) | 300 |
| | H | H | H | −CH$_2$N⟨dihydropyridine, CH$_2$S(O)Me⟩=NH | H | H | 298 |
| | H | H | H | −CH$_2$N$^+$⟨imidazolium, CH$_2$CH$_2$OH⟩ | H | (−) | 298, 255 |
| | H | H | H | −CH$_2$N$^+$⟨imidazolium, CH$_2$CO$_2$Na⟩ | H | (−) | 298, 256 |
| | H | H | H | −CH$_2$N⟨dihydropyridine, CH$_2$OH⟩=NH | H | H | 295, 257 |
| 85 | H | H | H | −CH$_2$N⟨dihydropyridine, CH$_2$SCH$_3$⟩=NH | H | H | 303, 243 |

TABLE I-continued
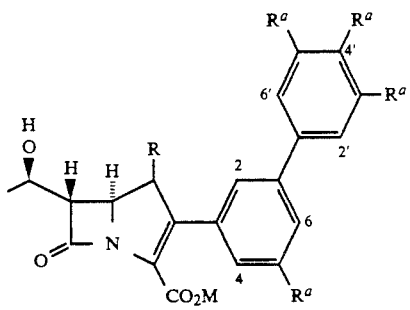
| Ex # | R | $R^a$ 5 | 5' | 4' | 3' | M | $H_2O$ $\lambda_{max}$ (nm) |
|---|---|---|---|---|---|---|---|
| | H | H | H | —CH$_2$N= pyridine with CH$_2$OH and =NH | H | H | 298, 257, 238 |
| | H | H | H | —CH$_2$N= pyridazine with two CH$_3$ and =NH | H | H | 300, 252.5 |
| | H | H | H | —CH$_2$N$^+$= pyridinium with thiophene | H | (—) | 300, 259 |
| | H | H | H | —CH$_2$N$^+$= pyridinium with SCH$_3$ and CH$_2$SCH$_3$ | H | (—) | 310, 231 |
| 90 | H | —S—CH$_2$CH$_2$—N$^+$ imidazole NMe | H | H | H | (—) | 305 |
| | H | —SO$_2$—CH$_2$CH$_2$—N$^+$ imidazole NMe | H | H | H | (—) | 306, 258.5 |
| | H | H | H | —CH$_2$N= imidazo-pyridine | H | H | 300, 258 |

TABLE I-continued
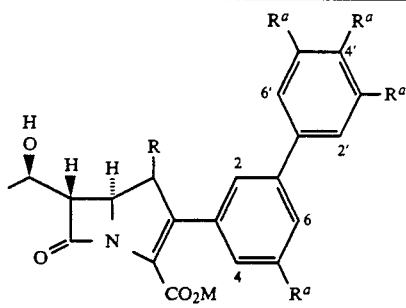
| | | $R^a$ | | | | $H_2O$ $\lambda_{max}$ |
|---|---|---|---|---|---|---|
| Ex # | R | 5 | 5' | 4' | 3' | M | (nm) |
| | H | H | H | 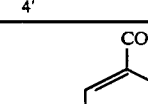 | H | H | 300, 257 |
| | H | ![sulfonamide imidazolium] | H | H | H | (—) | 305 |
EXAMPLES 95-162
Following the procedures described above, further examples of compounds of the present invention may be prepared, as set out in the table below. In this table, Me=methyl (—CH₃).

TABLE II
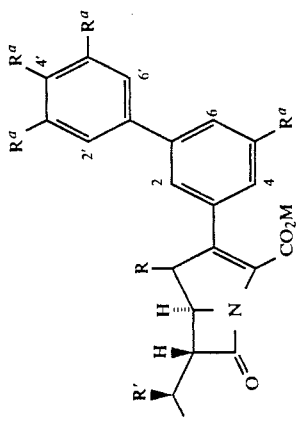
| Ex # | R' | R | 5 | 5' | 4' $R^a$ | 3' | M |
|---|---|---|---|---|---|---|---|
| 95 | OH | H | OH | H | ![pyridyl-CH2 with =NH] —CH2—(2-iminopyridyl) | H | H |
|  | F | H | OH | H | ![pyridyl-CH2 with =NH] —CH2—(2-iminopyridyl) | H | H |
|  | F | β-Me | H | H | ![pyridyl-CH2 with =NH] —CH2—(2-iminopyridyl) | H | H |
|  | OH | H | H | H | ![N-CH2CH2-O- with 2-imino pyridyl] | H | H |

TABLE II-continued
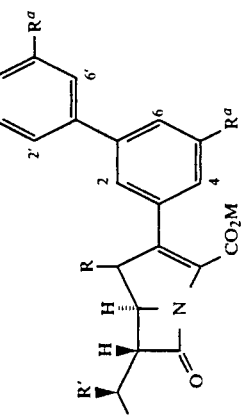
| Ex # | R' | R | 5 | 5' | 4' | 3' | M |
|---|---|---|---|---|---|---|---|
| | OH | H | —SO₂Me | H | ![pyridinylidene]-CH₂— with NH | H | H |
| 100 | OH | H | —CONH₂ | H | ![pyridinylidene]-CH₂— with NH | H | H |
| | OH | H | —SO₂Me | H | ![pyridinium NMe]-CH₂—⁺N | H | (−) |
| | OH | H | —CONH₂ | H | ![pyridinium NMe]-CH₂—⁺N | H | (−) |
| | OH | H | H | H | ![pyridinium with CONH₂]-CH₂—⁺N with CONH₂ | H | (−) |
| | OH | H | H | H | ![imidazolium NMe]-CH₂—⁺N=N | H | (−) |

TABLE II-continued
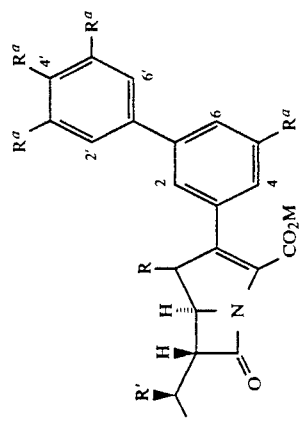
| Ex # | R' | R | 5 | 5' | 4' | 3' | M |
|---|---|---|---|---|---|---|---|
| 105 | OH | H | H | H | —CH₂—N⁺(ring)—SO₃Na | H | (−) |
|  | OH | H | H | H | —SO₂—(ring, NMe) | H | (−) |
|  | OH | H | CONH₂ | OH | H | —CH₂—N⁺(ring, NMe) | (−) |
|  | OH | H | H | CONH₂ | H | —CH₂—N(pyridinylidene, NH) | H |
|  | OH | H | CN | H | —CH₂—N(pyridinylidene, NH) | H | H |

TABLE II-continued
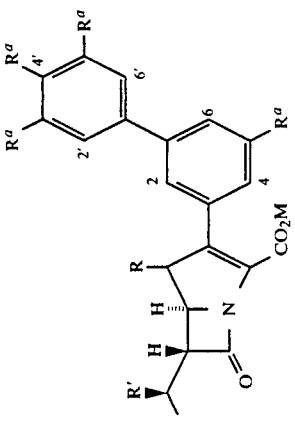
| Ex # | R' | R | 5 | 5' | 4' | 3' | M |
|---|---|---|---|---|---|---|---|
| 110 | OH | H | ![pyridine-NH with SCH2CH2]  2-iminopyridinium-ethylthio | H | H | H | H |
|  | OH | H | 4-iminopyridinium-ethylthio (=NH) | H | H | H | H |
|  | OH | H | 4-aminopyridinium-ethylthio (NH2) | H | H | H | (−) |
|  | OH | H | N-methylimidazolium-ethylsulfinyl (NCH3) | H | H | H | (−) |
|  | OH | H | N-(2-hydroxyethyl)imidazolium-ethylsulfinyl (OH) | H | H | H | (−) |

TABLE II-continued
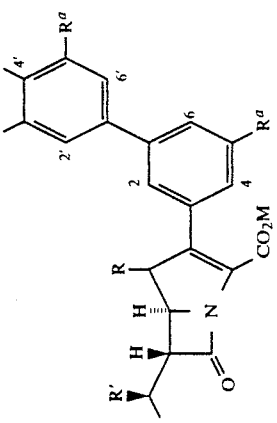
| Ex # | R' | R | 5 | 5' | 4' | 3' | M |
|---|---|---|---|---|---|---|---|
| 115 | OH | H | —S(=O)—CH₂CH₂—N⁺(pyridinium)=NH | H | H | H | H |
|  | OH | H | —S(=O)—CH₂CH₂—N⁺(pyridinium)-NH₂ | H | H | H | (—) |
|  | OH | H | —S—CH₂CH₂—N⁺(imidazolium)  | H | H | H | (—) |
|  | OH | H | —SO₂—CH₂CH₂—N⁺(imidazolium with CH₂CH₂OH) | H | H | H | (—) |
|  | OH | H | —SO₂—CH₂CH₂—N(pyridinium)=NH | H | H | H | H |

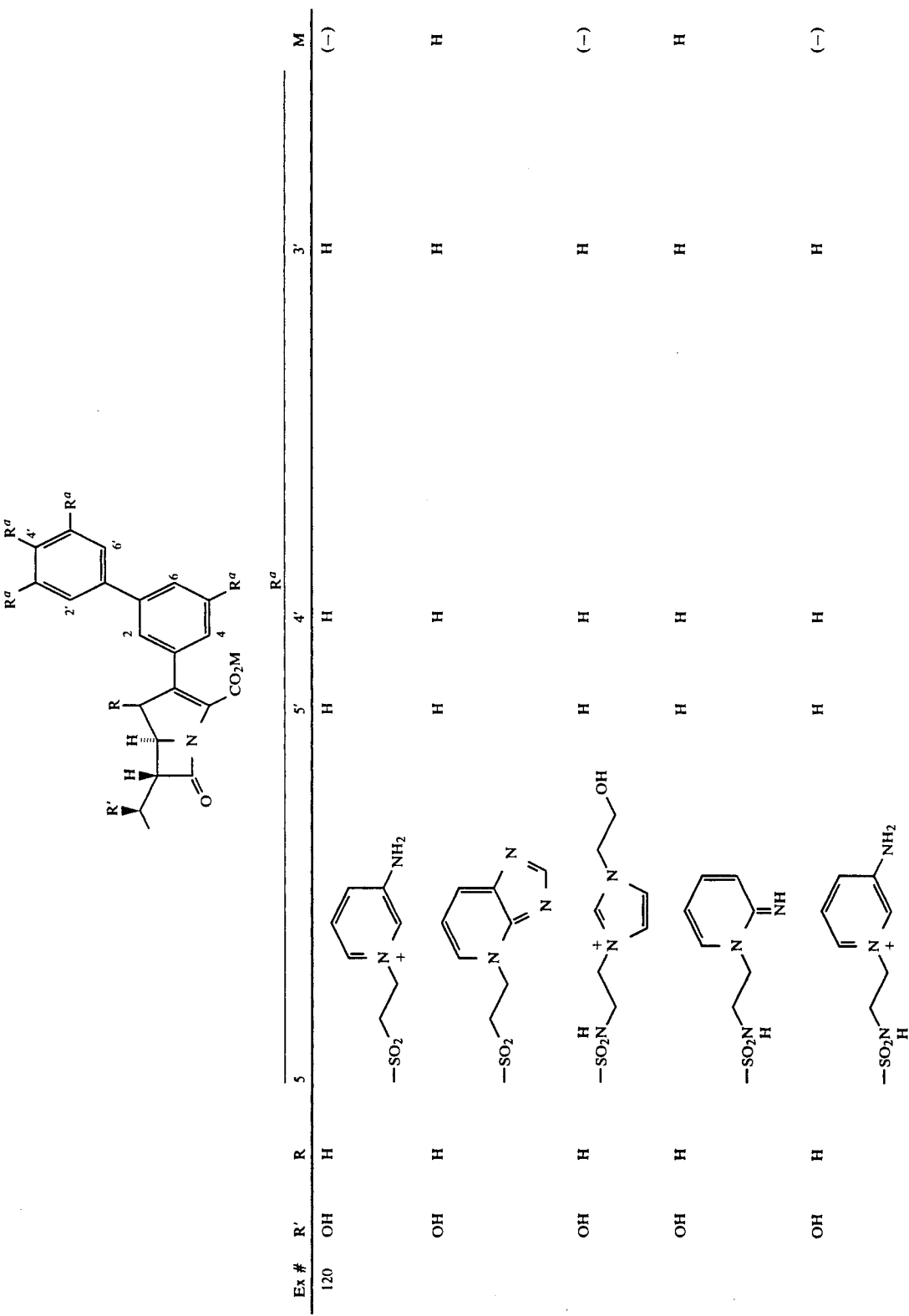

TABLE II-continued

[Structure: biphenyl-substituted pyrrolidinone with CO₂M group; substituents R, R', R^a positions shown at 2', 3', 4', 5', 6' and 2, 4, 5, 6]

| Ex # | R' | R | 5 | 5' | 4' | 3' | M |
|---|---|---|---|---|---|---|---|
| 125 | OH | H | —SO$_2$N(H)-CH$_2$CH$_2$-(imidazo[4,5-b]pyridine) | H | H | H | H |
| | OH | H | H | H | $-\text{N}^+(=\text{CH-CH=CH-CH=})\text{CH}_2\text{CF}_3$ (pyridinium-CH$_2$CF$_3$) | H | (−) |
| | OH | H | H | H | $-\text{N}^+(=\text{CH-CH=CH-CH=})\text{CH}_2\text{C(O)Me}$ (pyridinium-CH$_2$C(O)Me) | H | (−) |
| | OH | H | H | H | $-\text{N}^+(=\text{CH-CH=CH-CH=})\text{CH}_2\text{CO}_2\text{Me}$ (pyridinium-CH$_2$CO$_2$Me) | H | (−) |
| | OH | H | H | H | (2-methylpyrazolium, N-CH$_2$-) | H | (−) |
| 130 | OH | H | H | H | (pyridazinium, N$^+$=N, N-CH$_2$-) | H | (−) |

TABLE II-continued

| Ex # | R' | R | 5 | 5' | 4' (Rᵃ) | 3' | M |
|---|---|---|---|---|---|---|---|
| | OH | H | H | H | [imidazolium-CH₂-N⁺-CH₂-NMe] | H | (−) |
| | OH | H | H | H | [imidazo-pyridine N-ethyl] | H | H |
| | OH | H | H | H | [pyridinium-CHO, NMe] | H | (−) |
| | OH | H | H | H | −S⁺(CH₃)₂ | H | (−) |
| | OH | H | H | H | [pyridinium =NH] | H | H |
| 135 | OH | H | CHO | H | [N⁺-ethyl pyridinium-NCH₃, NMe] | H | (−) |
| | OH | H | CHO | H | | H | |

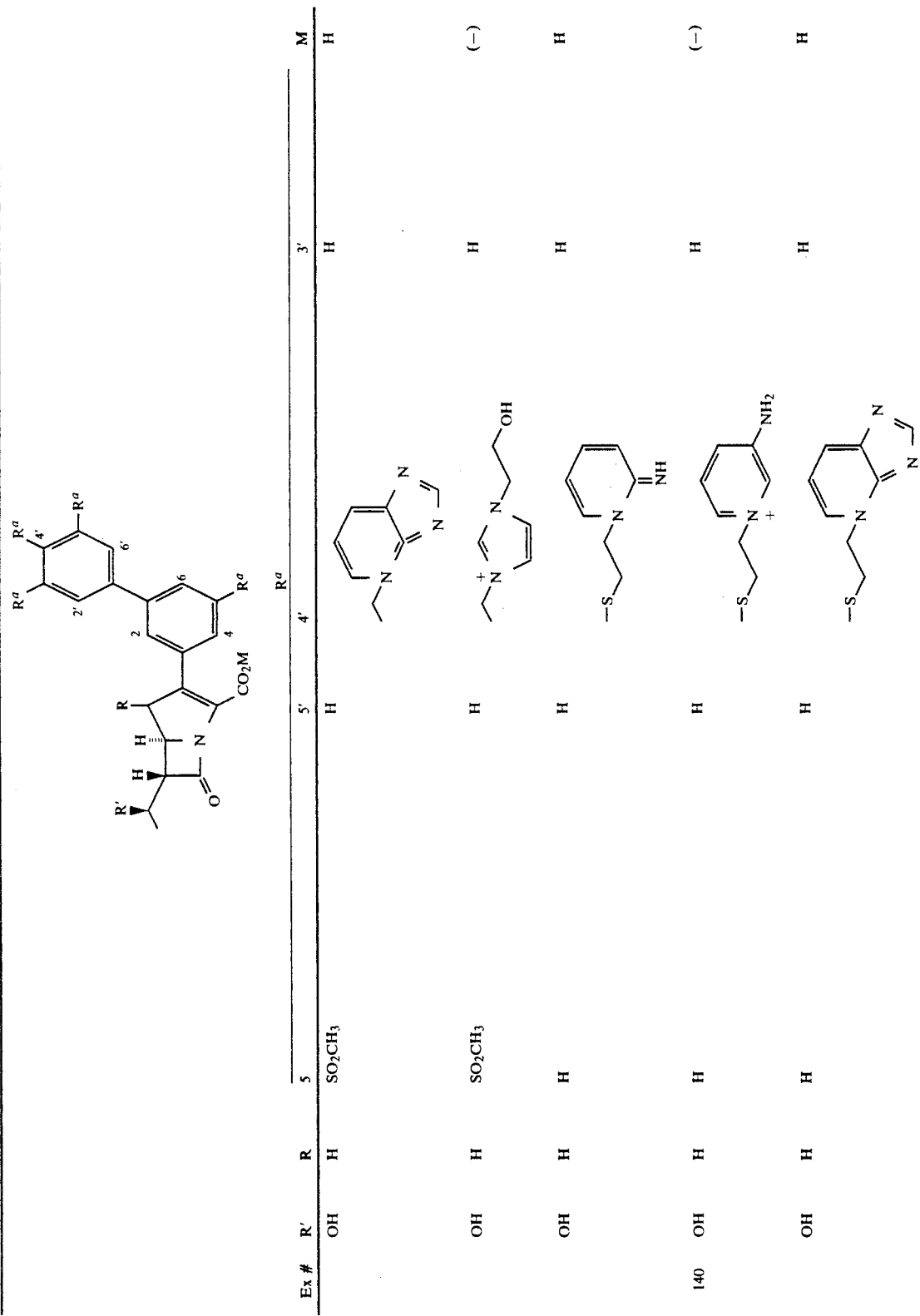

TABLE II-continued
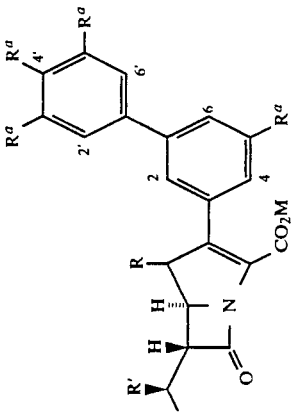
| Ex # | R' | R | 5 | R$^a$ 4' | 3' | M |
|---|---|---|---|---|---|---|
| | OH | H | H | -S-CH₂CH₂-N⁺(pyridinium)-NCH₃ | H | (−) |
| | OH | H | H | -S-CH₂CH₂-N⁺(pyridinium)-N-CH₂CH₂OH | H | (−) |
| | OH | H | H | pyridine-2-imine-N-CH₂CH₂-S- | H | H |
| | OH | H | H | O=S-CH₂CH₂-N⁺(pyridinium)-NH₂ | H | (−) |
| 145 | OH | H | H | O=S-CH₂CH₂-N⁺(pyridinium)-NCH₃ | H | (−) |
| | OH | H | H | O=S-CH₂CH₂-N⁺(pyridinium)-N-CH₂CH₂OH | H | (−) |

TABLE II-continued
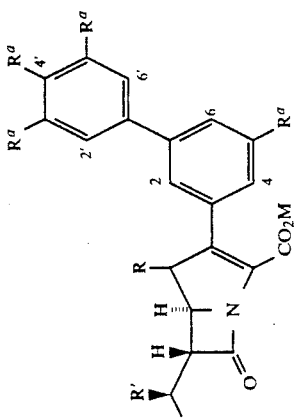
| Ex # | R' | R | 5 | 5' | 4' | 3' | M |
|---|---|---|---|---|---|---|---|
|  | OH | H | H | H | ![pyridinylidene-NH SO2-ethyl] | H | H |
|  | OH | H | H | H | ![4-aminophenyl-pyridinium SO2-ethyl] | H | (−) |
|  | OH | H | H | H | ![pyridinium-NCH3 SO2-ethyl] | H | (−) |
|  | OH | H | H | H | ![pyridinium-N-ethanol SO2-ethyl] | H | (−) |
| 150 | OH | H | H | H | ![imidazo-pyridine SO2-ethyl] | H | H |

TABLE II-continued
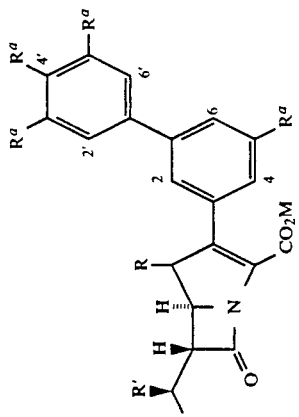
| Ex # | R' | R | 5 | R$^a$ 5' | R$^a$ 4' | 3' | M |
|---|---|---|---|---|---|---|---|
| | OH | H | H | H | (pyridinylidene-NH structure) | H | H |
| | OH | H | H | H | (pyridinium-NH$_2$) | H | (−) |
| 155 | OH | H | H | H | (imidazolium-NCH$_3$) | H | (−) |
| | OH | H | H | H | (imidazolium-N-CH$_2$CH$_2$OH) | H | (−) |
| | OH | H | H | H | (benzimidazole) | H | H |

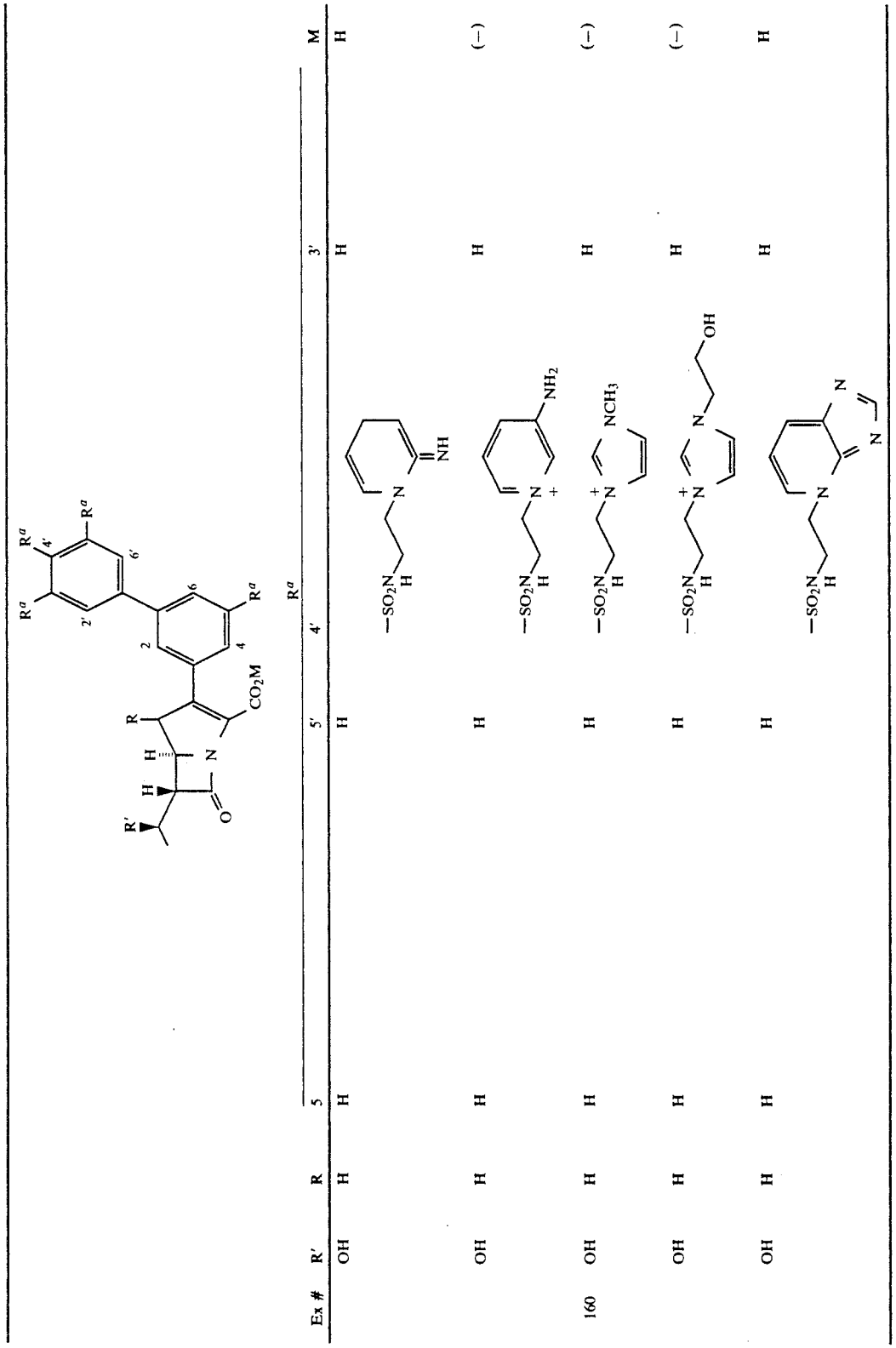

What is claimed is:

1. A compound of the formula

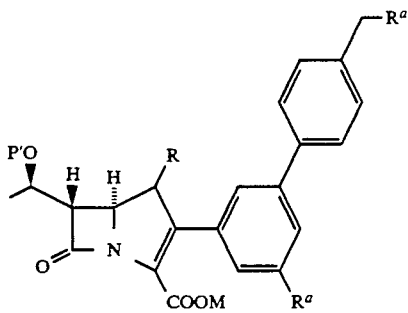

where

R is H or CH₃;

P' is a removable protecting group for hydroxy;

Rᵃ is selected from the group consisting of H, Cl, Br, I, SMe, CN, CHO, SOMe, SO₂Me, and OP';

M is a removable protecting group for carboxyl; and

Z is an effective leaving group selected from the group consisting of alkyl and substituted alkylsulfonates, aryl and substituted arylsulfonates, and halides.

2. The compound of claim 1 wherein M is selected from the group consisting of benzhydryl, p-nitrobenzyl, 2-naphthylmethyl, allyl, benzyl, trichloroethyl, trimethylsilyl, t-butyldiphenylsilyl, phenacyl, p-methoxybenzyl, acetonyl, o-nitrobenzyl and 4-pyridylmethyl.

3. The compound of claim 1 wherein P' is selected from the group consisting of methoxy-t-butylphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

4. The compound of claim 1 wherein Z is selected from the group consisting of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

* * * * *

UNITED STATES PATENT AND TRADEMARK OFFICE
CERTIFICATE OF CORRECTION

PATENT NO. : 5,208,329
DATED : May 4, 1993
INVENTOR(S) : Frank P. Dininno, et al It is certified that error appears in the above-indentified patent and that said Letters Patent is hereby corrected as shown below:

Column 119, between lines 5-17, in claim 1, should read as follows: --.

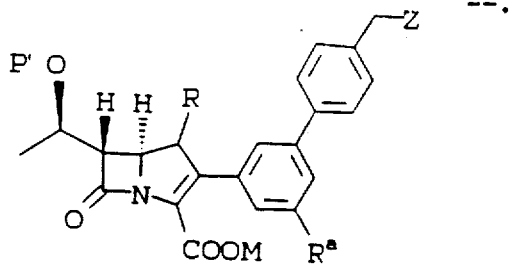

Signed and Sealed this

Twenty-fourth Day of May, 1994

*Attest:*

BRUCE LEHMAN

*Attesting Officer*     Commissioner of Patents and Trademarks